US012056264B2

(12) United States Patent
Peck

(10) Patent No.: US 12,056,264 B2
(45) Date of Patent: Aug. 6, 2024

(54) NUCLEIC ACID BASED DATA STORAGE

(71) Applicant: Twist Bioscience Corporation, South San Francisco, CA (US)

(72) Inventor: Bill James Peck, Santa Clara, CA (US)

(73) Assignee: Twist Bioscience Corporation, South San Francisco, CA (US)

( * ) Notice: Subject to any disclaimer, the term of this patent is extended or adjusted under 35 U.S.C. 154(b) by 0 days.

(21) Appl. No.: 17/938,228

(22) Filed: Oct. 5, 2022

(65) Prior Publication Data

US 2023/0054232 A1 Feb. 23, 2023

Related U.S. Application Data

(63) Continuation of application No. 17/578,356, filed on Jan. 18, 2022, now Pat. No. 11,562,103, which is a continuation of application No. 16/927,826, filed on Jul. 13, 2020, now Pat. No. 11,263,354, which is a continuation of application No. 16/415,960, filed on
(Continued)

(51) Int. Cl.
*G06F 21/78* (2013.01)
*C12N 15/10* (2006.01)

(52) U.S. Cl.
CPC ........... *G06F 21/78* (2013.01); *C12N 15/102* (2013.01); *C12N 15/1027* (2013.01); *C12N 15/1089* (2013.01); *G06F 2212/1052* (2013.01); *G06F 2212/402* (2013.01)

(58) Field of Classification Search
CPC ....................................................... G06F 21/78
See application file for complete search history.

(56) References Cited

U.S. PATENT DOCUMENTS 3,549,368 A 12/1970 Collings et al.
3,920,714 A 11/1975 Streck
(Continued)

FOREIGN PATENT DOCUMENTS

AU 3157000 A 9/2000
CA 2362939 A1 8/2000
(Continued)

OTHER PUBLICATIONS

Abudayyeh et al.: C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf 17 pages.
(Continued)

*Primary Examiner* — Bradley W Holder
(74) *Attorney, Agent, or Firm* — Bookoff McAndrews, PLLC

(57) ABSTRACT

Provided herein are compositions, devices, systems and methods for the generation and use of biomolecule-based information for storage. Additionally, devices described herein for de novo synthesis of nucleic acids encoding information related to the original source information may be rigid or flexible material. Further described herein are highly efficient methods for long term data storage with 100% accuracy in the retention of information. Also provided herein are methods and systems for efficient transfer of preselected polynucleotides from a storage structure for reading stored information.

20 Claims, 27 Drawing Sheets

Specification includes a Sequence Listing.

Related U.S. Application Data

May 17, 2019, now Pat. No. 10,754,994, which is a continuation of application No. 15/709,274, filed on Sep. 19, 2017, now Pat. No. 10,417,457.

(60) Provisional application No. 62/517,671, filed on Jun. 9, 2017, provisional application No. 62/446,178, filed on Jan. 13, 2017, provisional application No. 62/397,855, filed on Sep. 21, 2016.

(56) References Cited

U.S. PATENT DOCUMENTS

| | | |
|---|---|---|
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman |
| 5,299,491 A | 4/1994 | Kawada |
| 5,368,823 A | 11/1994 | McGraw et al. |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes |
| 5,530,516 A | 6/1996 | Sheets |
| 5,534,507 A | 7/1996 | Cama et al. |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,712,126 A | 1/1998 | Weissman et al. |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |

(56) References Cited

U.S. PATENT DOCUMENTS

| | | |
|---|---|---|
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van De Goor et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,841 B2 | 3/2004 | Short |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Stahler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |

(56) References Cited

U.S. PATENT DOCUMENTS

| | | | |
|---|---|---|---|
| 7,193,077 | B2 | 3/2007 | Dellinger et al. |
| 7,195,872 | B2 | 3/2007 | Agrawal et al. |
| 7,198,939 | B2 | 4/2007 | Dorsel et al. |
| 7,202,264 | B2 | 4/2007 | Ravikumar et al. |
| 7,202,358 | B2 | 4/2007 | Hargreaves |
| 7,205,128 | B2 | 4/2007 | Ilsley et al. |
| 7,205,399 | B1 | 4/2007 | Vargeese et al. |
| 7,205,400 | B2 | 4/2007 | Webb |
| 7,206,439 | B2 | 4/2007 | Zhou et al. |
| 7,208,322 | B2 | 4/2007 | Stolowitz et al. |
| 7,217,522 | B2 | 5/2007 | Brenner |
| 7,220,573 | B2 | 5/2007 | Shea et al. |
| 7,221,785 | B2 | 5/2007 | Curry et al. |
| 7,226,862 | B2 | 6/2007 | Staehler et al. |
| 7,227,017 | B2 | 6/2007 | Mellor et al. |
| 7,229,497 | B2 | 6/2007 | Stott et al. |
| 7,247,337 | B1 | 7/2007 | Leproust et al. |
| 7,247,497 | B2 | 7/2007 | Dahm et al. |
| 7,252,938 | B2 | 8/2007 | Leproust et al. |
| 7,269,518 | B2 | 9/2007 | Corson |
| 7,271,258 | B2 | 9/2007 | Dellinger et al. |
| 7,276,336 | B1 | 10/2007 | Webb et al. |
| 7,276,378 | B2 | 10/2007 | Myerson |
| 7,276,599 | B2 | 10/2007 | Moore et al. |
| 7,282,183 | B2 | 10/2007 | Peck |
| 7,282,332 | B2 | 10/2007 | Caren et al. |
| 7,282,705 | B2 | 10/2007 | Brennen |
| 7,291,471 | B2 | 11/2007 | Sampson et al. |
| 7,302,348 | B2 | 11/2007 | Ghosh et al. |
| 7,306,917 | B2 | 12/2007 | Prudent et al. |
| 7,314,599 | B2 | 1/2008 | Roitman et al. |
| 7,323,320 | B2 | 1/2008 | Oleinikov |
| 7,344,831 | B2 | 3/2008 | Wolber et al. |
| 7,348,144 | B2 | 3/2008 | Minor |
| 7,351,379 | B2 | 4/2008 | Schleifer |
| 7,353,116 | B2 | 4/2008 | Webb et al. |
| 7,361,906 | B2 | 4/2008 | Ghosh et al. |
| 7,364,896 | B2 | 4/2008 | Schembri |
| 7,368,550 | B2 | 5/2008 | Dellinger et al. |
| 7,371,348 | B2 | 5/2008 | Schleifer et al. |
| 7,371,519 | B2 | 5/2008 | Wolber et al. |
| 7,371,580 | B2 | 5/2008 | Yakhini et al. |
| 7,372,982 | B2 | 5/2008 | Le Cocq |
| 7,384,746 | B2 | 6/2008 | Lyamichev et al. |
| 7,385,050 | B2 | 6/2008 | Dellinger et al. |
| 7,390,457 | B2 | 6/2008 | Schembri |
| 7,393,665 | B2 | 7/2008 | Brenner |
| 7,396,676 | B2 | 7/2008 | Robotti et al. |
| 7,399,844 | B2 | 7/2008 | Sampson et al. |
| 7,402,279 | B2 | 7/2008 | Schembri |
| 7,411,061 | B2 | 8/2008 | Myerson et al. |
| 7,413,709 | B2 | 8/2008 | Roitman et al. |
| 7,417,139 | B2 | 8/2008 | Dellinger et al. |
| 7,422,911 | B2 | 9/2008 | Schembri |
| 7,427,679 | B2 | 9/2008 | Dellinger et al. |
| 7,432,048 | B2 | 10/2008 | Neri et al. |
| 7,435,810 | B2 | 10/2008 | Myerson et al. |
| 7,439,272 | B2 | 10/2008 | Xu |
| 7,476,709 | B2 | 1/2009 | Moody et al. |
| 7,482,118 | B2 | 1/2009 | Allawi et al. |
| 7,488,607 | B2 | 2/2009 | Tom-Moy et al. |
| 7,504,213 | B2 | 3/2009 | Sana et al. |
| 7,514,369 | B2 | 4/2009 | Li et al. |
| 7,517,979 | B2 | 4/2009 | Wolber |
| 7,524,942 | B2 | 4/2009 | Wang et al. |
| 7,524,950 | B2 | 4/2009 | Dellinger et al. |
| 7,527,928 | B2 | 5/2009 | Neri et al. |
| 7,531,303 | B2 | 5/2009 | Dorsel et al. |
| 7,534,561 | B2 | 5/2009 | Sana et al. |
| 7,534,563 | B2 | 5/2009 | Hargreaves |
| 7,537,936 | B2 | 5/2009 | Dahm et al. |
| 7,541,145 | B2 | 6/2009 | Prudent et al. |
| 7,544,473 | B2 | 6/2009 | Brenner |
| 7,556,919 | B2 | 7/2009 | Chenchik et al. |
| 7,563,600 | B2 | 7/2009 | Oleinikov |
| 7,572,585 | B2 | 8/2009 | Wang |
| 7,572,907 | B2 | 8/2009 | Dellinger et al. |
| 7,572,908 | B2 | 8/2009 | Dellinger et al. |
| 7,585,970 | B2 | 9/2009 | Dellinger et al. |
| 7,588,889 | B2 | 9/2009 | Wolber et al. |
| 7,595,350 | B2 | 9/2009 | Xu |
| 7,604,941 | B2 | 10/2009 | Jacobson |
| 7,604,996 | B1 | 10/2009 | Stuelpnagel et al. |
| 7,608,396 | B2 | 10/2009 | Delenstarr |
| 7,618,777 | B2 | 11/2009 | Myerson et al. |
| 7,629,120 | B2 | 12/2009 | Bennett et al. |
| 7,635,772 | B2 | 12/2009 | McCormac |
| 7,648,832 | B2 | 1/2010 | Jessee et al. |
| 7,651,762 | B2 | 1/2010 | Xu et al. |
| 7,659,069 | B2 | 2/2010 | Belyaev et al. |
| 7,678,542 | B2 | 3/2010 | Lyamichev et al. |
| 7,682,809 | B2 | 3/2010 | Sampson |
| 7,709,197 | B2 | 5/2010 | Drmanac |
| 7,718,365 | B2 | 5/2010 | Wang |
| 7,718,786 | B2 | 5/2010 | Dupret et al. |
| 7,723,077 | B2 | 5/2010 | Young et al. |
| 7,737,088 | B1 | 6/2010 | Stahler et al. |
| 7,737,089 | B2 | 6/2010 | Guimil et al. |
| 7,741,463 | B2 | 6/2010 | Gormley et al. |
| 7,749,701 | B2 | 7/2010 | Leproust et al. |
| 7,759,471 | B2 | 7/2010 | Dellinger et al. |
| 7,776,021 | B2 | 8/2010 | Borenstein et al. |
| 7,776,532 | B2 | 8/2010 | Gibson et al. |
| 7,790,369 | B2 | 9/2010 | Stahler et al. |
| 7,790,387 | B2 | 9/2010 | Dellinger et al. |
| 7,807,356 | B2 | 10/2010 | Sampson et al. |
| 7,807,806 | B2 | 10/2010 | Allawi et al. |
| 7,811,753 | B2 | 10/2010 | Eshoo |
| 7,816,079 | B2 | 10/2010 | Fischer |
| 7,820,387 | B2 | 10/2010 | Neri et al. |
| 7,829,314 | B2 | 11/2010 | Prudent et al. |
| 7,855,281 | B2 | 12/2010 | Dellinger et al. |
| 7,862,999 | B2 | 1/2011 | Zheng et al. |
| 7,867,782 | B2 | 1/2011 | Barth |
| 7,875,463 | B2 | 1/2011 | Adaskin et al. |
| 7,879,541 | B2 | 2/2011 | Kincaid |
| 7,879,580 | B2 | 2/2011 | Carr et al. |
| 7,894,998 | B2 | 2/2011 | Kincaid |
| 7,919,239 | B2 | 4/2011 | Wang |
| 7,919,308 | B2 | 4/2011 | Schleifer |
| 7,927,797 | B2 | 4/2011 | Nobile et al. |
| 7,927,838 | B2 | 4/2011 | Shannon |
| 7,932,025 | B2 | 4/2011 | Carr et al. |
| 7,932,070 | B2 | 4/2011 | Hogrefe et al. |
| 7,935,800 | B2 | 5/2011 | Allawi et al. |
| 7,939,645 | B2 | 5/2011 | Borns |
| 7,943,046 | B2 | 5/2011 | Martosella et al. |
| 7,943,358 | B2 | 5/2011 | Hogrefe et al. |
| 7,960,157 | B2 | 6/2011 | Borns |
| 7,977,119 | B2 | 7/2011 | Kronick et al. |
| 7,979,215 | B2 | 7/2011 | Sampas |
| 7,998,437 | B2 | 8/2011 | Berndt et al. |
| 7,999,087 | B2 | 8/2011 | Dellinger et al. |
| 8,021,842 | B2 | 9/2011 | Brenner |
| 8,021,844 | B2 | 9/2011 | Wang |
| 8,034,917 | B2 | 10/2011 | Yamada |
| 8,036,835 | B2 | 10/2011 | Sampas et al. |
| 8,048,664 | B2 | 11/2011 | Guan et al. |
| 8,053,191 | B2 | 11/2011 | Blake |
| 8,058,001 | B2 | 11/2011 | Crameri et al. |
| 8,058,004 | B2 | 11/2011 | Oleinikov |
| 8,058,055 | B2 | 11/2011 | Barrett et al. |
| 8,063,184 | B2 | 11/2011 | Allawi et al. |
| 8,067,556 | B2 | 11/2011 | Hogrefe et al. |
| 8,073,626 | B2 | 12/2011 | Troup et al. |
| 8,076,064 | B2 | 12/2011 | Wang |
| 8,076,152 | B2 | 12/2011 | Robotti |
| 8,097,711 | B2 | 1/2012 | Timar et al. |
| 8,137,936 | B2 | 3/2012 | Macevicz |
| 8,148,068 | B2 | 4/2012 | Brenner |
| 8,154,729 | B2 | 4/2012 | Baldo et al. |
| 8,168,385 | B2 | 5/2012 | Brenner |
| 8,168,388 | B2 | 5/2012 | Gormley et al. |
| 8,173,368 | B2 | 5/2012 | Staehler et al. |

(56) References Cited

U.S. PATENT DOCUMENTS

| | | |
|---|---|---|
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,102,731 B2 | 8/2015 | Boone et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 | 8/2016 | Banyai et al. |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro et al. |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai et al. |
| 9,879,283 B2 | 1/2018 | Ravinder et al. |
| 9,889,423 B2 | 2/2018 | Banyai et al. |
| 9,895,673 B2 | 2/2018 | Peck et al. |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,251,611 B2 | 4/2019 | Marsh et al. |
| 10,272,410 B2 | 4/2019 | Banyai et al. |
| 10,384,188 B2 | 8/2019 | Banyai et al. |
| 10,384,189 B2 | 8/2019 | Peck |
| 10,417,457 B2 | 9/2019 | Peck |
| 10,583,415 B2 | 3/2020 | Banyai et al. |
| 10,618,024 B2 | 4/2020 | Banyai et al. |
| 10,632,445 B2 | 4/2020 | Banyai et al. |
| 10,639,609 B2 | 5/2020 | Banyai et al. |
| 10,669,304 B2 | 6/2020 | Indermuhle et al. |
| 10,744,477 B2 | 8/2020 | Banyai et al. |
| 10,754,994 B2 | 8/2020 | Peck |
| 10,773,232 B2 | 9/2020 | Banyai et al. |
| 10,844,373 B2 | 11/2020 | Cox et al. |
| 10,894,242 B2 | 1/2021 | Marsh et al. |
| 10,894,959 B2 | 1/2021 | Cox et al. |
| 10,907,274 B2 | 2/2021 | Cox |
| 10,936,953 B2 | 3/2021 | Bramlett et al. |
| 10,963,953 B2 | 3/2021 | Sweeder et al. |
| 10,969,965 B2 | 4/2021 | Malina et al. |
| 10,975,372 B2 | 4/2021 | Cox et al. |
| 10,987,648 B2 | 4/2021 | Peck et al. |

(56) References Cited

U.S. PATENT DOCUMENTS

| | | |
|---|---|---|
| 11,185,837 B2 | 11/2021 | Banyai et al. |
| 11,214,798 B2 | 1/2022 | Brown |
| 11,236,393 B2 | 2/2022 | Dubinsky et al. |
| 11,263,354 B2 | 3/2022 | Peck |
| 11,268,149 B2 | 3/2022 | Targan et al. |
| 11,332,738 B2 | 5/2022 | Nugent et al. |
| 11,332,740 B2 | 5/2022 | Nugent et al. |
| 11,377,676 B2 | 7/2022 | Wu et al. |
| 11,407,837 B2 | 8/2022 | Glanville |
| 11,452,980 B2 | 9/2022 | Banyai et al. |
| 11,492,665 B2 | 11/2022 | Zeitoun et al. |
| 11,492,727 B2 | 11/2022 | Tabibiazar et al. |
| 11,492,728 B2 | 11/2022 | Sato |
| 11,512,347 B2 | 11/2022 | Peck |
| 11,550,939 B2 | 1/2023 | Peck et al. |
| 11,559,778 B2 | 1/2023 | Banyai et al. |
| 11,562,103 B2 | 1/2023 | Peck |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0058802 A1 | 5/2002 | Dellinger et al. |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |
| 2002/0119459 A1 | 8/2002 | Griffiths |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022240 A1 | 1/2003 | Luo et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082618 A1 | 5/2003 | Li et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0130827 A1 | 7/2003 | Bentzien et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0148401 A1 | 8/2003 | Agrawal et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du Breuil Lastrucci |
| 2004/0009498 A1 | 1/2004 | Short |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0213795 A1 | 10/2004 | Collins et al. |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0253242 A1 | 12/2004 | Bowdish et al. |
| 2004/0259146 A1 | 12/2004 | Friend et al. |
| 2005/0022895 A1 | 2/2005 | Barth et al. |
| 2005/0049402 A1 | 3/2005 | Babcook et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0118706 A1 | 6/2005 | Pirrung et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0214778 A1 | 9/2005 | Peck et al. |
| 2005/0214779 A1 | 9/2005 | Peck et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2005/0287585 A1 | 12/2005 | Oleinikov |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2006/0286569 A1* | 12/2006 | Bar-Or ............... C12Q 1/68 380/59 |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099196 A1 | 5/2007 | Kauppinen et al. |
| 2007/0099208 A1 | 5/2007 | Drmanac et al. |
| 2007/0122817 A1 | 5/2007 | Church et al. |
| 2007/0128635 A1 | 6/2007 | Macevicz |
| 2007/0141557 A1 | 6/2007 | Raab et al. |
| 2007/0196834 A1 | 8/2007 | Cerrina et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0233403 A1 | 10/2007 | Alwan et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |

(56) References Cited

U.S. PATENT DOCUMENTS

| | | |
|---|---|---|
| 2009/0053704 A1 | 2/2009 | Novoradovskaya et al. |
| 2009/0062129 A1 | 3/2009 | McKernan et al. |
| 2009/0074771 A1 | 3/2009 | Koenig et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0008851 A1 | 1/2010 | Nicolaides et al. |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0111768 A1 | 5/2010 | Banerjee et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0272711 A1 | 10/2010 | Feldman et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2010/0311960 A1 | 12/2010 | Dellinger |
| 2010/0323404 A1 | 12/2010 | Lathrop |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0201528 A1 | 8/2011 | Baek et al. |
| 2011/0217738 A1 | 9/2011 | Jacobson |
| 2011/0229975 A1 | 9/2011 | Matthiesen et al. |
| 2011/0230653 A1 | 9/2011 | Novoradovskaya et al. |
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0014790 A1 | 1/2013 | Van Gerpen |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0165328 A1 | 6/2013 | Previte et al. |
| 2013/0196864 A1 | 8/2013 | Govindarajan et al. |
| 2013/0217071 A1 | 8/2013 | Montesclaros et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0289246 A1 | 10/2013 | Crowe et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0221250 A1 | 8/2014 | Vasquez et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0119293 A1 | 4/2015 | Short |
| 2015/0120265 A1 | 4/2015 | Amirav-Drory et al. |
| 2015/0159152 A1 | 6/2015 | Allen et al. |
| 2015/0183853 A1 | 7/2015 | Sharma et al. |
| 2015/0191524 A1 | 7/2015 | Smith et al. |
| 2015/0191624 A1 | 7/2015 | Scheibel et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |

(56) References Cited

U.S. PATENT DOCUMENTS

| | | |
|---|---|---|
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090422 A1 | 3/2016 | Reif et al. |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai et al. |
| 2016/0253890 A1 | 9/2016 | Rabinowitz et al. |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0297883 A1 | 10/2016 | Gallo et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067047 A1 | 3/2017 | Link et al. |
| 2017/0067099 A1 | 3/2017 | Zheng et al. |
| 2017/0073664 A1 | 3/2017 | McCafferty et al. |
| 2017/0073731 A1 | 3/2017 | Zheng et al. |
| 2017/0081660 A1 | 3/2017 | Cox et al. |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0247473 A1 | 8/2017 | Short |
| 2017/0249345 A1 | 8/2017 | Malik et al. |
| 2017/0253644 A1 | 9/2017 | Steyaert et al. |
| 2017/0298432 A1 | 10/2017 | Holt |
| 2017/0320061 A1 | 11/2017 | Venter et al. |
| 2017/0327819 A1 | 11/2017 | Banyai et al. |
| 2017/0355984 A1 | 12/2017 | Evans et al. |
| 2017/0357752 A1 | 12/2017 | Diggans |
| 2017/0362589 A1 | 12/2017 | Banyai et al. |
| 2018/0029001 A1 | 2/2018 | Banyai et al. |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck et al. |
| 2018/0142289 A1 | 5/2018 | Zeitoun et al. |
| 2018/0171509 A1 | 6/2018 | Cox et al. |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0273936 A1 | 9/2018 | Cox et al. |
| 2018/0282721 A1 | 10/2018 | Cox et al. |
| 2018/0291445 A1 | 10/2018 | Betts et al. |
| 2018/0312834 A1 | 11/2018 | Cox et al. |
| 2018/0326388 A1 | 11/2018 | Banyai et al. |
| 2018/0334712 A1 | 11/2018 | Singer et al. |
| 2018/0346585 A1 | 12/2018 | Zhang et al. |
| 2018/0355351 A1 | 12/2018 | Nugent et al. |
| 2019/0060345 A1 | 2/2019 | Harrison et al. |
| 2019/0083596 A1 | 3/2019 | Orentas et al. |
| 2019/0118154 A1 | 4/2019 | Marsh et al. |
| 2019/0135926 A1 | 5/2019 | Glanville |
| 2019/0224711 A1 | 7/2019 | Demeris, Jr. |
| 2019/0240636 A1 | 8/2019 | Peck et al. |
| 2019/0244109 A1 | 8/2019 | Bramlett et al. |
| 2019/0314783 A1 | 10/2019 | Banyai et al. |
| 2019/0318132 A1 | 10/2019 | Peck |
| 2019/0352635 A1 | 11/2019 | Toro et al. |
| 2019/0366293 A1 | 12/2019 | Banyai et al. |
| 2019/0366294 A1 | 12/2019 | Banyai et al. |
| 2020/0017907 A1 | 1/2020 | Zeitoun et al. |
| 2020/0056229 A1 | 2/2020 | Mir |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |
| 2020/0325235 A1 | 10/2020 | Tabibiazar et al. |
| 2021/0002710 A1 | 1/2021 | Gantt et al. |
| 2021/0040476 A1 | 2/2021 | Cox et al. |
| 2021/0071168 A1 | 3/2021 | Nugent et al. |
| 2021/0102192 A1 | 4/2021 | Tabibiazar et al. |
| 2021/0102195 A1 | 4/2021 | Sato et al. |
| 2021/0102198 A1 | 4/2021 | Cox et al. |
| 2021/0115594 A1 | 4/2021 | Cox et al. |
| 2021/0129108 A1 | 5/2021 | Marsh et al. |
| 2021/0142182 A1 | 5/2021 | Bramlett et al. |
| 2021/0147830 A1 | 5/2021 | Liss |
| 2021/0170356 A1 | 6/2021 | Peck et al. |
| 2021/0179724 A1 | 6/2021 | Sato et al. |
| 2021/0207197 A1 | 7/2021 | Gantt et al. |
| 2021/0332078 A1 | 10/2021 | Wu |
| 2021/0348220 A1 | 11/2021 | Zeitoun et al. |
| 2021/0355194 A1 | 11/2021 | Sato et al. |
| 2021/0395344 A1 | 12/2021 | Sato et al. |
| 2022/0032256 A1 | 2/2022 | Lackey et al. |

(56) References Cited

U.S. PATENT DOCUMENTS

| | | |
|---|---|---|
| 2022/0064206 A1 | 3/2022 | Fernandez et al. |
| 2022/0064313 A1 | 3/2022 | Sato et al. |
| 2022/0064628 A1 | 3/2022 | Toro et al. |
| 2022/0106586 A1 | 4/2022 | Nugent et al. |
| 2022/0106590 A1 | 4/2022 | Arbiza et al. |
| 2022/0135690 A1 | 5/2022 | Sato et al. |
| 2022/0135965 A1 | 5/2022 | Gantt et al. |
| 2022/0145289 A1 | 5/2022 | Lackey et al. |
| 2022/0206001 A1 | 6/2022 | Sato |
| 2022/0243195 A1 | 8/2022 | Nugent et al. |
| 2022/0246236 A1 | 8/2022 | Amirav-Drory |
| 2022/0259319 A1 | 8/2022 | Sato et al. |
| 2022/0259638 A1 | 8/2022 | Brown |
| 2022/0277808 A1 | 9/2022 | Arbiza et al. |
| 2022/0281989 A1 | 9/2022 | Glanville |
| 2022/0307010 A1 | 9/2022 | Sato et al. |
| 2022/0315971 A1 | 10/2022 | Wu et al. |
| 2022/0323924 A1 | 10/2022 | Lackey et al. |
| 2022/0325276 A2 | 10/2022 | Banyai et al. |
| 2022/0325278 A1 | 10/2022 | Nugent et al. |
| 2022/0348659 A1 | 11/2022 | Sato et al. |
| 2022/0356463 A1 | 11/2022 | Shen et al. |
| 2022/0356468 A1 | 11/2022 | Sato et al. |
| 2022/0411784 A1 | 12/2022 | Sato et al. |
| 2023/0002478 A1 | 1/2023 | Sato et al. |

FOREIGN PATENT DOCUMENTS

| | | | |
|---|---|---|---|
| CA | 2720587 A1 * | 10/2009 | ........... A61K 47/545 |
| CN | 1771336 A | 5/2006 | |
| CN | 101277758 A | 10/2008 | |
| CN | 102159726 A | 8/2011 | |
| CN | 102460155 A | 5/2012 | |
| CN | 103003431 A | 3/2013 | |
| CN | 103907117 A | 7/2014 | |
| CN | 104520864 A | 4/2015 | |
| CN | 104562213 A | 4/2015 | |
| CN | 104734848 A | 6/2015 | |
| CN | 104974929 A | 10/2015 | |
| CN | 204714802 U | 10/2015 | |
| CN | 105119717 A | 12/2015 | |
| CN | 105358714 A | 2/2016 | |
| CN | 105593415 A | 5/2016 | |
| CN | 105637097 A | 6/2016 | |
| CN | 106222185 A | 12/2016 | |
| DE | 10260805 A1 | 7/2004 | |
| EA | 201890763 A1 | 8/2018 | |
| EP | 0090789 A1 | 10/1983 | |
| EP | 0126621 B1 | 8/1990 | |
| EP | 0753057 A1 | 1/1997 | |
| EP | 1314783 A1 | 5/2003 | |
| EP | 1363125 A2 | 11/2003 | |
| EP | 1546387 A2 | 6/2005 | |
| EP | 1153127 B1 | 7/2006 | |
| EP | 1728860 A1 | 12/2006 | |
| EP | 1072010 B1 | 4/2010 | |
| EP | 2175021 A2 | 4/2010 | |
| EP | 2330216 A1 | 6/2011 | |
| EP | 1343802 B1 | 5/2012 | |
| EP | 2504449 A1 | 10/2012 | |
| EP | 2751729 A1 | 7/2014 | |
| EP | 2872629 A1 | 5/2015 | |
| EP | 2928500 A1 | 10/2015 | |
| EP | 2971034 A1 | 1/2016 | |
| EP | 3030682 A2 | 6/2016 | |
| EP | 3044228 A4 | 4/2017 | |
| EP | 2994509 B1 | 6/2017 | |
| EP | 3204518 A1 | 8/2017 | |
| JP | H07505530 A | 6/1995 | |
| JP | 2001518086 A | 10/2001 | |
| JP | 2002511276 A | 4/2002 | |
| JP | 2002536977 A | 11/2002 | |
| JP | 2002538790 A | 11/2002 | |
| JP | 2003522119 A | 7/2003 | |
| JP | 2004521628 A | 7/2004 | |
| JP | 2004268394 A | 9/2004 | |
| JP | 2006503586 A | 2/2006 | |
| JP | 2006238724 A | 9/2006 | |
| JP | 2007314746 A | 12/2007 | |
| JP | 2008505642 A | 2/2008 | |
| JP | 2008097189 A | 4/2008 | |
| JP | 2008523786 A | 7/2008 | |
| JP | 2008214343 A | 9/2008 | |
| JP | 2009294195 A | 12/2009 | |
| JP | 2010248084 A | 11/2010 | |
| JP | 2012507513 A | 3/2012 | |
| JP | 2015521472 A * | 7/2015 | |
| JP | 2016527313 A | 9/2016 | |
| KR | 101339064 B1 * | 1/2014 | |
| WO | WO-9015070 A1 | 12/1990 | |
| WO | WO-9210092 A1 | 6/1992 | |
| WO | WO-9210588 A1 | 6/1992 | |
| WO | WO-9309668 A1 | 5/1993 | |
| WO | WO-9320242 A1 | 10/1993 | |
| WO | WO-9525116 A1 | 9/1995 | |
| WO | WO-9526397 A1 | 10/1995 | |
| WO | WO-9615861 A1 | 5/1996 | |
| WO | WO-9710365 A1 | 3/1997 | |
| WO | 9747967 A1 | 12/1997 | |
| WO | WO-9822541 A2 | 5/1998 | |
| WO | WO-9841531 A2 | 9/1998 | |
| WO | WO-9942813 A1 | 8/1999 | |
| WO | WO-9953101 A1 | 10/1999 | |
| WO | WO-0013017 A2 | 3/2000 | |
| WO | WO-0018957 A1 | 4/2000 | |
| WO | WO-0042559 A1 | 7/2000 | |
| WO | WO-0042560 A2 | 7/2000 | |
| WO | WO-0042561 A2 | 7/2000 | |
| WO | WO-0049142 A1 | 8/2000 | |
| WO | WO-0053617 A1 | 9/2000 | |
| WO | WO-0156216 A2 | 8/2001 | |
| WO | WO-0210443 A1 | 2/2002 | |
| WO | WO-0156216 A3 | 3/2002 | |
| WO | WO-0220537 A2 | 3/2002 | |
| WO | WO-0224597 A2 | 3/2002 | |
| WO | 0233669 A1 | 4/2002 | |
| WO | WO-0227638 A1 | 4/2002 | |
| WO | WO-02072791 A2 | 9/2002 | |
| WO | WO-02072864 A2 | 9/2002 | |
| WO | WO-03040410 A1 | 5/2003 | |
| WO | WO-03046223 A1 | 6/2003 | |
| WO | WO-03054232 A2 | 7/2003 | |
| WO | WO-03060084 A2 | 7/2003 | |
| WO | WO-03064026 A1 | 8/2003 | |
| WO | WO-03064027 A2 | 8/2003 | |
| WO | WO-03064699 A2 | 8/2003 | |
| WO | WO-03065038 A2 | 8/2003 | |
| WO | WO-03066212 A2 | 8/2003 | |
| WO | WO-03089605 A2 | 10/2003 | |
| WO | WO-03093504 A1 | 11/2003 | |
| WO | WO-03100012 A2 | 12/2003 | |
| WO | WO-2004024886 A2 | 3/2004 | |
| WO | WO-2004029220 A2 | 4/2004 | |
| WO | WO-2004029586 A1 | 4/2004 | |
| WO | WO-2004031351 A2 | 4/2004 | |
| WO | WO-2004031399 A2 | 4/2004 | |
| WO | WO-2004039953 A2 | 5/2004 | |
| WO | WO-2004059556 A2 | 7/2004 | |
| WO | WO-03060084 A3 | 8/2004 | |
| WO | WO-2005014850 A2 | 2/2005 | |
| WO | WO-2005051970 A2 | 6/2005 | |
| WO | WO-2005059096 A2 | 6/2005 | |
| WO | WO-2005059097 A2 | 6/2005 | |
| WO | WO-2005093092 A2 | 10/2005 | |
| WO | WO-2006023144 | 3/2006 | |
| WO | WO-2006044956 A1 | 4/2006 | |
| WO | WO-2006076679 A1 | 7/2006 | |
| WO | WO-2006116476 A1 | 11/2006 | |
| WO | WO-2007073171 A2 | 6/2007 | |
| WO | WO-2007109221 A2 | 9/2007 | |
| WO | WO-2007118214 A2 | 10/2007 | |
| WO | WO-2007120627 A2 | 10/2007 | |
| WO | WO-2007137242 A2 | 11/2007 | |
| WO | WO-2008003116 A2 | 1/2008 | |

(56) References Cited

FOREIGN PATENT DOCUMENTS

| | | |
|---|---|---|
| WO | WO-2008006078 A2 | 1/2008 |
| WO | WO-2008027558 A2 | 3/2008 |
| WO | WO-2008045380 | 4/2008 |
| WO | WO-2008054543 A2 | 5/2008 |
| WO | WO-2008063134 A1 | 5/2008 |
| WO | WO-2008063135 A1 | 5/2008 |
| WO | WO-2008068280 A1 | 6/2008 |
| WO | WO-2008103474 A1 | 8/2008 |
| WO | WO-2008109176 A2 | 9/2008 |
| WO | WO-2009132876 A1 | 11/2009 |
| WO | WO-2009126290 A3 | 12/2009 |
| WO | WO-2010001251 A2 | 1/2010 |
| WO | WO-2010025310 A2 | 3/2010 |
| WO | WO-2010025566 A1 | 3/2010 |
| WO | WO-2010027512 A2 | 3/2010 |
| WO | WO-2010053443 A1 | 5/2010 |
| WO | WO-2010089412 A1 | 8/2010 |
| WO | WO-2010141249 A2 | 12/2010 |
| WO | WO-2010141433 A2 | 12/2010 |
| WO | WO-2011020529 A2 | 2/2011 |
| WO | WO-2010141433 A3 | 4/2011 |
| WO | WO-2011053957 A2 | 5/2011 |
| WO | WO-2011056644 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013010062 A2 | 1/2013 |
| WO | WO-2013030827 A1 | 3/2013 |
| WO | WO-2013032850 A2 | 3/2013 |
| WO | WO-2013036668 A1 | 3/2013 |
| WO | WO-2013049227 A2 | 4/2013 |
| WO | WO-2013101896 A1 | 7/2013 |
| WO | WO-2013134881 A1 | 9/2013 |
| WO | WO-2013154770 A1 | 10/2013 |
| WO | WO-2013170168 A1 | 11/2013 |
| WO | WO-2013177220 A1 | 11/2013 |
| WO | WO-2014004393 A1 | 1/2014 |
| WO | WO-2014008447 A1 | 1/2014 |
| WO | WO-2014021938 A1 | 2/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015081440 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | 2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018119246 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018170559 A1 | 9/2018 |
| WO | WO-2018200380 A1 | 11/2018 |
| WO | WO-2018231872 A1 | 12/2018 |
| WO | WO-2019014781 A1 | 1/2019 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |
| WO | WO-2020257612 A1 | 12/2020 |
| WO | WO-2021046655 A1 | 3/2021 |
| WO | WO-2021119193 A2 | 6/2021 |
| WO | WO-2022010934 A2 | 1/2022 |
| WO | WO-2022046797 A1 | 3/2022 |
| WO | WO-2022046944 A2 | 3/2022 |
| WO | WO-2022047076 A1 | 3/2022 |
| WO | WO-2022076326 A1 | 4/2022 |
| WO | WO-2022086866 A1 | 4/2022 |
| WO | WO-2022087293 A1 | 4/2022 |
| WO | WO-2022098662 A2 | 5/2022 |
| WO | WO-2022159620 A1 | 7/2022 |
| WO | WO-2022178137 A1 | 8/2022 |
| WO | WO-2022204309 A1 | 9/2022 |
| WO | WO-2022204316 A2 | 9/2022 |
| WO | WO-2022217004 A1 | 10/2022 |
| WO | WO-2022235579 A1 | 11/2022 |
| WO | WO-2022235584 A1 | 11/2022 |
| WO | WO-2022271884 A2 | 12/2022 |

OTHER PUBLICATIONS

Acevedo-Rocha et al.: Directed evolution of stereoselective enzymes based on genetic selection as opposed to screening systems. J. Biotechnol. 191:3-10 (2014).

Adessi et al.: Solid phase DNA amplification: characterisation of primer attachment and amplification mechanisms. Nucleic Acids Res. 28(20):E87, 2000.

Agbavwe et al.: Efficiency, Error and Yield in Light-Directed Maskless Synthesis of DNA Microarrays. Journal of Nanobiotechnology. 9(57):1-17 (2011).

(56) References Cited

OTHER PUBLICATIONS

Alberts et al.: Molecular Biology of the Cell. 4th edition. New York: Garland Science; 2002. The Generation of Antibody Diversity. https://www.ncbi.nlm.nih.gov/books/NBK26860/.
Alexeyev et al.: Gene synthesis, bacterial expression and purification of the Rickettsia prowazekii ATP/ADP translocase, Biochimica et Biophysics Acta, 1419:299-306, 1999.
Al-Housseiny et al.: Control of interfacial instabilities using flow geometry Nature Physics, 8:747-750, 2012.
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Altshuler et al.: Generation of Recombinant Antibodies and Means for Increasing Their Affinity. Biochemistry (Moscow). 75(13:1584-1605 (2010).
Amblard et al.: A magnetic manipulator for studying local rheology and micromechanical properties of biological systems, Rev. Sci. Instrum., 67(3):18-827, 1996.
Andoni and Indyk. Near-Optimal Hashing Algorithms for Approximate Nearest Neighbor in High Dimensions, Communications of the ACM, 51(1):117-122, 2008.
Arand et al.: Structure of Rhodococcus erythropolis limonene-1,2-epoxide hydrolase reveals a novel active site. EMBO J. 22:2583-2592 (2003).
Arkles et al.: The Role of Polarity in the Structure of Silanes Employed in Surface Modification. Silanes and Other Coupling Agents. 5:51-64, 2009.
Arkles. Hydrophobicity, Hydrophilicity Reprinted with permission from the Oct. 2006 issue of Paint & Coatings Industry magazine, Retrieved on Mar. 19, 2016, 10 pages.
Assembly manual for the POSaM: The ISB Piezoelectric Oligonucleotide Synthesizer and Microarrayer, The Institute for Systems Biology, May 28, 2004 (50 pages).
Assi et al.: Massive-parallel adhesion and reactivity—measurements using simple and inexpensive magnetic tweezers. J. Appl. Phys. 92(9):5584-5586 (2002).
ATDBio. Nucleic Acid Structure, Nucleic Acids Book, 9 pages, published on Jan. 22, 2005. from: http://www.atdbio.com/content/5/Nucleic-acid-structure.
ATDBio. Solid-Phase Oligonucleotide Synthesis, Nucleic Acids Book, 20 pages, Published on Jul. 31, 2011. from: http://www.atdbio.com/content/17/Solid-phase-oligonucleotide-synthesis.
Au et al.: Gene synthesis by a LCR-based approach: high level production of Leptin-L54 using synthetic gene in *Escherichia coli*. Biochemical and Biophysical Research Communications 248:200-203 (1998).
Baedeker et al.: Overexpression of a designed 2.2kb gene of eukaryotic phenylalanine ammonialyase in *Escherichia coli*•. FEBS Letters, 457:57-60, 1999.
Bai. A Novel Human scFv Library with Non-Combinatorial Synthetic CDR Diversity. PLoS One. 10(10):1-18 (2015).
Barbee et al.: Magnetic Assembly of High-Density DNA Arrays for Genomic Analyses. Anal Chem. 80(6):2149-2154, 2008.
Barton et al.: A desk electrohydrodynamic jet printing system. Mechatronics, 20:611-616, 2010.
Beaucage et al.: Advances in the synthesis of oligonucleotides by the phosphoramidite approach. Tetrahedron. 48:2223-2311, 1992.
Beaucage et al.: Deoxynucleoside phosphoramidites—A new class of key intermediates for deoxypolynucleotide synthesis. Tetrahedron Lett. 22(20):1859-1862, 1981.
Beaucage et al.: The Chemical synthesis of DNA/RNA Chapter 2 in: Encyclopedia of Cell Biology, 1:36-53, 2016.
Beaulieu et al.: PCR candidate region mismatch scanning adaptation to quantitative, high-throughput genotyping, Nucleic Acids Research, 29(5):1114-1124, 2001.
Beigelman et al.: Base-modified phosphoramidite analogs of pyrimidine ribonucleosides for RNA structure-activity studies. Methods Enzymol. 317:39-65, 2000.
Berg: Biochemistry. 5th Ed. New York (2002) 148-149.

Bethge et al.: Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%2001igonucleotides%20%2864-108%29.pdf.
Binkowski et al.: Correcting errors in synthetic DNA through consensus shuffling. Nucleic Acids Research, 33(6): e55, 8 pages, 2005.
Biswas et al.: Identification and characterization of a thermostable MutS homolog from Thennus aquaticus, The Journal of Biological Chemistry, 271(9):5040-5048, 1996.
Biswas et al.: Interaction of MutS protein with the major and minor grooves of a heteroduplex DNA, The Journal of Biological Chemistry, 272(20):13355-13364, 1997.
Bjornson et al.: Differential and simultaneous adenosine Di- and Triphosphate binding by MutS, The Journal of Biological Chemistry, 278(20):18557-18562, 2003.
Blanchard et al.: High-Density Oligonucleotide Arrays, Biosensors & Bioelectronics, 11(6/7):687-690, 1996.
Blanchard: Genetic Engineering, Principles and Methods, vol. 20, Ed. J. Sedlow, New York: Plenum Press, p. 111-124, 1979.
Blawat et al.: Forward error correction for DNA data storage. Procedia Computer Science, 80:1011-1022, 2016.
Bonini and Mondino. Adoptive T-cell therapy for cancer: The era of engineered T cells. European Journal of Immunology, 45:2457-2469 (2015).
Borda et al.: Secret writing by DNA hybridization. Acta Technica Napocensis Electronics and Telecommunications. 50(2):21-24 (2009).
Bornholt et al.: A DNA-Based Archival Storage System, in International Conference on Architectural Support for Programming Languages and Operating Systems (ASPLOS), Apr. 2-6, 2016, Atlanta, GA, 2016, 637-649.
Borovkov et al.: High-quality gene assembly directly from unpurified mixtures of microassay-synthesized oligonucleotides. Nucleic Acid Research, 38(19):e180, 10 pages, 2010.
Brunet: Aims and methods of biosteganography. Journal of Biotechnology, 226:56-64, 2016.
Buermans et al.: Next Generation sequencing technology: Advances and applications, Biochimica et Biophysica Acta (BBA)—Molecular Basis of Disease, 1842:1931-1941, 2014.
Butler et al.: In situ synthesis of oligonucleotide arrays by using surface tension. J Am Chem Soc. 123(37):8887-94, 2001.
Calvert. Lithographically patterned self-assembled films. In: Organic Thin Films and Surfaces: Directions for the Nineties, vol. 20, p. 109, ed. by Abraham Ulman, San Diego: Academic Press, 1995.
Cardelli. Two-Domain DNA Strand Displacement, Electron. Proc. Theor. Comput. Sci., 26:47-61, 2010.
Carlson. Time for New DNA Synthesis and Sequencing Cost Curves, 2014. [Online]. Available: http://www.synthesis.cc/synthesis/2014/02/time_for_new_cost_curves_2014. 10 pages.
Carr et al.: Protein-mediated error correction for de novo DNA synthesis. Nucleic Acids Res. 32(20):e162, 9 pages, 2004.
Carter and Friedman. DNA synthesis and Biosecurity: Lessons learned and options for the future. J. Craig Venter Institute, La Jolla, CA, 28 pages, Oct. 2015.
Caruthers. Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers. The Chemical Synthesis of DNA/RNA: Our Gift to Science. J. Biol. Chem., 288(2):1420-1427, 2013.
Casmiro et al.: PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello et al.: Chemical synthesis of poliovirus cDNA: generation of infectious virus in the absence of natural template. Science. 297(5583):1016-8, 2000.
Chalmers et al.: Scaling up the ligase chain reaction-based approach to gene synthesis. Biotechniques. 30(2):249-52, 2001.
Chan et al.: Natural and engineered nicking endonucleases—from cleavage mechanism to engineering of strand-specificity. Nucleic Acids Res. 39(1):1-18, 2011.

(56) References Cited

OTHER PUBLICATIONS

Chen et al.: Chemical modification of gene silencing oligonucleotides for drug discovery and development. Drug Discov Today. 10(8):587-93 2005.
Chen et al.: Programmable chemical controllers made from DNA, Nat. Nanotechnol., 8(10):755-762, 2013.
Cheng et al.: High throughput parallel synthesis of oligonucleotides with 1536 channel synthesizer. Nucleic Acids Res. 30(18):e93, 2002.
Chervin et al.: Design of T-cell receptor libraries with diverse binding properties to examine adoptive T-cell responses. Gene Therapy. 20(6):634-644 (2012).
Chilamakuri et al.: Performance comparison of four exome capture systems for deep sequencing. BMC Genomics 15(1):449 (2014).
Cho et al.: Capillary passive valve in microfluidic systems. NSTI-Nanotech. 2004; 1:263-266.
Chrisey et al.: Fabrication of patterned DNA surfaces Nucleic Acids Research, 24(15):3040-3047 (1996).
Chung et al.: One-step preparation of competent *Escherichia coli*: Transformation and storage of bacterial cells in the same solution. Proc Natl Acad Sci U S A. Apr. 1989;86(7):2172-2175.
Church et al.: Next-generation digital information storage in DNA. Science, 337:6102, 1628-1629, 2012.
Cleary et al.: Production of complex nucleic acid libraries using highly parallel in situ oligonucleotide synthesis. Nat Methods 1(3):241-248 (2004).
Cohen et al.: Human population: The next half century. Science, 302:1172-1175, 2003.
Crick. On protein synthesis. Symp Soc Exp Biol12:138-163, 1958.
Cruse et al.: Atlas of Immunology, Third Edition. Boca Raton:CRC Press (pp. 282-283) (2010).
Cui et al.: Information Security Technology Based on DNA Computing. International Workshop on Anti-Counterfeiting, Security and Identification (ASID); IEEE Xplore 4 pages (2007).
Cutler et al.: High-throughput variation detection and genotyping using microarrays, Genome Research, vol. 11, 1913-19 (2001).
Dahl et al.: Circle-to-circle amplification for precise and sensitive DNA analysis. Proc Natl Acad Sci U S A. Mar. 30, 2004;101(13):4548-53. Epub Mar. 15, 2004.
Damha et al.: An improved procedure for derivatization of controlled-pore glass beads for solid-phase oligonucleotide synthesis. Nucleic Acids Research. 18(13):3813-3821 (1990).
De Graff et al.: Glucagon-Like Peptide-1 and its Class B G Protein-Coupled Receptors: A Long March to Therapeutic Successes. Pharmacol Rev. 68(4):954-1013 (2016).
De Mesmaeker et al.: Backbone modifications in oligonucleotides and peptide nucleic acid systems. Curr Opin Struct Biol. Jun. 1995;5(3):343-55.
De Silva et al.: New Trends of Digital Data Storage in DNA. BioMed Res Int. 2016:8072463 (2016).
Deamer et al.: Characterization of nucleic acids by nanopore analysis, Ace. Cham. Res., vol. 35, No. 10, 817-825 (2002).
Deaven. The Human Genome Project: Recombinant clones for mapping and sequencing DNA. Los Alamos Science, 20:218-249, 1992.
Deng et al.: Targeted bisulfite sequencing reveals changes in DNA methylation associated with nuclear reprogramming Nature Biotechnology, 27:352-360 (2009).
Diehl et al.: BEAMING: single-molecule PCR on microparticles in water-in-oil emulsions. Nature Methods. 3(7):551-559 (2006).
Dietrich et al.: Gene assembly based on blunt-ended double-stranded DNA-modules, Biotechnology Techniques, vol. 12, No. 1, 49-54 (Jan. 1998).
Dillon et al.: Exome sequencing has higher diagnostic yield compared to simulated disease-specific panels in children with suspected monogenic disorders. Eur J Hum Genet 26(5):644-651 (2018).
Dormitzer et al.: Synthetic generation of influenza vaccine viruses for rapid response to pandemics. Sci Translational Medicine, 5(185):185ra68, 14 pages, 2013.
Doudna et al.: Genome editing. The new frontier of genome engineering with CRISPR-Cas9. Science 346(6213):1258096-1-1258096-9, 2014.
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Dower et al.: High efficiency transformation of *E.coli* by high voltage electroporation. Nucleic Acids Res. 16(13):6127-45 (1988).
Dressman et al.: Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac et al.: Human genome sequencing using unchained base reads on self-assembling DNA nanoarrays. Science. Jan. 1, 2010;327(5961):78-81. doi: 10.1126/science. 1181498. Epub Nov. 5, 2009.
Droege and Hill. The Genome Sequencer FLXTM System-Longer reads, more applications, straight forward bioinformatics and more complete data sets Journal of Biotechnology, 136:3-10, 2008.
Duffy et al.: Rapid Prototyping of Microfluidic Systems in Poly(dimethylsiloxane). Anal Chem. Dec. 1, 1998;70(23):4974-84. doi: 10.1021/ac980656z.
Duggan et al.: Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie et al.: Guanine modification during chemical DNA synthesis. Nucleic Acids Res. Oct. 26, 1987;15(20):8333-49.
Eisen. A phylogenomic study of the MutS family of proteins, Nucleic Acids Research, vol. 26, No. 18, 4291-4300 (1998).
Ellis et al.: DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer et al.: Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al.: The Genome sequence of taurine cattle: A window of ruminant biology and evolution. Science, 324:522-528, 2009.
Elsner et al.: 172 nm excimer VUV-triggered photodegradation and micropatterning of aminosilane films, Thin Solid Films, 517:6772-6776 (2009).
Engler et al.: A one pot, one step, precision cloning method with high throughput capability. PLoS One. 2008;3(11):e3647. doi: 10.1371/journal.pone.0003647. Epub Nov. 5, 2008.
Engler et al.: Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski. DNA fountain enables a robust and efficient storage architecture. Science, 355(6328):950-054, 2017.
Eroshenko et al.: Gene Assembly from Chip-Synthesized Oligonucleotides; Current Protocols in Chemical biology 4: 1-17 (2012).
Evans et al.: DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy et al.: Self-sustained sequence replication (3SR): an isothermal transcription-based amplification system alternative to PCR. PCR Methods Appl. Aug. 1991;1(1):25-33.
Fedoryak et al.: Brominated hydroxyquinoline as a photolabile protecting group with sensitivity to multiphoton excitation, Org. Lett., vol. 4, No. 2, 3419-3422 (2002).
Fernández-Quintero et al.: Characterizing the Diversity of the CDR-H3 Loop Conformational Ensembles in Relationship to Antibody Binding Properties. Front. Immunol. 9:1-11 (2019).
Ferretti et al.: Total synthesis of a gene for bovine rhodopsin. PNAS, 83:599-603 (1986).
Finger et al.: The wonders of Flap Endonucleases: Structure, function, mechanism and regulation. Subcell Biochem., 62:301-326, 2012.

(56) References Cited

OTHER PUBLICATIONS

Fodor et al.: Light-directed, spatially addressable parallel chemical synthesis. Science. 251(4995):767-773 (1991).
Fogg et al.: Structural basis for uracil recognition by archaeal family B Dna polymerases. Nature Structural Biology, 9(12):922-927, 2002.
Foldesi et al.: The synthesis of deuterionucleosides. Nucleosides Nucleotides Nucleic Acids. Oct.-Dec. 2000;19(10-12):1615-56.
Frandsen et al.: Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al.: Next-generation DNA sequencing of paired-end tags [PET] for transcriptome and genome analysis Genome Research, 19:521-532, 2009.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
Galneder et al.: Microelectrophoresis of a bilayer-coated silica bead in an optical trap: application to enzymology. Biophysical Journal, vol. 80, No. 5, 2298-2309 (May 2001).
Gao et al.: A flexible light-directed DNA chip synthesis gated by deprotection using solution photogenerated acids. Nucleic Acids Res. Nov. 15, 2001;29(22):4744-50.
Gao et al.: A method for the generation of combinatorial antibody libraries using pIX phage display. PNAS 99(20):12612-12616 (2002).
Gao et al.: Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj et al.: Graphene as a subnanometre trans-electrode membrane. Nature. Sep. 9, 2010;467(7312):190-3. doi: 10.1038/nature09379.
Garbow et al.: Optical tweezing electrophoresis of isolated, highly charged colloidal spheres, Colloids and Surfaces A: Physiochem. Eng. Aspects, vol. 195, 227-241 (2001).
GE Healthcare. AKTA oligopilot plus. Data File 18-114-66 ADC. 8 pages (2006).
GE Healthcare. Robust and cost-efficient oligonucleotide synthesis. Application Note 28-4058-08 AA. 4 pages (2005).
Geetha et al.: Survey on Security Mechanisms for Public Cloud Data. 2016 International Conference on Emerging Trends in Engineering, Technology and Science (ICETETS). 8 pages (2016).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores et al.: USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson et al.: Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al.: Creation of a Bacterial Cell Controlled by a Chemically Synthesized Genome. Science 329(5989):52-56 (2010).
Goldfeder et al.: Medical implications of technical accuracy in genome sequencing. Genome Med 8(1):24 (2016).
Goldman et al.: Towards practical, high-capacity, low-maintenance information storage in synthesized DNA, Nature, 494(7435):77-80, 2013.
Goodwin et al.: immunoglobulin heavy chain variable region, partial [*Homo sapiens*]. Genbank entry (online). National Institute of Biotechnology Information. (2018) https://www.ncbi.nim.nih.gov/protein/AXA12486.1.
Gosse et al.: Magnetic tweezers: micromanipulation and force measurement at the molecular level, Biophysical Journal, vol. 8, 3314-3329 (Jun. 2002).
Grass et al.: Robust chemical preservation of digital information on DNA in silica with error-correcting codes, Angew. Chemie—Int. Ed., 54(8):2552-2555, 2015.
Greagg et al.: A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al.: Depletion of abundant sequences by hybridization (DASH): using Cas9 to remove unwanted high-abundance species in sequencing libraries and molecular counting applications. Genome Biology, 17:41, 13 pages, 2016.
Haber et al.: Magnetic tweezers for DNA micromanipulation, Rev. Sci. Instrum., vol. 71, No. 12, 4561-4570 (Dec. 2000).
Han et al.: Linking T-cell receptor sequence to functional phenotype at the single-cell level. Nat Biotechnol 32(7):684-692 (2014).
Hanahan and Cold Spring Harbor Laboratory. Studies on transformation of *Escherichia coli* with plasmids J. Mol. Biol. 166:557-580 (1983).
Hanahan et al.: Plasmid transformation of *Escherichia coli* and other bacteria. Methods Enzymol, vol. 204, p. 63-113 (1991).
Harada et al.: Unexpected substrate specificity of T4 DNA ligase revealed by in vitro selection. Nucleic Acids Res. May 25, 1993;21(10):2287-91.
Hauser et al.: Trends in GPCR drug discovery: new agents, targets and indications. Nature Reviews Drug Discovery, 16, 829-842 (2017). doi:10.1038/nrd.2017.178 https://www.nature.com/articles/nrd.2017.178.
Heckers et al.: Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hood et al.: The digital code of DNA. Nature 421.6921:444-448 (2003).
Hoover et al.: DNAWorks: an automated method for designing oligonucleotides for PCR-based gene synthesis, Nucleic Acids Research, vol. 30, No. 10, e43, 7 pages (2002).
Hopcroft et al.: What is the Young's Modulus of Silicon?. Journal of Microelectromechanical Systems. 19(2):229-238 (2010).
Hosu et al.: Magnetic tweezers for intracellular applications., Rev. Sci. Instrum., vol. 74, No. 9, 4158-4163 (Sep. 2003).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Huang et al.: Three-dimensional cellular deformation analysis with a two-photon magnetic manipulator workstation, Biophysical Journal, vol. 82, No. 4, 2211-2223 (Apr. 2002).
Hudson: Matrix Assisted Synthetic Transformations: A Mosaic of Diverse Contributions. Journal of Combinatorial Chemistry. 1(6):403-457 (1999).
Hughes et al.: Expression profiling using microarrays fabricated by an ink-jet oligonucleotide synthesizer Nat Biotech 4:342-347 (2001).
Hughes et al.: Principles of early drug discovery. Br J Pharmacol 162(2):1239-1249, 2011.
Hutchison et al.: Cell-free cloning using phi29 DNA polymerase. Proc Natl Acad Sci U S A. Nov. 29, 2005;102(48):17332-6. Epub Nov. 14, 2005.
Imgur: The magic of the internet. Uploaded May 10, 2012, 2 pages, retrieved from: https://imgur.com/mEWuW.

(56) References Cited

OTHER PUBLICATIONS

In-Fusion Cloning: Accuracy, Not Background. Cloning & Competent Cells, ClonTech Laboratories, 3 pages, available online Jul. 6, 2014.
Jackson et al.: Recognition of DNA base mismatches by a rhodium intercalator, J. Am. Chem. Soc., vol. 19, 12986-12987 (1997).
Jacobs et al. DNA glycosylases: In DNA repair and beyond. Chromosoma 121:1-20 (2012)—http://www.ncbi.nlm.nih.gov/pmc/articles/PMC3260424/.
Jacobus et al.: Optimal cloning of PCR fragments by homologous recombination in *Escherichia soli*. PLoS One 10(3):e0119221 (2015).
Jager et al.: Simultaneous Humoral and Cellular: Immune Response against Cancer—Testis Antigen NY-ES0-1: Definition of Human Histocompatibility Leukocyte Antigen (HLA)-A2-binding Peptide Epitopes. J. Exp. Med. 187(2):265-270 (1998).
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
Jang et al.: Characterization of T cell repertoire of blood, tumor, and ascites in ovarian cancer patients using next generation sequencing. Oncoimmunology, 4(11):e1030561:1-10 (2015).
Jinek et al.: A Programmable dual-RNA-guided DNA endonuclease in adaptive bacterial immunity. Science, 337:816-821, 2012.
Kalva et al.: Gibson Deletion: a novel application of isothermal in vitro recombination. Biological Procedures Online. 20(1):1-10 (2018).
Karagiannis and El-Osta. RNA interference and potential therapeutic applications of short interfering RNAs Cancer Gene Therapy, 12:787-795, 2005.
Ke et al.: Influence of neighboring base pairs on the stability of single base bulges and base pairs in a DNA fragment, Biochemistry, Vo. 34, 4593-4600 (1995).
Kelley et al.: Single-base mismatch detection based on charge transduction through DNA, Nucleic Acids Research, vol. 27, No. 24, 4830-4837 (1999).
Kim et al.: Chimeric restriction endonuclease, Proc. Natl. Acad. Sci. USA, vol. 91, 883-887 (Feb. 1994).
Kim et al.: High-resolution patterns of quantum dots formed by electrohydrodynamic jet printing for light-emitting diodes. Nano Letters, 15:969-973, 2015.
Kim et al.: Site-specific cleavage of DNA-RNA hybrids by zinc finger/Fok I cleavage domain fusions Gene, vol. 203, 43-49 (1997).
Kim. The interaction between Z-ONA and the Zab domain of double-stranded RNA adenosine deaminase characterized using fusion nucleases, The Journal of Biological Chemistry, vol. 274, No. 27, 19081-19086 (1999).
Kinde et al.: Detection and quantification of rare mutations with massively parallel sequencing. Proc Natl Acad Sci U S A. Jun. 7, 2011;108(23):9530-5. Epub May 17, 2011.
Kodumal et al.: Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al.: Genome-wide recessive genetic screening in mammalian cells with a lentiviral CRISPR-guide RNA library. Nature Biotechnology, 32:267-273, 2014 (with three pages of supplemental Online Methods).
Kong et al.: Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp et al.: Chemical amplification: continuous-flow PCR on a chip, Science, vol. 280, 1046-1048 (May 15, 1998).
Kosuri and Church. Large-scale de novo DNA synthesis: technologies and applications, Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.
Kosuri et al.: A scalable gene synthesis platform using high-fidelity DNA microchips Nat.Biotechnol. 28(12):1295-1299 (2010).
Krayden, Inc .: A Guide to Silane Solutions. Silane coupling agents. 7 pages. Published on May 31, 2005 at: http://krayden.com/pdf/xia_silane_chemistry.pdf.
Lagally et al.: Single-Molecule DNA Amplification and Analysis in an Integrated Microfluidic Device. Analytical Chemistry. 2001;73(3):565-570.
Lahue et al.: DNA mismatch correction in a defined system, Science, vol. 425; No. 4914, 160-164 (Jul. 14, 1989).
Lambrinakos et al.: Reactivity of potassium permanganate and tetraethylammonium chloride with mismatched bases and a simple mutation detection protocol. Nucleic Acids Research, vol. 27, No. 8, 1866-1874 (1999).
Landegren et al.: A ligase-mediated gene detection technique. Science. Aug. 26, 1988;241(4869):1077-80.
Lang et al.: An automated two-dimensional optical force clamp for single molecule studies, Biophysical Journal, vol. 83, 491-501 (Jul. 2002).
Lashkari et al.: An automated multiplex oligonucleotide synthesizer: development of high-throughput, low-cost DNA synthesis. Proc Natl Acad Sci U S A. Aug. 15, 1995;92(17):7912-5.
Lausted et al.: POSaM: a fast, flexible, open-source, inkjet oligonucleotide synthesizer and microarrayer, Genome Biology, 5:R58.
Leamon et al.: A massively parallel PicoTiterPlate based platform for discrete picoliter-scale polymerase chain reactions. Electrophoresis. Nov. 2003;24(21):3769-77.
Lebl et al.: Economical Parallel Oligonucleotide and Peptide Synthesizer—Pet Oligator. Int. J. Peptide Res. Ther. 13(1-2):367-376 (2007).
Lee et al.: A microfluidic oligonucleotide synthesizer. Nucleic Acids Research 2010 vol. 38(8):2514-2521. DOI: 10.1093/nar/gkq092.
Lee et al.: Microelectromagnets for the control of magnetic nanoparticles, Appl. Phys. Lett., vol. 79, No. 20, 3308-3310 (Nov. 12, 2001).
Lee: Covalent End-Immobilization of Oligonucleotides onto Solid Surfaces; Thesis, Massachusetts Institute of Technology, Aug. 2001 (315 pages).
Leproust et al.: Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust et al.: Synthesis of high-quality libraries of long (150mer) oligonucleotides by a novel depurination controlled process. Nucleic Acids Research. 2010; 38(8):2522-2540.
Lesnikowski et al.: Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene et al.: Zero-mode waveguides for single-molecule analysis at high concentrations. Science. Jan. 31, 2003;299(5607):682-6.
Lewontin and Harti. Population genetics in forensic DNA typing. Science, 254:1745-1750, 1991.
Li et al.: Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Li et al.: Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.

(56) References Cited

OTHER PUBLICATIONS

Limbachiya et al.: Natural data storage: A review on sending information from now to then via Nature. ACM Journal on Emerging Technologies in Computing Systems, V(N): Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz et al.: High density synthetic oligonucleotide arrays, Nature Genetics Supplement, vol. 21, 20-24 (Jan. 1999).
Lishanski et al.: Mutation detection by mismatch binding protein, MutS, in amplified DNA: application to the cystic fibrosis gene, Proc. Natl. Acad. Sci. USA, vol. 91, 2674-2678 (Mar. 1994).
Liu et al.: Comparison of Next-Generation Sequencing Systems. J Biomed Biotechnol 2012: 251364 (2012).
Liu et al.: Enhanced Signals and Fast Nucleic Acid Hybridization by Microfluidic Chaotic Mixing. Angew. Chem. Int. Ed. 2006; 45:3618-3623.
Liu et al.: Rational design of CXCR4 specific antibodies with elongated CDRs. JACS, 136:10557-10560, 2014.
Lizardi et al.: Mutation detection and single-molecule counting using isothermal rolling-circle amplification. Nat Genet. Jul. 1998;19(3):225-32.
Li et al.: Functional domains in Fok I restriction endonuclease, Proc. Natl. Acad. Sci. USA, 89:4275-4279, 1992.
Lu et al.: Methyl-directed repair of DNA base-pair mismatches in vitro, Proc. Natl. Acad. Sci. USA, 80:4639-4643, 1983.
Lund et al.: A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma et al.: DNA synthesis, assembly and application in synthetic biology. Current Opinion in Chemical Biology. 16:260-267, 2012.
Ma et al.: Versatile surface functionalization of cyclic olefin copolymer (COC) with sputtered SiO2 thin film for potential BioMEMS applications. Journal of Materials Chemistry, 11 pages, 2009.
Mahato et al.: Modulation of gene expression by antisense and antigene oligodeoxynucleotides and small interfering RNA Expert Opin. Drug Delivery, 2(1):3-28, 2005.
Malecek et al.: Engineering improved T cell receptors using an alanine-scan guided T cell display selection system. Journal of Immunological Methods. Elsevier Science Publishers. 392(1):1-11 (2013).
Margulies et al.: Genome sequencing in open microfabricated high-density picolitre reactors. Nature. 437(7057):376-80, 2005.
Martinez-Torrecuadrada et al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Matteucci et al.: Synthesis of deoxyoligonucleotides on a polymer support. J. Am. Chem. Soc. 103(11):3185-3191, 1981.
Matzas et al.: Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers. An investigation of several deoxynucleoside phosphoramidites useful for synthesizing deoxyoligonucleotides. Tetrahedron Lett. 24: 245-248, 1983.
Mcgall et al.: Light-directed synthesis of high-density oligonucleotide arrays using semiconductor photoresists. Proc Natl Acad Sci U S A. 93(24):13555-60, 1996.
Mcgall et al.: The Efficiency of Light-Directed Synthesis of DNA Arrays on Glass Substrates. J. Am. Chem. Soc. 119(22):5081-5090, 1997.
Mei et al.: Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland. Knowledge-based simulation of genetic regulation in bacteriophage lambda. Nucl. Acids Research, 12(1):1-16, 1984.
Meynert et al.: Quantifying single nucleotide variant detection sensitivity in exome sequencing. BMC Bioinformatics 14:195 (2013).
Meynert et al.: Variant detection sensitivity and biases in whole genome and exome sequencing. BMC Bioinformatics 15:247 (2014).
Milo and Phillips. Numbers here reflect the No. of protein coding genes and excludes tRNA and non-coding RNA. Cell Biology by the Numbers, p. 286, 2015.
Mitra et al.: In situ localized amplification and contact replication of many individual DNA molecules. Nucleic Acids Res. 27(24):e34, 1999.
MLAB 2321 Molecular Diagnostics for Clinical Laboratory Science. Mar. 6, 2015.
Momentiv. Technical Data Sheet. Silquest A-1100. Momentiv. 1-6 (2020).
Morin et al.: Profiling the HeLa S3 transcriptome using randomly primed cDNA and massively parallel short-read sequencing. Biotechniques, 45:81-94, 2008.
Morris and Stauss. Optimizing T-cell receptor gene therapy for hematologic malignancies. Blood, 127(26):3305-3311, 2016.
Muller et al.: Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).
Nakatani et al.: Recognition of a single guanine bulge by 2-Acylamino-1,8-naphthyridine, J. Am. Chem. Soc., vol. 122, 2172-2177 (2000).
Jo et al.: Engineering therapeutic antibodies targeting G-protein-coupled receptors; Experimental & Molecular Medicine; 48; 9 pages (2016).
Neiman M.S.: Negentropy principle in information processing systems. Radiotekhnika, 1966, No. 11, p. 2-9.
Neiman M.S.: On the bases of the theory of information retrieval. Radiotekhnika, 1967, No. 5, p. 2-10.
Neiman M.S.: On the molecular memory systems and the directed mutations. Radiotekhnika, 1965, No. 6, pp. 1-8.
Neiman M.S.: On the relationships between the reliability, performance and degree of microminiaturization at the molecular-atomic level. Radiotekhnika, 1965, No. 1, pp. 1-9.
Neiman M.S.: Some fundamental issues of microminiaturization. Radiotekhnika, 1964, No. 1, pp. 3-12.
Nishikura. A short primer on RNAi: RNA-directed RNA polymerase acts as a key catalyst Cell, 107:415-418, 2001.
Nour-Eldin et al.: USER Cloning and USER Fusion: The Ideal Cloning Techniques for Small and Big Laboratories. Plant Secondary Metabolism Engineering. Methods in Molecular Biology vol. 643, 2010, pp. 185-200.
Novartis Institutes for Biomedical Research. Immunoglobulin Heavy Chain [*Homo sapiens*]. National Center for Biotechnology Information. Genbank Entry. pp. 1-2 (2018) https://www.ncbi.nlm.nih.gov/nuccore/MH975524.1ttps://https://www.ncbi.nlm.nih.gov/nuccore/MH975524.1.
Novartis Institutes for Biomedical Research. Immunoglobulin Lambda Chain [*Homo sapiens*]. National Center for Biotechnology Information. Genbank Entry. pp. 1-2 (2018) https://www.ncbi.nlm.nih.gov/nuccore/MH975524.1.
Nucleic acid thermodynamics. Wikipedia. Feb. 4, 2021.
Ochman et al.: Genetic applications of an inverse polymerase chain reaction. Genetics. Nov. 1988;120(3):621-3.
O'Driscoll et al.: Synthetic DNA: The next generation of big data storage. Bioengineered. 4(3):123-125 (2013).
Opposition to European Patent No. 3030682 filed Mar. 3, 2021.
Organick et al.: Random access in large-scale DNA data storage. Nature Biotechnology, Advance Online Publication, 8 pages, 2018.

(56) References Cited

OTHER PUBLICATIONS

Organick et al.: Scaling up DNA data storage and random access retrieval, bioRxiv, preprint first posted online Mar. 7, 2017, 14 pages.
Pan et al.: An approach for global scanning of single nucleotide variations. Proc Natl Acad Sci USA. Jul. 9, 2002;99(14):9346-51.
Pankiewicz. Fluorinated nucleosides. Carbohydr Res. Jul. 10, 2000;327(1-2):87-105.
Paul et al.: Acid binding and detrylation during oligonucleotide synthesis. Nucleic Acids Research. 15. pp. 3048-3052 (1996).
PCT/IL2012/000326 International Preliminary Report on Patentability dated Dec. 5, 2013.
PCT/IL2012/000326 International Search Report dated Jan. 29, 2013.
PCT/US2014/049834 International Preliminary Report on Patentability dated Feb. 18, 2016.
PCT/US2014/049834 International Search Report and Written Opinion dated Mar. 19, 2015.
PCT/US2014/049834, Invitation to Pay Additional Fees dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Preliminary Report on Patentability dated Feb. 26, 2019.
PCT/US2017/026232 International Search Report and Written Opinion dated Aug. 28, 2017.
PCT/US2017/036868 International Search Report and Written Opinion dated Aug. 11, 2017.
PCT/US2017/045105 International Preliminary Report on Patentability dated Feb. 5, 2019.
PCT/US2017/045105 International Search Report and Written Opinion dated Oct. 20, 2017.
PCT/US2017/052305 International Preliminary Report on Patentability dated Apr. 30, 2019.
PCT/US2017/052305 International Search Report and Written Opinion dated Feb. 2, 2018.
PCT/US2017/062391 International Preliminary Report on Patentability dated May 21, 2019.
PCT/US2017/062391 International Search Report and Written Opinion dated Mar. 28, 2018.
PCT/US2017/066847 International Search Report and Written Opinion dated May 4, 2018.
PCT/US2018/019268 International Preliminary Report on Patentability dated Aug. 27, 2019.
PCT/US2018/022487 International Search Report and Written Opinion dated Aug. 1, 2018.
PCT/US2018/022493 International Search Report and Written Opinion dated Aug. 1, 2018.
PCT/US2018/037152 International Preliminary Report on Patentability dated Dec. 17, 2019.
PCT/US2018/037152 International Search Report and Written Opinion dated Aug. 28, 2018.
PCT/US2018/037161 International Preliminary Report on Patentability dated Dec. 17, 2019.
PCT/US2018/037161 International Search Report and Written Opinion dated Oct. 22, 2018.
PCT/US2018/037161 Invitation to Pay Additional Fees dated Aug. 27, 2018.
PCT/US2018/050511 International Preliminary Report on Patentability dated Mar. 17, 2020.
PCT/US2018/050511 International Search Report and Written Opinion dated Jan. 11, 2019.
PCT/US2018/056783 International Preliminary Report on Patentability dated Apr. 30, 2020.
PCT/US2018/056783 International Search Report and Written Opinion of the International Searching Authority dated Dec. 20, 2018.
PCT/US2018/057857 International Preliminary Report on Patentability dated Apr. 28, 2020.
PCT/US2018/057857 International Search Report and Written Opinion dated Mar. 18, 2019.
PCT/US2018/19268 International Search Report and Written Opinion dated Jun. 26, 2018.
PCT/US2018/19268 Invitation to Pay Additional Fees dated May 2, 2018.
PCT/US2018/22487 Invitation to Pay Additional Fees dated May 31, 2018.
PCT/US2018/22493 Invitation to Pay Additional Fees dated May 31, 2018.
PCT/US2019/012218 International Preliminary Report on Patentability dated Jul. 16, 2020.
PCT/US2019/012218 International Search Report and Written Opinion dated Mar. 21, 2019.
PCT/US2019/032992 International Preliminary Report on Patentability dated Nov. 24, 2020.
PCT/US2019/032992 International Search Report and Written Opinion dated Oct. 28, 2019.
PCT/US2019/032992 Invitation to Pay Additional Fees dated Sep. 6, 2019.
PCT/US2019/068435 International Preliminary Report on Patentability dated Jul. 8, 2021.
PCT/US2019/068435 International Search Report and Written Opinion dated Apr. 23, 2020.
PCT/US2020/019371 International Preliminary Report on Patentability dated Sep. 2, 2021.
PCT/US2020/019371 International Search Report and Written Opinion dated Jun. 25, 2020.
PCT/US2020/019986 International Preliminary Report on Patentability dated Sep. 10, 2021.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Preliminary Report on Patentability dated Sep. 10, 2021.
PCT/US2020/019988 International Search Report and Written Opinion dated Jul. 29, 2020.
PCT/US2020/019988 Invitation to Pay Additional Fees dated Jun. 8, 2020.
PCT/US2020/038679 International Search Report and Written Opinion dated Oct. 28, 2020.

(56) References Cited

OTHER PUBLICATIONS

PCT/US2020/052291 International Preliminary Report on Patentability dated Apr. 7, 2022.
PCT/US2020/052291 International Search Report and Written Opinion dated Mar. 10, 2021.
PCT/US2020/052291 Invitation to Pay Additional Fees dated Dec. 31, 2020.
PCT/US2020/052306 International Preliminary Report on Patentability dated Mar. 15, 2022.
PCT/US2020/052306 International Search Report and Written Opinion dated Mar. 2, 2021.
PCT/US2020/052306 Invitation to Pay Additional Fees dated Dec. 18, 2020.
PCT/US2020/064106 International Search Report and Written Opinion dated Jun. 3, 2021.
PCT/US2020/064106 Invitation to Pay Additional Fees dated Apr. 9, 2021.
PCT/US2022/023936 International Search Report and Written Opinion dated Jul. 14, 2022.
Pease et al.: Light-generated oligonucleotide arrays for rapid DNA sequence analysis. Proc Natl Acad Sci U S A. May 24, 1994;91(11):5022-6.
Peisajovich et al.: BBF RFC 28: A method for combinatorial multi-part assembly based on the type-lis restriction enzyme aarI. Sep. 16, 2009, 7 pages.
Pellois et al.: Individually addressable parallel peptide synthesis on microchips, Nature Biotechnology, vol. 20, 922-926 (Sep. 2002).
Petersen et al.: LNA: a versatile tool for therapeutics and genomics. Trends Biotechnol. Feb. 2003;21(2):74-81.
Pierce and Wangh. Linear-after-the-exponential polymerase chain reaction and allied technologies Real-time detection strategies for rapid, reliable diagnosis from single cells Methods Mol. Med. 132:65-85 (2007) (Abstract only).
Pierce et al.: Linear-after-the-exponential polymerase chain reaction and allied technologies. Real-time detection strategies for rapid, reliable diagnosis from single cells. Methods Mol Med. 2007;132:65-85.
Pigott et al.: The Use of a Novel Discovery Platform to Identify Peptide-Grafted Antibodies that Activate GLP-1 Receptor Signaling. Innovative Targeting Solutions Inc. (2013) XP055327428 retrieved from the internet: http://www.innovativetargeting.com/wo-content/uploads/2013/12/Pigott-et-al-Antibody-Engineering-2013.pdf.
Pirrung. How to make a DNA chip. Angew. Chem. Int. Ed., 41:1276-1289, 2002.
Plesa et al.: Multiplexed gene synthesis in emulsions for exploring protein functional landscapes. Science, 10.1126/science.aao5167, 10 pages, 2018.
Pon. Solid-phase supports for oligonucleotide synthesis. Methods Mol Bio. 1993;20:465-96.
Ponsel. High Affinity, Developability and Functional Size: The Holy Grail of Combinatorial Antibody Library Generation. Molecules. 16:3675-3700 (2011).
Poster. Reimagine Genome Scale Research. 2016, 1 page. Available at http://www2.twistbioscience.com/Oligo_Pools_CRISPR_poster.
Powers et al.: Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.
Prodromou et al.: Recursive PCR: a novel technique for total gene synthesis. Protein Eng. Dec. 1992;5(8):827-9.
PubChem Data Sheet Acetonitrile. Printed from website https://pubchem.ncbi.nlm.nig.gov/ pp. 1-124 (2020).
PubChem Data Sheet Dichloromethane. Printed from website https://pubchem.ncbi.nlm.nih.gov/compound/Dichloromethane (2020).
PubChem Data Sheet Methylene Chloride. Printed from website https://pubchem.ncbi.nlm.nih.gov/ pp. 1-140 (2020).

Puigbo. Optimizer: a web server for optimizing the codon usage of DNA sequences. Nucleic Acid Research, 35(14):126-131, 2007.
Qian and Winfree. Scaling up digital circuit computation with DNA strand displacement cascades. Science, 332(6034):196-1201, 2011.
Qian et al.: Neural network computation with DNA strand displacement cascades, Nature, 475(7356):368-372, 2011.
Quan et al.: Parallel on-chip gene synthesis and application to optimization of protein expression, Nature Biotechnology, 29(5):449-452, 2011.
Rafalski and Morgante. Corn and humans: recombination and linkage disequilibrium in two genomes of similar size. Trends in Genetics, 20(2):103-111, 2004.
Raje and Murma. A Review of electrohydrodynamic-inkjet printing technology. International Journal of Emerging Technology and Advanced Engineering, 4(5):174-183, 2014.
Rajpal et al.: A general method for greatly improving the affinity of antibodies by using combinatorial libraries. Proc. Natl. Acad. Sci. 102(24):8466-8471 (2005).
Rastegari et al.: XNOR-Net: ImageNet Classification Using Binary Convolutional Neural Networks, in ECCV 2016, Part IV, LNCS 9908, p. 525-542, 2016.
Regep et al.: The H3 loop of antibodies shows unique structural characteristics. Proteins. 85(7):1311-1318 (2017).
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond et al.: Amplification and assembly of chip-eluted Dna (Aaced): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQs and Ordering Guide. Roche Applied Science. Accessed Jan. 12, 2015, 37 pages.
Rogozin et al.: Origin and evolution of spliceosomal introns. Biology Direct, 7:11, 2012.
Ruminy et al.: Long-range identification of hepatocyte nuclear factor-3 (FoxA) high and low-affinity binding Sites with a chimeric nuclease, J. Mol. Bio., vol. 310, 523-535 (2001).
Saaem et al.: In situ synthesis of DNA microarray on functionalized cyclic olefin copolymer substrate ACS Applied Materials & Interfaces, 2(2):491-497, 2010.
Saboulard et al.: High-throughput site-directed mutagenesis using oligonucleotides synthesized on DNA chips. Biotechniques. Sep. 2005;39(3):363-8.
Sacconi et al.: Three-dimensional magneto-optic trap for microobject manipulation, Optics Letters, vol. 26, No. 17, 1359-1361 (Sep. 1, 2001).
Saiki et al.: Analysis of enzymatically amplified beta-globin and HLA-DQ alpha DNA with allele-specific oligonucleotide probes. Nature 324:163-166 (1986).
Sandhu et al.: Dual asymmetric PCR: one-step construction of synthetic genes. Biotechniques. Jan. 1992;12(1):14-6.
Sargolzaei et al.: Extent of linkage disequilibrium in Holstein cattle in North America. J.Dairy Science, 91:2106-2117, 2007.
Schaller et al.: Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al.: Microchip electrophoresis: a method for highspeed SNP detection. Nucleic Acids Res 28(9):E43 (2000).
Schmitt et al.: New strategies in engineering T-cell receptor genemodified T cells to more effectively target malignancies. Clinical Cancer Research, 21(23):5191-5197, 2015.
Seelig et al.: Enzyme-Free Nucleic Acid Logic Circuits, Science 314(5805):1585-1588, 2006.

(56) References Cited

OTHER PUBLICATIONS

Sharan et al.: Recombineering: a homologous recombination-based method of genetic engineering. Nat Profile 4(2):1-37 (originally pp. 206-223) (2009).
Sharpe and Mount. Genetically modified T cells in cancer therapy: opportunities and challenges. Disease Models and Mechanisms, 8:337-350, 2015.
Shipman et al.: Molecular recordings by directed CRISPR spacer acquisition. Science. 353(6298):1-16 (2016).
Sierzchala et al.: Solid-phase oligodeoxynucleotide synthesis : a two-step cycle using peroxy anion deprotection, J. Am. Chem. Soc., vol. 125, No. 44, 13427-13441 (2003).
Simonyan and Zisserman. Very Deep Convolutional Networks for Large-Scale Image Recognition, Published as a conference paper at Int. Conf. Learn. Represent., pp. 1-14, 2015.
Singh-Gasson et al.: Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith et al.: Direct mechanical measurements of the elasticity of single DNA molecules using magnetic beads, Science, vol. 258, 1122-1126 (Nov. 13, 1992).
Smith et al.: Changing the peptide specificity of a human T-cell receptor by directed evolution. Nature Communications. 5:1-13 (2014).
Smith et al.: Generating a synthetic genome by whole genome assembly: phix174 bacteriophage from synthetic oligonucleotides. Proc Natl Acad Sci U S A. Dec. 23, 2003;100(26):15440-5. Epub Dec. 2, 2003.
Smith et al.: Generation of cohesive ends on PCR products by UDG-mediated excision of dU, and application for cloning into restriction digest-linearized vectors. PCR Methods Appl. May 1993;2(4):328-32.
Smith et al.: Mutation detection with MutH, MutL, and MutS mismatch repair proteins, Proc. Natl. Acad. Sci. USA, vol. 93, 4374-4379 (Apr. 1996).
Smith et al.: Removal of Polymerase-Produced mutant sequences from PCR products, Proc. Natl. Acad. Sci. USA, vol. 94, 6847-6850 (Jun. 1997).
Solomon et al.: Genomics at Agilent: Driving Value in DNA Sequencing.https://www.agilent.com/labs/features/2010_genomics.html, 8 pages (Aug. 5, 2010).
Sommermeyer et al.: Minimal Amino Acid Exchange in Human TCR Constant Regions Fosters Improved Function of TCR Gene-Modified T Cells. Journal of Immunology. 184:6223-6231 (2010).
Soni et al.: Progress toward ultrafast DNA sequencing using solid-state nanopores. Clin Chem. Nov. 2007;53(11):1996-2001. Epub Sep. 21, 2007.
Southern et al.: Analyzing and comparing nucleic acid sequences by hybridization to arrays of oligonucleotides: evaluation using experimental models. Genomics. Aug. 1992;13(4):1008-17.
Sproat et al.: An efficient method for the isolation and purification of oligoribonucleotides. Nucleosides & Nucleotides. 1995; 14(1 &2):255-273.
Srivannavit et al.: Design and fabrication of microwell array chips for a solution-based, photogenerated acid-catalyzed parallel oligonucleotide DNA synthesis. Sensors and Actuators A, 116:150-160, 2004.
Srivastava et al.: RNA synthesis: phosphoramidites for RNA synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel. The Flow-Thru Chip A Three-dimensional biochip platform. In: Schena, Microarray Biochip Technology, Chapter 5, Natick, MA: Eaton Publishing, 2000, 33 pages.
Stemmer et al.: Single-step assembly of a gene and entire plasmid from large Nos. of oligodeoxyribonucleotides. Gene. Oct. 16, 1995;164(1):49-53.
Stryer. DNA Probes and genes can be synthesized by automated solid-phase methods. Biochemistry, 3rd edition, New York: W.H. Freeman and Company, 1988; 123-125.
Stutz et al.: Novel fluoride-labile nucleobase-protecting groups for the synthesis of 3'(2∝)-O-amino-acylated RNA sequences. Helv. Chim. Acta. 2000; 83(9):2477-2503.
Sullivan et al.: Library construction and evaluation for site saturation mutagenesis. Enzyme Microb. Technol. 53:70-77 (2013).
Sun et al.: Structure-Guided Triple-Code Saturation Mutagenesis: Efficient Tuning of the Stereoselectivity of an Epoxide Hydrolase. ACS Catal. 6:1590-1597 (2016).
Takahashi. Cell-free cloning using multiply-primed rolling circle amplification with modified RNA primers. Biotechniques. Jul. 2009;47(1):609-15. doi: 10.2144/000113155.
Tanase et al.: Magnetic trapping of multicomponent nanowires, The Johns Hopkins University, Baltimore, Maryland, p. 1-3 (Jun. 25, 2001).
Taylor et al.: Impact of surface chemistry and blocking strategies on DNA microarrays. Nucleic Acids Research, 31(16):e87, 19 pages, 2003.
The SLIC. Gibson, CPEC and SLiCE assembly methods (and GeneArt Seamless, In-Fusion Cloning). 5 pages, available online Sep. 2, 2010.
Tian et al.: Accurate multiplex gene synthesis from programmable DNA microchips. Nature. Dec. 23, 2004;432(7020):1050-1054.
Tsai et al.: Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
Unger et al.: Monolithic microfabricated valves and pumps by multilayer soft lithography. Science. Apr. 7, 2000;288(5463):113-6.
U.S. Appl. No. 14/241,874 Final Office Action dated Jan. 28, 2019.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4, 2018.
U.S. Appl. No. 14/452,429 Notice of Allowance dated Jun. 7, 2016.
U.S. Appl. No. 14/452,429 Office Action dated Apr. 9, 2015.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 10, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Aug. 19, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Final Office Action dated Feb. 21, 2019.
U.S. Appl. No. 15/151,316 Final Office Action dated Jul. 9, 2020.
U.S. Appl. No. 15/151,316 Office Action dated Jun. 7, 2018.
U.S. Appl. No. 15/151,316 Office Action dated Oct. 4, 2019.
U.S. Appl. No. 15/154,879 Notice of Allowance dated Feb. 1, 2017.
U.S. Appl. No. 15/156,134 Final Office Action dated Aug. 18, 2021.
U.S. Appl. No. 15/156,134 Final Office Action dated Jan. 3, 2020.
U.S. Appl. No. 15/156,134 Office Action dated Apr. 4, 2019.

(56) References Cited

OTHER PUBLICATIONS

U.S. Appl. No. 15/156,134 Office Action dated Nov. 25, 2020.
U.S. Appl. No. 15/187,714 Final Office Action dated Sep. 17, 2019.
U.S. Appl. No. 15/187,714 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Notice of Allowance dated Dec. 14, 2017.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Final Office Action dated Oct. 3, 2019.
U.S. Appl. No. 15/268,422 Office Action dated Mar. 1, 2019.
U.S. Appl. No. 15/268,422 Restriction Requirement dated Oct. 4, 2018.
U.S. Appl. No. 15/272,004 Final Office Action dated Mar. 18, 2021.
U.S. Appl. No. 15/272,004 Office Action dated Apr. 13, 2022.
U.S. Appl. No. 15/272,004 Office Action dated Jun. 12, 2020.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Final Office Action dated Nov. 6, 2019.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Jun. 26, 2019.
U.S. Appl. No. 15/603,013 Office Action dated Oct. 20, 2017.
U.S. Appl. No. 15/619,322 Final Office Action dated Jul. 9, 2021.
U.S. Appl. No. 15/619,322 Final Office Action dated Mar. 30, 2020.
U.S. Appl. No. 15/619,322 Office Action dated Aug. 14, 2019.
U.S. Appl. No. 15/619,322 Office Action dated Nov. 4, 2020.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Office Action dated May 19, 2020.
U.S. Appl. No. 15/816,995 Office Action dated Sep. 20, 2019.
U.S. Appl. No. 15/816,995 Restriction Requirement dated Apr. 4, 2019.
U.S. Appl. No. 15/835,342 Office Action dated Jun. 17, 2022.
U.S. Appl. No. 15/835,342 Office Action dated Apr. 16, 2021.
U.S. Appl. No. 15/835,342 Final Office Action dated Sep. 8, 2020.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/902,855 Final Office Action dated Aug. 11, 2022.
U.S. Appl. No. 15/902,855 Office Action dated Dec. 9, 2021.
U.S. Appl. No. 15/902,855 Office Action dated Oct. 5, 2022.
U.S. Appl. No. 15/902,855 Restriction Requirement dated Apr. 6, 2021.
U.S. Appl. No. 15/921,479 Final Office Action dated Dec. 20, 2021.
U.S. Appl. No. 15/921,479 Final Office Action dated Jun. 15, 2020.
U.S. Appl. No. 15/921,479 Office Action dated Apr. 27, 2021.
U.S. Appl. No. 15/921,479 Office Action dated Apr. 28, 2022.
U.S. Appl. No. 15/921,479 Office Action dated Nov. 12, 2019.
U.S. Appl. No. 15/921,479 Restriction Requirement dated May 24, 2019.
U.S. Appl. No. 15/960,319 Office Action dated Aug. 16, 2019.
U.S. Appl. No. 15/991,992 Office Action dated May 21, 2020.
U.S. Appl. No. 15/991,992 Restriction Requirement dated Mar. 10, 2020.
U.S. Appl. No. 16/006,581 Office Action dated Sep. 25, 2019.
U.S. Appl. No. 16/031,784 Office Action dated May 12, 2020.
U.S. Appl. No. 16/039,256 Final Office Action dated Mar. 30, 2021.
U.S. Appl. No. 16/039,256 Office Action dated Aug. 20, 2020.
U.S. Appl. No. 16/039,256 Office Action dated May 10, 2022.
U.S. Appl. No. 16/039,256 Restriction Requirement dated May 18, 2020.
U.S. Appl. No. 16/128,372 Final Office Action dated Mar. 18, 2021.
U.S. Appl. No. 16/128,372 Office Action dated Dec. 13, 2021.
U.S. Appl. No. 16/128,372 Office Action dated Oct. 8, 2020.
U.S. Appl. No. 16/128,372 Restriction Requirement dated May 18, 2020.
U.S. Appl. No. 16/165,952 Office Action dated Mar. 12, 2020.
U.S. Appl. No. 16/239,453 Office Action dated May 11, 2020.
U.S. Appl. No. 16/239,453 Office Action dated Nov. 7, 2019.
U.S. Appl. No. 16/384,678 Final Office Action dated Oct. 15, 2020.
U.S. Appl. No. 16/384,678 Office Action dated Jan. 21, 2020.
U.S. Appl. No. 16/409,608 Office Action dated Sep. 9, 2019.
U.S. Appl. No. 16/417,023 Final Office Action dated Aug. 2, 2022.
U.S. Appl. No. 16/417,023 Office Action dated Feb. 22, 2022.
U.S. Appl. No. 16/530,717 Final Office Action dated Apr. 15, 2020.
U.S. Appl. No. 16/530,717 Office Action dated Sep. 6, 2019.
U.S. Appl. No. 16/535,777 Final Office Action dated Oct. 20, 2020.
U.S. Appl. No. 16/535,777 Office Action dated Feb. 8, 2021.
U.S. Appl. No. 16/535,777 Office Action dated Jan. 23, 2020.
U.S. Appl. No. 16/535,779 First Action Interview dated Feb. 10, 2020.
U.S. Appl. No. 16/590,301 Office Action dated Jul. 20, 2022.
U.S. Appl. No. 16/590,301 Restriction Requirement dated Apr. 28, 2022.
U.S. Appl. No. 16/712,678 Office Action dated Nov. 26, 2021.
U.S. Appl. No. 16/712,678 Restriction Requirement dated Aug. 25, 2021.
U.S. Appl. No. 16/726,073 Office Action dated Jun. 30, 2022.
U.S. Appl. No. 16/737,401 Final Office Action dated Jun. 13, 2022.
U.S. Appl. No. 16/737,401 Office Action dated Jan. 5, 2022.
U.S. Appl. No. 16/737,401 Restriction Requirement dated Nov. 15, 2021.
U.S. Appl. No. 16/798,275 Final Office Action dated Aug. 30, 2021.
U.S. Appl. No. 16/798,275 Office Action dated Feb. 10, 2021.
U.S. Appl. No. 16/802,423 Notice of Allowance dated Jul. 25, 2022.
U.S. Appl. No. 16/802,423 Restriction Requirement dated Dec. 29, 2021.
U.S. Appl. No. 16/802,439 Office Action dated Mar. 17, 2022.
U.S. Appl. No. 16/802,439 Restriction Requirement dated Oct. 1, 2021.
U.S. Appl. No. 16/854,719 Office Action dated Jun. 2, 2022.
U.S. Appl. No. 16/854,719 Office Action dated Nov. 24, 2021.
U.S. Appl. No. 16/854,719 Restriction Requirement dated Jul. 28, 2021.
U.S. Appl. No. 16/879,705 Office Action dated Sep. 9, 2021.
U.S. Appl. No. 16/906,555 Office Action dated Aug. 17, 2021.
U.S. Appl. No. 17/154,906 Office Action dated May 17, 2022.
U.S. Appl. No. 16/921,712 Non-Final Office Action dated Nov. 25, 2022.
U.S. Appl. No. 17/154,906 Office Action dated Nov. 10, 2021.

(56) References Cited

OTHER PUBLICATIONS

U.S. Appl. No. 17/154,906 Restriction Requirement dated Jul. 26, 2021.
U.S. Appl. No. 17/180,614 Office Action dated Oct. 5, 2022.
U.S. Appl. No. 15/921,537 Office Action dated Apr. 1, 2020.
Vaijayanthi et al.: Recent advances in oligonucleotide synthesis and their applications. Indian J Biochem Biophys. Dec. 2003;40(6):377-91.
Van Den Brulle et al.: A novel solid phase technology for high-throughput gene synthesis. Biotechniques. 2008; 45(3):340-343.
Van Der Velde: Thesis. Finding the Strength of Glass. Delft University of Technology. 1-16 (2015).
Van Der Werf et al.: Limonene-1,2-epoxide hydrolase from Rhodococcus erythropolis DCL14 belongs to a novel class of epoxide hydrolases. J. Bacteriol. 180:5052-5057 (1998).
Van Tassell et al.: SNP discovery and allele frequency estimation by deep sequencing of reduced representation libraries. Nature Methods, 5:247-252, 2008.
Vargeese et al.: Efficient activation of nucleoside phosphoramidites with 4,5-dicyanoimidazole during oligonucleotide synthesis. Nucleic Acids Res. Feb. 15, 1998;26(4):1046-50.
Verma et al.: Modified oligonucleotides: synthesis and strategy for users. Annu Rev Biochem 67:99-134 (1998).
Vincent et al.: Helicase-dependent isothermal DNA amplification. EMBO Rep. Aug. 2004;5(8):795-800.
Visscher et al.: Construction of multiple-beam optical traps with nanometer-resolution position sensing, IEEE Journal of Selected Topics in Quantum Electronics, vol. 2, No. 4, 1066-1076 (Dec. 1996).
Voldmans et al.: Holding forces of single-particle dielectrophoretic traps. Biophysical Journal, vol. 80, No. 1, 531-541 (Jan. 2001).
Vos et al.: AFLP: A new technique for DNA fingerprinting. Nucleic Acids Res. Nov. 11, 1995;23(21):4407-14.
Wagner et al.: Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah et al.: Structure of Fok I has implications for DNA cleavage, Proc. Natl. Acad. Sci. USA, vol. 95, 10564-10569 (Sep. 1998).
Wah et al.: Structure of the multimodular endonuclease Fok I bound to DNA, Nature, vol. 388, 97-100 (Jul. 1997).
Walker et al.: Strand displacement amplification—an isothermal, in vitro DNA amplification technique. Nucleic Acids Res. Apr. 11, 1992;20(7):1691-6.
Wan et al.: Deep Learning for Content-Based Image Retrieval: A comprehensive study. in Proceedings of the 22nd ACM International Conference on Multimedia—Nov. 3-7, 2014, Orlando, FL, p. 157-166, 2014.
Warr et al.: Exome Sequencing: current and future perspectives. G3: (Bethesda) 5(8):1543-1550 (2015).
Weber et al.: A modular cloning system for standardized assembly of multigene constructs. PLoS One. Feb. 18, 2011;6(2):e16765. doi: 10.1371/journal.pone.0016765.
Welz et al.: 5-(Benzylmercapto)-1H-tetrazole as activator for 2'-O-TBDMS phosphoramidite building blocks in RNA synthesis. Tetrahedron Lett. 2002; 43(5):795-797.
Westin et al.: Anchored multiplex amplification on a microelectronic chip array Nature Biotechnology, 18:199-202 (2000) (abstract only).
Whitehouse et al.: Analysis of the mismatch and insertion/deletion binding properties of Thermus thermophilus, HB8, MutS, Biochemical and Biophysical Research Communications, vol. 233, 834-837 (1997).
Wiedenheft et al.: RNA-guided genetic silencing systems in bacteria and archaea. Nature 482:331-338 (2012).
Wijshoff. Structure and fluid-dynamics in Piezo inkjet printheads. Thesis. Venio, The Netherlands, published 2008, p. 1-185.
Wikipedia. Central dogma of molecular biology. URL: https://en.wikipedia.org/wiki/Central_dogma_of_molecular_biology. 9 pages (2021).
Williams et al.: Amplification of complex gene libraries by emulsion PCR. Nature Methods. 3(7):545-550(2006).
Wirtz. Direct measurement of the transport properties of a single DNA molecule, Physical Review Letters, vol. 75, No. 12, 2436-2439 (Sep. 18, 1995).
Withers-Martinez et al.: PCR-based gene synthesis as an efficient approach for expression of the A+ T-rich malaria genome, Protein Engineering, vol. 12, No. 12, 1113-1120 (1999).
Wood et al.: Human DNA repair genes, Science, vol. 291, 1284-1289 (Feb. 16, 2001).
Wosnick et al.: Rapid construction of large synthetic genes: total chemical synthesis of two different versions of the bovine prochymosin gene. Gene. 1987;60(1):115-27.
Wright and Church. An open-source oligomicroarray standard for human and mouse. Nature Biotechnology, 20:1082-1083, 2002.
Wu et al.: An improvement of the on-line electrophoretic concentration method for capillary electrophoresis of proteins an experimental factors affecting he concentration effect, Analytical Sciences, vol. 16, 329-331 (Mar. 2000).
Wu et al.: RNA-mediated gene assembly from DNA arrays. Angew Chem Int Ed Engl. May 7, 2012;51(19):4628-32. doi: 10.1002/anie.201109058.
Wu et al.: Sequence-Specific Capture of Protein-DNA Complexes for Mass Spectrometric Protein Identification PLoS ONE. Oct. 20, 2011, vol. 6, No. 10.
Wu et al.: Specificity of the nick-closing activity of bacteriophage T4 DNA ligase. Gene. 1989;76(2):245-54.
Xiong et al.: A simple, rapid, high-fidelity and cost-effective PCR-based two-step DNA synthesis method for long gene sequences. Nucleic Acids Res. 2004, 32(12):e98.
Xiong et al.: Chemical gene synthesis: Strategies, softwares, error corrections, and applications. FEMS Microbiol. Rev., 32:522-540, 2008.
Xiong et al.: Non-polymerase-cycling-assembly-based chemical gene synthesis: Strategies, methods, and progress. Biotechnology Advances. 26(2):121-134, 2008.
Xu et al.: Coordination between the Polymerase and 5'-Nuclease Components of DNA Polymerase I of *Escherichia coli*. The Journal of Biological Chemistry. 275(27):20949-20955 (2000).
Xu et al.: Design of 240,000 orthogonal 25mer DNA barcode probes. PNAS, 106(7):2289-2294, 2009.
Yang et al.: Purification, cloning, and characterization of the CEL I nuclease, Biochemistry, 39(13):3533-35, 2000.
Yazdi et al.: A Rewritable, Random-Access DNA-Based Storage System, Scientific Reports, 5, Article No. 14138, 27 pages, 2015.
Yazdi et al.: DNA-Based Storage: Trends and Methods. IEEE Transactions on Molecular, Biological and Multi-Scale Communications. IEEE. 1(3):230-248 (2016).
Yehezkel et al.: De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil et al.: Detection of 81 of 81 known mouse Beta-Globin promoter mutations with T4 Endonuclease VII• The EMC Method. Genomics, 32:431-435, 1996.
Young et al.: Two-step total gene synthesis method. Nucleic Acids Res. 32(7):e59, 2004.
Zhang and Seelig. Dynamic DNA nanotechnology using strand-displacement reactions, Nat. Chem., 3(2):103-113, 2011.
Zheleznaya et al.: Nicking endonucleases. Biochemistry (Mosc). 74(13):1457-66, 2009.
Zheng et al.: Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al.: Nucleic acid memory. Nature Materials, 15:366, 2016.
Zhou et al.: Establishment and application of a loop-mediated isothermal amplification (LAMP) system for detection of cry1Ac transgenic sugarcane Scientific Reports May 9, 2014, vol. 4, No. 4912.

(56) References Cited

OTHER PUBLICATIONS

Zhou et al.: Microfluidic PicoArray synthesis of oligodeoxynucleotides and simultaneous assembling of multiple DNA sequences Nucleic Acids Research, 32(18):5409-5417, 2004.

* cited by examiner 10 um 21 um

1101

NUCLEIC ACID BASED DATA STORAGE

CROSS-REFERENCE

This application is a continuation of U.S. patent application Ser. No. 17/578,356, filed Jan. 18, 2022, which is a continuation of U.S. patent application Ser. No. 16/927,826, filed Jul. 13, 2020, now U.S. Pat. No. 11,263,354, issued on Mar. 1, 2022, which is a continuation of U.S. patent application Ser. No. 16/415,960, filed May 17, 2019, now U.S. Pat. No. 10,754,994, issued on Aug. 25, 2020, which is a continuation of U.S. patent application Ser. No. 15/709,274 filed Sep. 19, 2017, now U.S. Pat. No. 10,417,457, issued on Sep. 17, 2019, which claims the benefit of U.S. Provisional Application No. 62/517,671 filed Jun. 9, 2017; U.S. Provisional Application No. 62/446,178 filed Jan. 13, 2017; and U.S. Provisional Application No. 62/397,855 filed Sep. 21, 2016, each of which are incorporated herein by reference in their entirety.

SEQUENCE LISTING

The instant application contains a Sequence Listing which has been submitted electronically in xml format and is hereby incorporated by reference in its entirety. Said xml copy, created on Oct. 4, 2022, is named 44854-728_304_SL.xml and is 7,000 bytes in size.

BACKGROUND

Biomolecule based information storage systems, e.g., DNA-based, have a large storage capacity and stability over time. However, there is a need for scalable, automated, highly accurate and highly efficient systems for generating biomolecules for information storage.

BRIEF SUMMARY

Provided herein are methods for storing and accessing information, the method comprising: (a) converting at least one item of information in a form of at least one digital sequence to at least one nucleic acid sequence; (b) providing a structure comprising a surface; (c) synthesizing a plurality of polynucleotides having predetermined sequences collectively encoding for the at least one nucleic acid sequence, wherein each polynucleotide extends from the surface; (d) storing the plurality of polynucleotides; and (e) selectively transferring the plurality of polynucleotides to a receiving unit, wherein selectively transferring comprises application of a force, wherein the force is laminar pressure, capillary pressure, slip flow pressure, magnetic force, electrostatic force, peristaltic force, sound waves, vibrational force, centripetal force, centrifugal force, or any combination thereof, and wherein the plurality of polynucleotides collectively encodes for a single nucleic acid sequence of the at least one nucleic acid sequence. Further provided herein are methods, wherein the application of force comprises a conducting member, and an applied voltage potential between the structure and the conducting member. Further provided herein are methods, wherein the application of force comprises contacting the surface of the structure with a rigid or flexible slip. Further provided herein are methods, wherein the application of force comprises a pressure release or pressure nozzle. Further provided herein are methods further comprising using the pressure nozzle during step (c). Further provided herein are methods further comprising flooding the polynucleotides through the pressure nozzle. Further provided herein are methods further comprising depositing nucleotides through the pressure nozzle. Further provided herein are methods further comprising: sequencing the plurality of polynucleotides; and assembling the at least one digital sequence. Further provided herein are methods, wherein the at least one digital sequence assembled is 100% accurate compared to an initial at least one digital sequence.

Provided herein are methods for storing information, the method comprising: (a) converting at least one item of information in a form of at least one digital sequence to at least one nucleic acid sequence; (b) synthesizing a plurality of polynucleotides having predetermined sequences collectively encoding for the at least one nucleic acid sequence, wherein each polynucleotide comprises: (i) a plurality of coding regions, wherein each coding region is identical; and (ii) at least one non-coding region, wherein the at least one non-coding region comprises a cleavage region; and (c) storing the plurality of polynucleotides. Further provided herein are methods, wherein the cleavage region comprises a restriction enzyme recognition site. Further provided herein are methods, wherein the cleavage region comprises a light sensitive nucleobase. Further provided herein are methods further comprising application of a restriction enzyme, electromagnetic radiation, or a gaseous reagent to cleave at the cleavage region, thereby removing at least one of the plurality of coding regions. Further provided herein are methods, wherein each coding region comprises 25 to 500 bases in length. Further provided herein are methods, wherein each coding region comprises 100 to 2000 bases in length. Further provided herein are methods, wherein each non-coding region comprises 1 to 100 bases in length. Further provided herein are methods, wherein each non-coding region comprises at most 200 bases. Further provided herein are methods, wherein the plurality of polynucleotides comprises at least 100,000 polynucleotides. Further provided herein are methods, wherein the plurality of polynucleotides comprises at least 10 billion polynucleotides. Further provided herein are methods, wherein greater than 90% of the polynucleotides encode for a sequence that does not differ from the predetermined sequence. Further provided herein are methods, wherein the at least one item of information is text information, audio information or visual information. Further provided herein are methods, wherein a first non-coding region within each polynucleotide has a different sequence than a second non-coding region within each polynucleotide. Further provided herein are methods, wherein each non-coding region within each polynucleotide has a different sequence. Further provided herein are methods, wherein a first cleavage region within each polynucleotide has a different sequence than a second cleavage region within each polynucleotide. Further provided herein are methods, wherein each cleavage region within each polynucleotide has a different sequence. Further provided herein are methods, wherein a number of cleavage regions within each polynucleotide is at least 1, 2, 3, 4, or 5. Further provided herein are methods, wherein a sequence for the number of cleavage regions is different. Further provided herein are methods, wherein each polynucleotide comprises a tether region.

Provided herein are methods for encrypting information, the method comprising: (a) converting at least one item of information in a form of at least one digital sequence to at least one nucleic acid sequence; (b) associating each of the at least one nucleic acid sequence with one of a plurality of non-identical markings; (c) providing a structure having a surface, wherein the surface comprises the plurality of non-identical markings; (d) synthesizing a plurality of polynucleotides having predetermined sequences collectively encoding for the at least one nucleic acid sequence, wherein the plurality of polynucleotides comprises at least 100,000 polynucleotides, and wherein each polynucleotide extends from the surface in a discrete region demarcated by one of the non-identical markings; and (e) storing the plurality of polynucleotides. Further provided herein are methods, wherein the plurality of polynucleotides comprises at least 1,000,000 polynucleotides. Further provided herein are methods, wherein greater than 90% of the polynucleotides encode for a sequence that does not differ from the predetermined sequence. Further provided herein are methods, wherein the at least one item of information is text information, audio information or visual information. Further provided herein are methods, wherein a subset of the polynucleotides discretely demarcated by one of the non-identical markings comprise a same sequence. Further provided herein are methods further comprising selecting a subset of polynucleotides discretely demarcated by one of the non-identical markings, releasing the subset of polynucleotides, sequencing the plurality of polynucleotides, decrypting the plurality of polynucleotides, and assembling the at least one digital sequence. Further provided herein are methods further comprising selecting a subset of polynucleotides discretely demarcated by one of the non-identical markings, amplifying the subset of polynucleotides, sequencing the subset of polynucleotides, decrypting the plurality of polynucleotides, and assembling the at least one digital sequence. Further provided herein are methods, wherein the at least one digital sequence assembled is 100% accurate compared to an initial at least one digital sequence. Further provided herein are methods, wherein the at least one digital sequence comprises an amount of digital information of at least 1 gigabyte. Further provided herein are methods, wherein the at least one digital sequence comprises an amount of digital information of at least 1 terabyte. Further provided herein are methods, wherein the at least one digital sequence comprises an amount of digital information of at least 1 petabyte.

Provided herein are methods for collection of information, the method comprising: (a) providing a structure comprising a surface, wherein the structure comprises: a first plurality of polynucleotides having predetermined sequences collectively encoding for at least one nucleic acid sequence; and a second plurality of polynucleotides having predetermined sequences collectively encoding for the at least one nucleic acid sequence, wherein the first plurality of polynucleotides and the second plurality of polynucleotides both extend from the surface and both encode for the same at least one nucleic acid sequence; (b) selectively separating a region of the structure comprising the first plurality of polynucleotides and removing the first plurality of polynucleotides from the surface; and (c) sequencing and decrypting the at least one nucleic acid sequence to form at least one digital sequence encoding for an item of information. Further provided herein are methods, wherein a region of the structure comprising the first plurality of polynucleotides comprises a cluster of channels or wells. Further provided herein are methods, wherein the structure is a rigid structure. Further provided herein are methods, wherein the structure is a flexible structure. Further provided herein are methods, wherein a region of the structure comprising only a remaining portion of the structure lacking the first plurality of polynucleotides is spliced back together. Further provided herein are methods, wherein selectively removing comprises application of force to a region of the structure comprising the first plurality of polynucleotides. Further provided herein are methods, wherein the application of force is laminar pressure, capillary pressure, slip flow pressure, magnetic force, electrostatic force, peristaltic force, sound waves, vibrational force, centripetal force, centrifugal force, or any combination thereof. Further provided herein are methods, wherein the application of force comprises a conducting member, and an applied voltage potential between the structure and the conducting member. Further provided herein are methods, wherein the application of force comprises contacting the surface of the structure with a rigid or flexible slip. Further provided herein are methods, wherein the application of force comprises a pressure release or pressure nozzle. Further provided herein are methods, wherein each polynucleotide of the first plurality of nucleotides comprises at most 500 bases in length. Further provided herein are methods, wherein each polynucleotide of the first plurality of nucleotides comprises at most 200 bases in length. Further provided herein are methods, wherein each polynucleotide of the second plurality of nucleotides comprises at most 500 bases in length. Further provided herein are methods, wherein each polynucleotide of the second plurality of nucleotides comprises at most 200 bases in length. Further provided herein are methods, wherein an amount of the item of information is at least one gigabyte. Further provided herein are methods, wherein an amount of the item of information is at least one terabyte. Further provided herein are methods, wherein an amount of the item of information is at least one petabyte.

Provided herein are nucleic acid libraries, comprising a plurality of polynucleotides, wherein each of the polynucleotides comprises: (i) a plurality of coding regions, wherein each coding region is identical; and (ii) at least one non-coding region, wherein the at least one non-coding region comprises a cleavage region; and wherein when the plurality of polynucleotides are sequenced, decrypted, and assembled to form a digital sequence, the digital sequence has greater than 90% accuracy compared to a preselected digital sequence. Further provided herein are nucleic acid libraries, wherein the cleavage region comprises a restriction enzyme recognition site. Further provided herein are nucleic acid libraries, wherein the cleavage region comprises a light sensitive nucleobase. Further provided herein are nucleic acid libraries, further comprising application of a restriction enzyme, electromagnetic radiation, or a gaseous reagent to cleave at the cleavage region, thereby removing at least one of the plurality of coding regions. Further provided herein are nucleic acid libraries, wherein each coding region comprises 25 to 500 bases in length. Further provided herein are nucleic acid libraries, wherein each coding region comprises 100 to 2000 bases in length. Further provided herein are nucleic acid libraries, wherein each non-coding region comprises 1 to 100 bases in length. Further provided herein are nucleic acid libraries, wherein each non-coding region comprises at most 200 bases. Further provided herein are nucleic acid libraries, wherein the plurality of polynucleotides comprises at least 100,000 polynucleotides. Further provided herein are nucleic acid libraries, wherein the plurality of polynucleotides comprises at least 10 billion polynucleotides. Further provided herein are nucleic acid libraries, wherein greater than 90% of the polynucleotides encode for a sequence that does not differ from a predetermined sequence. Further provided herein are nucleic acid libraries, wherein a first non-coding region within each polynucleotide has a different sequence than a second non-coding region within each polynucleotide. Further provided herein are nucleic acid libraries, wherein each non-coding region within each polynucleotide has a different sequence. Further provided herein are nucleic acid libraries, wherein a first cleavage region within each polynucleotide has a different sequence than a second cleavage region within each polynucleotide. Further provided herein are nucleic acid libraries, wherein each cleavage region within each polynucleotide has a different sequence. Further provided herein are nucleic acid libraries, wherein a number of cleavage regions within each polynucleotide is at least 1, 2, 3, 4, or 5. Further provided herein are nucleic acid libraries, wherein a sequence for the number of cleavage regions is different.

Provided herein are devices for storing information, the device comprising: (a) a structure having a surface; and (b) a plurality of discrete regions on the surface for synthesizing a plurality of polynucleotides having predetermined sequences collectively encoding for at least one nucleic acid sequence, wherein each polynucleotide comprises: (i) a plurality of coding regions, wherein each coding region is identical; and (ii) at least one non-coding region, wherein the at least one non-coding region comprises a cleavage region; and wherein the at least one nucleic acid sequence encodes for at least one item of information.

Provided herein are devices for encrypting information, the device comprising: (a) a structure having a surface, wherein the surface comprises a plurality of non-identical markings; and (b) a plurality of discrete regions on the surface for synthesizing a plurality of polynucleotides having predetermined sequences collectively encoding for at least one nucleic acid sequence, wherein the plurality of polynucleotides comprises at least 100,000 polynucleotides, and wherein each polynucleotide extends from the surface in a discrete region demarcated by one of the non-identical markings; and wherein the at least one nucleic acid sequence encodes for at least one item of information.

Provided herein are methods for storing information, the method comprising: (a) converting at least one item of information in the form of at least one digital sequence to at least one nucleic acid sequence; (b) synthesizing a plurality of polynucleotides having predetermined sequences collectively encoding for the at least one nucleic acid sequence, wherein each polynucleotide comprises: (i) at least one coding sequence up to about 500 bases in length; and (ii) at least one bar code sequence, wherein the bar code sequence comprises sequence associated with the identity of the coding sequence; and (c) storing the plurality of polynucleotides. Further provided herein are methods, wherein each polynucleotide comprises at least one coding sequence up to about 300 bases in length. Further provided herein are methods, wherein the plurality of polynucleotides comprises at least about 100,000 polynucleotides. Further provided herein are methods, wherein the plurality of polynucleotides comprises at least about 10 billion polynucleotides. Further provided herein are methods, wherein greater than 90% of the polynucleotides encode for a sequence that does not differ from the predetermined sequence. Further provided herein are methods, wherein the at least one item of information is text information, audio information or visual information.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
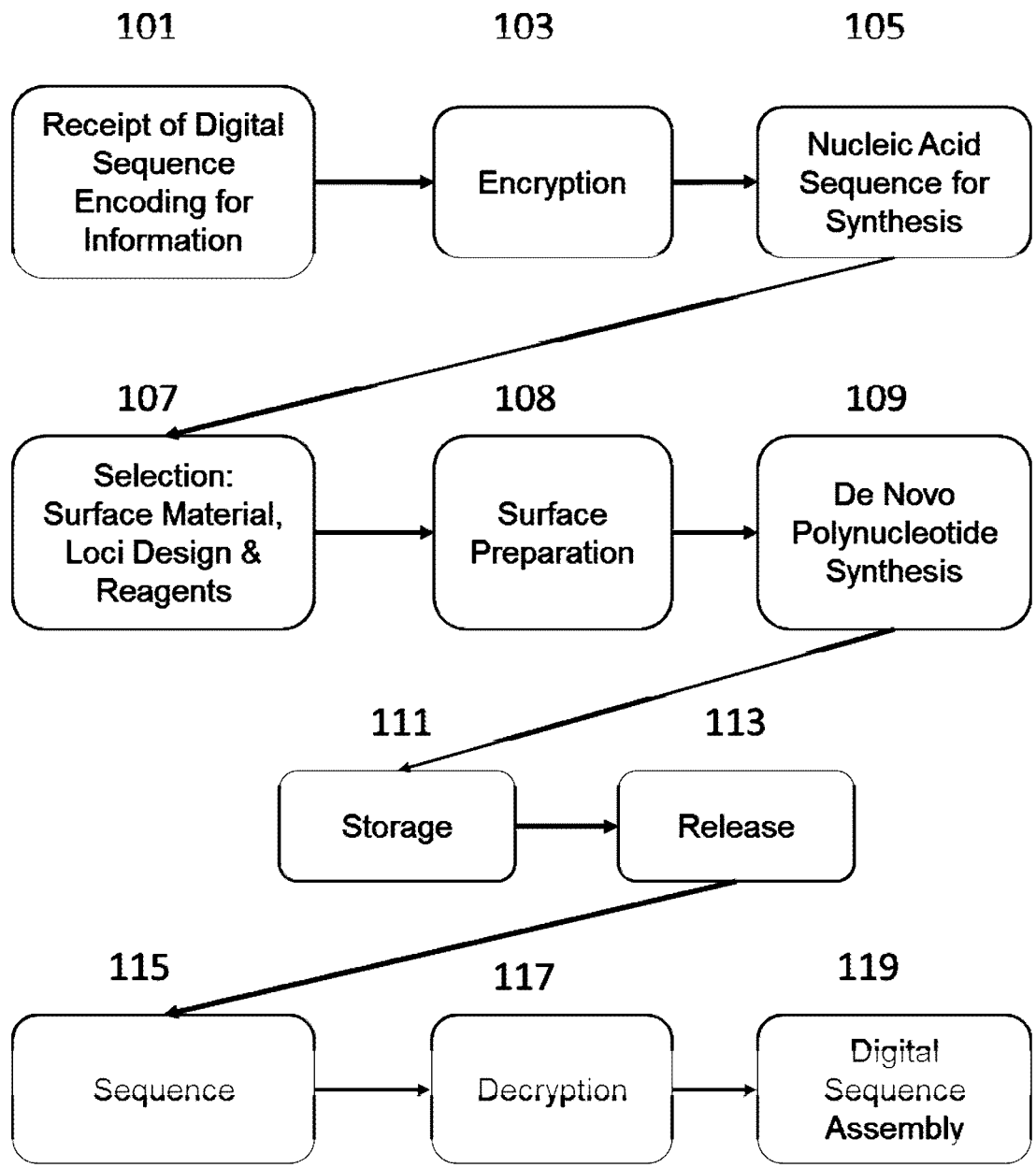
FIG. 1 illustrates an exemplary workflow for nucleic acid-based data storage.

There is a need for larger capacity storage systems as the amount of information generated and stored is increasing exponentially. Traditional storage media have a limited capacity and require specialized technology that changes with time, requiring constant transfer of data to new media, often at a great expense. A biomolecule such as a DNA molecule provides a suitable host for information storage in-part due to its stability over time and capacity for four bit information coding, as opposed to traditional binary information coding. Thus, large amounts of data are encoded in the DNA in a relatively smaller amount of physical space than used by commercially available information storage devices. Provided herein are methods to increase DNA synthesis throughput through increased sequence density and decreased turn-around time.

Definitions

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the oligonucleotide or polynucleotide being known and chosen before the synthesis or assembly of the nucleic acid molecules.

Provided herein are methods and compositions for production of synthetic (i.e. de novo synthesized or chemically synthesized) polynucleotides. Polynucleotides may also be referred to as oligonucleotides or oligos. Polynucleotide sequences described herein may be, unless stated otherwise, comprise DNA or RNA.

Nucleic Acid Based Information Storage

Provided herein are devices, compositions, systems and methods for nucleic acid-based information (data) storage. An exemplary workflow is provided in FIG. 1. In a first step, a digital sequence encoding an item of information (i.e., digital information in a binary code for processing by a computer) is received 101. An encryption 103 scheme is applied to convert the digital sequence from a binary code to a nucleic acid sequence 105. A surface material for nucleic acid extension, a design for loci for nucleic acid extension (aka, arrangement spots), and reagents for nucleic acid synthesis are selected 107. The surface of a structure is prepared for nucleic acid synthesis 108. De novo polynucleotide synthesis is performed 109. The synthesized polynucleotides are stored 111 and available for subsequent release 113, in whole or in part. Once released, the polynucleotides, in whole or in part, are sequenced 115, subject to decryption 117 to convert nucleic sequence back to digital sequence. The digital sequence is then assembled 119 to obtain an alignment encoding for the original item of information.

Items of Information

Optionally, an early step of a DNA data storage process disclosed herein includes obtaining or receiving one or more items of information in the form of an initial code. Items of information include, without limitation, text, audio and visual information. Exemplary sources for items of information include, without limitation, books, periodicals, electronic databases, medical records, letters, forms, voice recordings, animal recordings, biological profiles, broadcasts, films, short videos, emails, bookkeeping phone logs, internet activity logs, drawings, paintings, prints, photographs, pixelated graphics, and software code. Exemplary biological profile sources for items of information include, without limitation, gene libraries, genomes, gene expression data, and protein activity data. Exemplary formats for items of information include, without limitation, .txt, .PDF, .doc, .docx, .ppt, .pptx, .xls, .xlsx, .jpg, .gif, .psd, .bmp, .tiff, .png, and .mpeg. The amount of individual file sizes encoding for an item of information, or a plurality of files encoding for items of information, in digital format include, without limitation, up to 1024 bytes (equal to 1 KB), 1024 KB (equal to 1 MB), 1024 MB (equal to 1 GB), 1024 GB (equal to 1 TB), 1024 TB (equal to 1 PB), 1 exabyte, 1 zettabyte, 1 yottabyte, 1 xenottabyte or more. In some instances, an amount of digital information is at least 1 gigabyte (GB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 gigabytes. In some instances, the amount of digital information is at least 1 terabyte (TB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 terabytes. In some instances, the amount of digital information is at least 1 petabyte (PB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 petabytes.

Encryption

Binary Code Conversion

Generally, the initial code is digital information, typically in the form of binary code employed by a computer. General purpose computers are electronic devices reading "on" or "off" states, represented by the numbers "0" and "1". This binary code is application for computers to read multiple types of items of information. In binary arithmetic, the number two is written as the number 10. For example, "10" indicates "one time the number, two and no more". The number "3," is written as "11" to mean "one times two and one more." The number "4" is written as "100," the number "5" as "101," "six" as "110," etc. An example of American Standard Code II (ASCII) for binary code is provided for the alphabet in lower and upper case in Table 1.

TABLE 2

| Decimal | 0 | 1 | 2 | 3 | 4 | 5 | 6 | 7 | 8 | 9 |
|---|---|---|---|---|---|---|---|---|---|---|
| Quaternary | 0 | 1 | 2 | 3 | 10 | 11 | 12 | 13 | 20 | 21 |
| Octal | 0 | 1 | 2 | 3 | 4 | 5 | 6 | 7 | 10 | 11 |
| Ternary | 0 | 1 | 2 | 10 | 11 | 12 | 20 | 21 | 22 | 100 |
| Binary | 0 | 1 | 10 | 11 | 100 | 101 | 110 | 111 | 1000 | 1001 |

Canonical DNA is a base 4 coding system, having four different nucleobases available: A, T, C or G (adenine, thymine, cytosine, and guanine). Thus, these 4 bases allow for a base 3 (using less than all), or a 4 base coding scheme. In addition, use of uracil (U), which is found in RNA, provides a fifth base and allows for a base 5 coding scheme. In addition, modified nucleobase may be used for a nucleic acid base coding greater than 4. Nucleobases that are not canonical DNA nucleobases or modified nucleobases include, without limitation, uracil, 3-meA (3-methyladenine), hypoxanthine, 8-oxoG (7,8-dihydro-8-oxoguanine), FapyG, FapyA, Tg (thymine glycol), hoU (hydroxyuracil), hmU (hydroxymethyluracil), fU (formyluracil), hoC (hydroxycytosine), fC (formylcytosine), 5-meC (5-methylcytosine), 6-meG (O6-methylguanine), 7-meG (N7-methylguanine), εC (ethenocytosine), 5-caC (5-carboxylcytosine), 2-hA, εA (ethenoadenine), 5-fU (5-fluorouracil), 3-meG (3-methylguanine), and isodialuric acid. Further provided herein are coding schemes where machine instructions pro-

TABLE 1

| Letter | ASCII Code | Binary | Letter | ASCII Code | Binary | Letter | ASCII Code | Binary |
|---|---|---|---|---|---|---|---|---|
| a | 97 | 1100001 | A | 65 | 1000001 | 0 | chr(0) | 00000000 |
| b | 98 | 1100010 | B | 66 | 1000010 | 1 | chr(1) | 00000001 |
| c | 99 | 1100011 | C | 67 | 1000011 | 2 | chr(2) | 00000010 |
| d | 100 | 1100100 | D | 68 | 1000100 | 3 | chr(3) | 00000011 |
| e | 101 | 1100101 | E | 69 | 1000101 | 4 | chr(4) | 00000100 |
| f | 102 | 1100110 | F | 70 | 1000110 | 5 | chr(5) | 00000101 |
| g | 103 | 1100111 | G | 71 | 1000111 | 6 | chr(6) | 00000110 |
| h | 104 | 1101000 | H | 72 | 1001000 | 7 | chr(7) | 00000111 |
| i | 105 | 1101001 | I | 73 | 1001001 | 8 | chr(8) | 00001000 |
| j | 106 | 1101010 | J | 74 | 1001010 | 9 | chr(9) | 00001001 |
| k | 107 | 1101011 | K | 75 | 1001011 | 10 | chr(10) | 00001010 |
| l | 108 | 1101100 | L | 76 | 1001100 | 11 | chr(11) | 00001011 |
| m | 109 | 1101101 | M | 77 | 1001101 | 12 | chr(12) | 00001100 |
| n | 110 | 1101110 | N | 78 | 1001110 | 13 | chr(13) | 00001101 |
| o | 111 | 1101111 | O | 79 | 1001111 | 14 | chr(14) | 00001110 |
| p | 112 | 1110000 | P | 80 | 1010000 | 15 | chr(15) | 00001111 |
| q | 113 | 1110001 | Q | 81 | 1010001 | 16 | chr(16) | 00010000 |
| r | 114 | 1110010 | R | 82 | 1010010 | 17 | chr(17) | 00010001 |
| s | 115 | 1110011 | S | 83 | 1010011 | 18 | chr(18) | 00010010 |
| t | 116 | 1110100 | T | 84 | 1010100 | 19 | chr(19) | 00010011 |
| u | 117 | 1110101 | U | 85 | 1010101 | 20 | chr(20) | 00010100 |
| v | 118 | 1110110 | V | 86 | 1010110 | 21 | chr(21) | 00010101 |
| w | 119 | 1110111 | W | 87 | 1010111 | 22 | chr(22) | 00010110 |
| x | 120 | 1111000 | X | 88 | 1011000 | 23 | chr(23) | 00010111 |
| y | 121 | 1111001 | Y | 89 | 1011001 | 24 | chr(24) | 00011000 |
| z | 122 | 1111010 | Z | 90 | 1011010 | 25 | chr(25) | 00011001 |
|  |  |  |  |  |  | 26 | chr(26) | 00011010 |
|  |  |  |  |  |  | 27 | chr(27) | 00011011 |
|  |  |  |  |  |  | 28 | chr(28) | 00011100 |
|  |  |  |  |  |  | 29 | chr(29) | 00011101 |
|  |  |  |  |  |  | 30 | chr(30) | 00011110 |

Provided herein are methods for converting information in the form of a first code, e.g., a binary sequence to a nucleic acid sequence. The process may involve direct conversion from a base 2 code (i.e., binary) to a base code that is higher. Exemplary base codes include 2, 3, 4, 5, 6, 7, 8, 9, 10 or more. Table 2 illustrates an exemplary alignment between various base numbering schemes. A computer receiving machine instructions for conversion, can automatically convert sequence information from one code to another.

vide for conversion of digital information in the form of a binary sequence into an intermediate code prior to ultimately being converted to the final nucleic acid sequence.

In some instances, to store data in a sequence of DNA, the information is converted from the 1s and 0s of binary code into the code of A, T, G, and C bases of DNA. In some instances, items of information are first encoded in a digital information form. In some cases, the binary code of digital information is converted into a biomolecule-based (e.g., DNA-based) code while preserved the information that the code represents. This converted code (digital binary code to a biomolecule code) is referred to herein as resulting in a "predetermined" sequence with respect to the deposit of a biomolecule disclosed herein on a surface disclosed herein. The predetermined sequence may encode sequence for a plurality of polynucleotides.

Nucleic Acid Sequence

Figure 2A:
FIGS. 2A-2C depict various polynucleotide sequence design schemes.
Figure 2A:
Figure 2A:
Figure 2A:
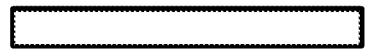
Figure 2B:
Figure 2B:
Figure 2B:
Figure 2B:
Figure 2B:
Figure 2C:
Figure 2C:
Figure 2C:
Figure 2C:
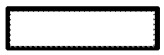
Figure 2C:
Figure 2C:
Figure 2C:
Figure 2C:
Figure 2C:
Figure 2C:

Provided herein are methods for designing a sequence for a polynucleotide described herein such that the nucleic acid sequence encodes for at least part of an item of information. In some instances, each polynucleotide sequence has design features to facilitate with sequence alignment during subsequent assembly steps and also to provide a means for error correction. In some arrangements, polynucleotide sequences are designed such that overlap exits between each polynucleotide sequence with another in the population. In some instances, each polynucleotide sequence overlaps with a portion of just one other polynucleotide sequence, FIG. 2A. In an alternative arrangement, each polynucleotide sequence region overlaps with two sequences such that 2 copies are generated for each sequence within a single polynucleotide, FIG. 2B. In yet another arrangement, each polynucleotide sequence region overlaps with more than two sequences such that 3 copies are generated for each sequence within a single polynucleotide, FIG. 2C. Sequences for polynucleotides described herein may encode for 10-2000, 10-500, 30-300, 50-250, or 75-200 bases in length. In some instances, each of the polynucleotides sequence is at least 10, 15, 20, 25, 30, 50, 100, 150, 200, 500 or more bases in length.

Figure 3A:
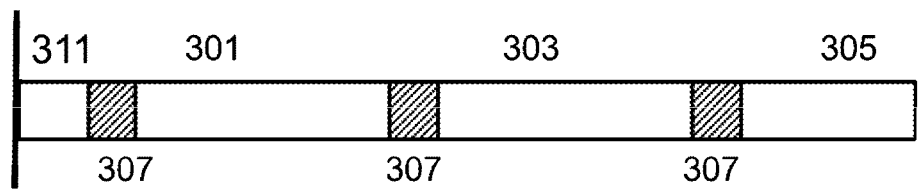
FIGS. 3A-3D depict various polynucleotide sequence design schemes.
Figure 3B:
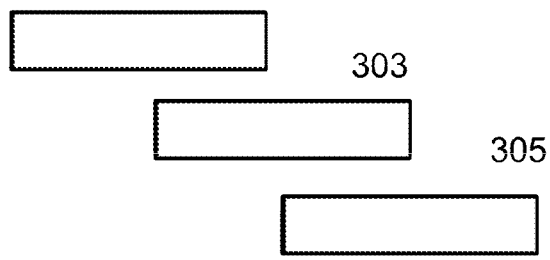
Figure 3C:
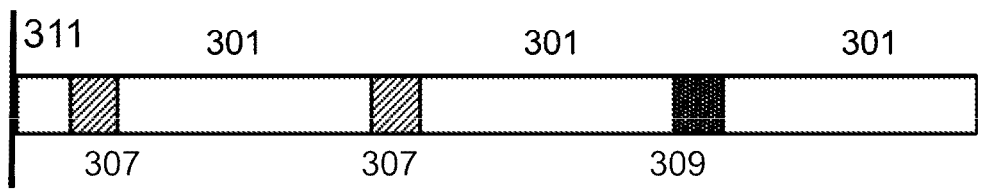
Figure 3D:
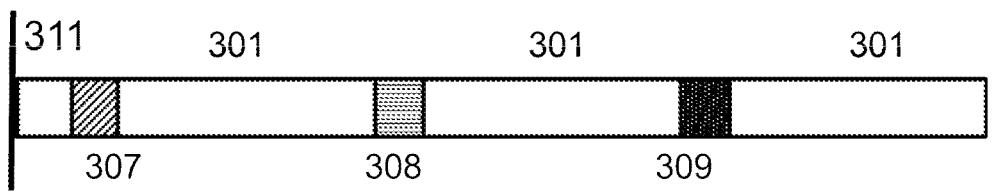

In some arrangements, each polynucleotide sequence described herein is designed to comprise a plurality of coding regions and a plurality of non-coding regions, FIG. 3A. In such an arrangement, each coding region (e.g., 301, 303, 305) encodes for at least a portion of an item of information. Optionally, each coding region in the same polynucleotide encodes for sequence from the same item of information, and an overlapping scheme is optionally employed as described herein, FIG. 3B. In further instances, each coding region in the same polynucleotide encodes for the same sequence, FIGS. 3C-3D. Sequences for polynucleotides described herein may encode for at least 1, 2, 3, 4, 5, 6, 7, 8, 9, 10, 11, 12, 13, 14, 15, 16, 17, 18, 19, 20 or more coding regions. Sequences for polynucleotides described herein may encode for at least 1, 2, 3, 4, 5, 6, 7, 8, 9, 10, 11, 12, 13, 14, 15, 16, 17, 18, 19, 20 or more of the same coding region. In some instances, each of the multiple coding regions is 10-1000, 20-500, 30-300, 50-250, or 75-200 bases in length. In some instances, each of the multiple coding regions is 25-500, 25-200, 50-300, 50-200, 75-150, 10-2000, 20-1000, or 25-500 bases in length. In some instances, each of the multiple coding regions is at least 10, 15, 20, 25, 30, 50, 100, 150, 200 or more bases in length. In some instances, each of the multiple coding regions is at least 10, 50, 100, 150, 200, 250, 300, 350, 400, 450, 500, 550, 600, 650, 700, 750, 800, 900, 1000, or more than 1000 bases. In some instances, each of the multiple coding regions is at most 10, 50, 100, 150, 200, 250, 300, 350, 400, 450, 500, 550, 600, 650, 700, 750, 800, 900, 1000, or more than 1000 bases. In some instances, each polynucleotide comprises a tether region 311 linking the molecule to the surface 302 of a structure.

In arrangements where multiple coding sequences are present in the same polynucleotide, a cleavage region 307 is optionally present in between each coding region. The cleavage region 307 may be present at the junction between each coding region, or may be present within an adaptor region having a string of sequence between each coding region. A cleavage region 307 may encode for a sequence feature, which will break from the strand subsequent to application of a cleavage signal. The cleavage region 307 may encode for a restriction enzyme recognition site, a modified nucleic acid that is light sensitive and will break under application of electromagnetic radiation (e.g., oligodeoxynucleotide heteropolymers carrying base-sensitive S-pivaloylthioethyl (t-Bu-SATE) phosphotriester linkages sensitive to light wavelengths of >300 nm), or modified nucleic acid that is sensitive to application of a certain chemical, e.g., Thymidine-succinyl hexamide CED phosphoramidite (CLP-2244 from ChemGenes) which breaks subsequent to application of ammonia gas. Because the design of a sequence to have a particular cleavage scheme may not be readily apparent from sequencing synthesized polynucleotides, the cleavage scheme provides a means for adding a level of security to sequence encoded by the synthesized nucleic acid library. Sequences for polynucleotides described herein may encode for at least 1, 2, 3, 4, 5, 6, 7, 8, 9, 10, 11, 12, 13, 14, 15, 16, 17, 18, 19, 20 or more cleavage regions. Sequences for polynucleotides described herein may encode for at least 1, 2, 3, 4, or 5 cleavage regions. In some instances, each of the cleavage region encodes for is 1-100, 1-50, 1-20, 1-10, 5-25, or 5-30 bases in length. In some instances, each of the cleavage region encodes for at least 1, 2, 3, 4, 5, 6, 7, 8, 9, 10, 11, 12, 13, 14, 15, 16, 17, 18, 19, 20, 25, 30, 40, 50, 100 or more bases. In some arrangements, for each polynucleotide, each coding region is identical and each cleavage region between each coding region is different. For example, a first cleavage region 307 is different from a second cleavage region 309. In some arrangements, the cleavage region 307 closest to the surface 302 is identical to the next distal cleavage region 307. In some instances, each coding region is different from each of the other coding region. For example, a first cleavage region 307 is different from a second cleavage region 309 and from a third cleavage region 308.

Provided herein are polynucleotide sequences designed to comprise a plurality of coding regions and a plurality of non-coding regions, wherein the non-coding regions vary in length and number. For example, sequences for polynucleotides described herein may comprise at least 1, 2, 3, 4, 5, 6, 7, 8, 9, 10, 11, 12, 13, 14, 15, 16, 17, 18, 19, 20 or more non-coding regions. Sequences for polynucleotides described herein may comprise at least 1, 2, 3, 4, 5, 6, 7, 8, 9, 10, 11, 12, 13, 14, 15, 16, 17, 18, 19, 20 or more of the same non-coding region. In some instances, each of the multiple non-coding regions is 10-1000, 20-500, 30-300, 50-250, or 75-200 bases in length. In some instances, each of the multiple non-coding regions is at least 1-100, 5-90, 10-80, 15-70, 20-60, 25-50, or 30-40 bases in length. In some instances, each of the multiple non-coding regions is at least 10, 15, 20, 25, 30, 50, 100, 150, 200 or more bases in length. In some instances, each of the multiple non-coding regions is at most 10, 15, 20, 25, 30, 50, 100, 150, 200, or more bases in length. In some instances, the non-coding regions are barcodes.

Figure 4A:
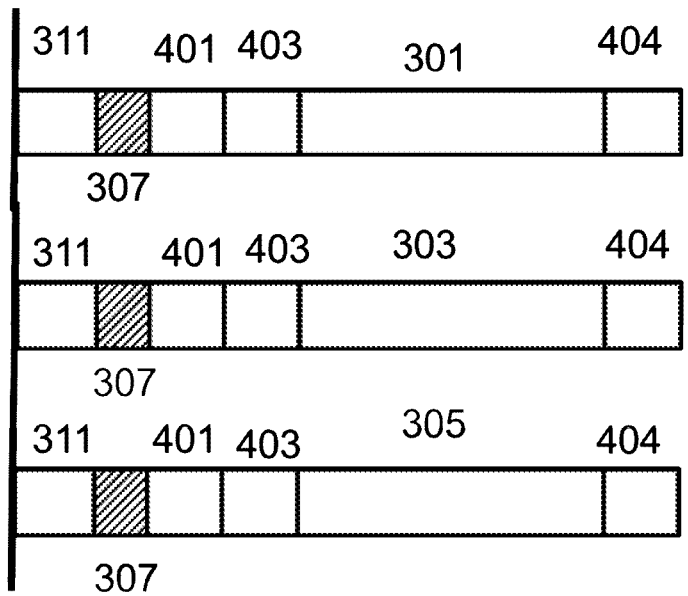
FIGS. 4A-4B depict a barcode design scheme.
Figure 4B:
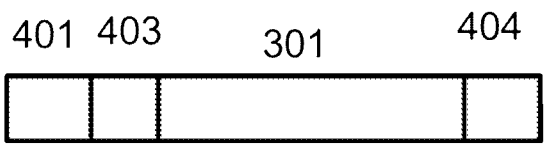
Figure 4B:
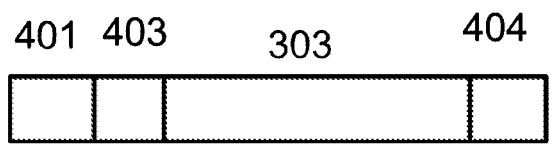
Figure 4B:
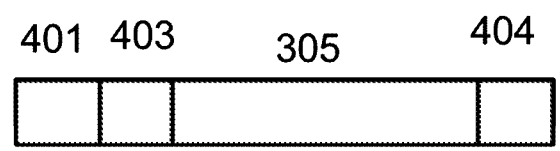

Barcodes are typically known nucleic acid sequences that allow some feature of a polynucleotide with which the barcode is associated to be identified. FIGS. 4A-4B provide an illustrative barcode arrangement. In FIG. 4A, each coding region for a first polynucleotide 301, a second polynucleotide 303, and a third polynucleotide 305, has the following features (from surface 302 outward): a tether region 302, a cleavage region 307, an first primer binding region 401, a barcode region 403, a coding region 301, 303, 305, and a second primer binding region 404. The polynucleotides may be amplified with the use of primers that recognize the first and/or second primer binding regions. Amplification may occur to polynucleotides attached to the surface or released from the surface (i.e., via cleavage at the cleavage region 307). After sequencing, the barcode region 403, provides an indicator for identifying a characteristic associated with the coding region. In some embodiments, a barcode comprises a nucleic acid sequence that when joined to a target polynucleotide serves as an identifier of the sample from which the target polynucleotide was derived. Barcodes can be designed at suitable lengths to allow sufficient degree of identification, e.g., at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, or more bases in length. Multiple barcodes, such as 2, 3, 4, 5, 6, 7, 8, 9, 10, or more barcodes, may be used on the same molecule, optionally separated by non-barcode sequences. In some embodiments, barcodes are shorter than 10, 9, 8, 7, 6, 5, or 4 bases in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some arrangements, a barcode, and the sample source with which it is associated, can be identified accurately after the mutation, insertion, or deletion of one or more bases in the barcode sequence, such as the mutation, insertion, or deletion of 1, 2, 3, 4, 5, 6, 7, 8, 9, 10, or more bases. In some embodiments, each barcode in a plurality of barcodes differ from every other barcode in the plurality at least three base positions, such as at least 3, 4, 5, 6, 7, 8, 9, 10, or more positions. Arrangements provided herein may include bar codes sequence that correspond the nucleic acid sequence to encode sequence for a particular region of a digital sequence. For example, a barcode sequence may indicate where in a large file a particular polynucleotide sequence encodes. In some instances, a barcode sequence may indicate which file a particular polynucleotide sequence is associated with. In some instances, a barcode sequence includes information associated with the conversion scheme for a particular sequence, providing an added layer of security.

Provided herein are polynucleotide sequence design schemes where each polynucleotide sequence acid in a population is designed to have at least one region in common amongst polynucleotide sequences in that population. For example, all polynucleotides in the same population may comprise one or more primer regions. The design of sequence-specific primer regions allows for the selection of polynucleotides to be amplified in selected batches from a large library of multiple polynucleotides. Each polynucleotide sequence may comprise at least 1, 2, 3, 4, 5, 6, 7, 8, 9, 10 or more primer binding sequences. A population of polynucleotide sequence may comprise at least 1, 2, 3, 4, 5, 6, 7, 8, 9, 10, 25, 50, 100, 200, 500, 1000, 5000, 10000, 50000, 100000 or more non-identical binding sequences. Primer binding sequences may comprise 5-100, 10-75, 7-60, 8-60, 10-50, or 10-40 bases in length.

Structures for Polynucleotide Synthesis

Figure 5:
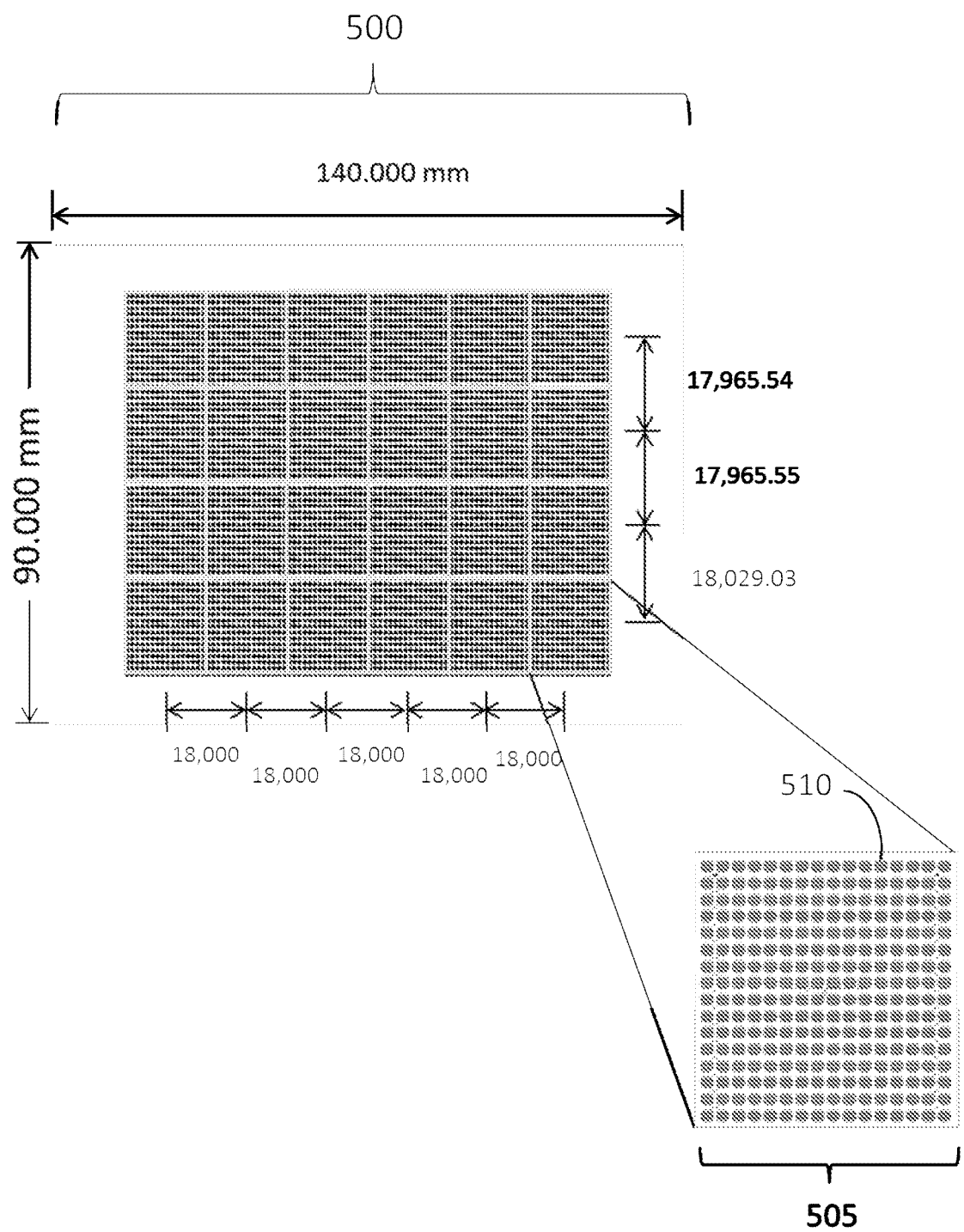
FIG. 5 illustrates a plate configured for polynucleotide synthesis comprising 24 regions, or sub-fields, each having an array of 256 clusters.
Figure 6:
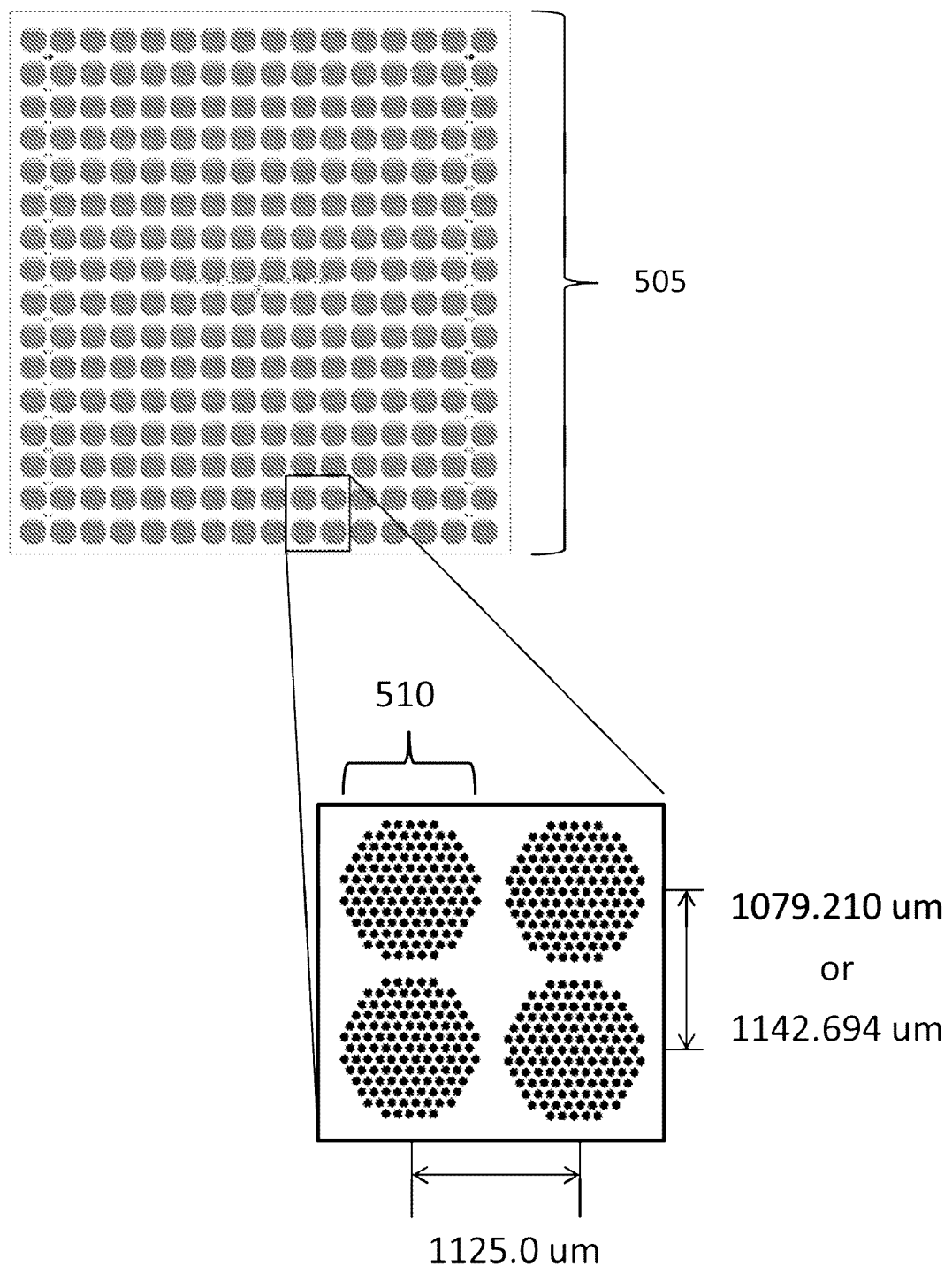
FIG. 6 illustrates a closer view of the sub-field in FIG. 5 having 16×16 of clusters, each cluster having 121 individual loci.
Figure 7:
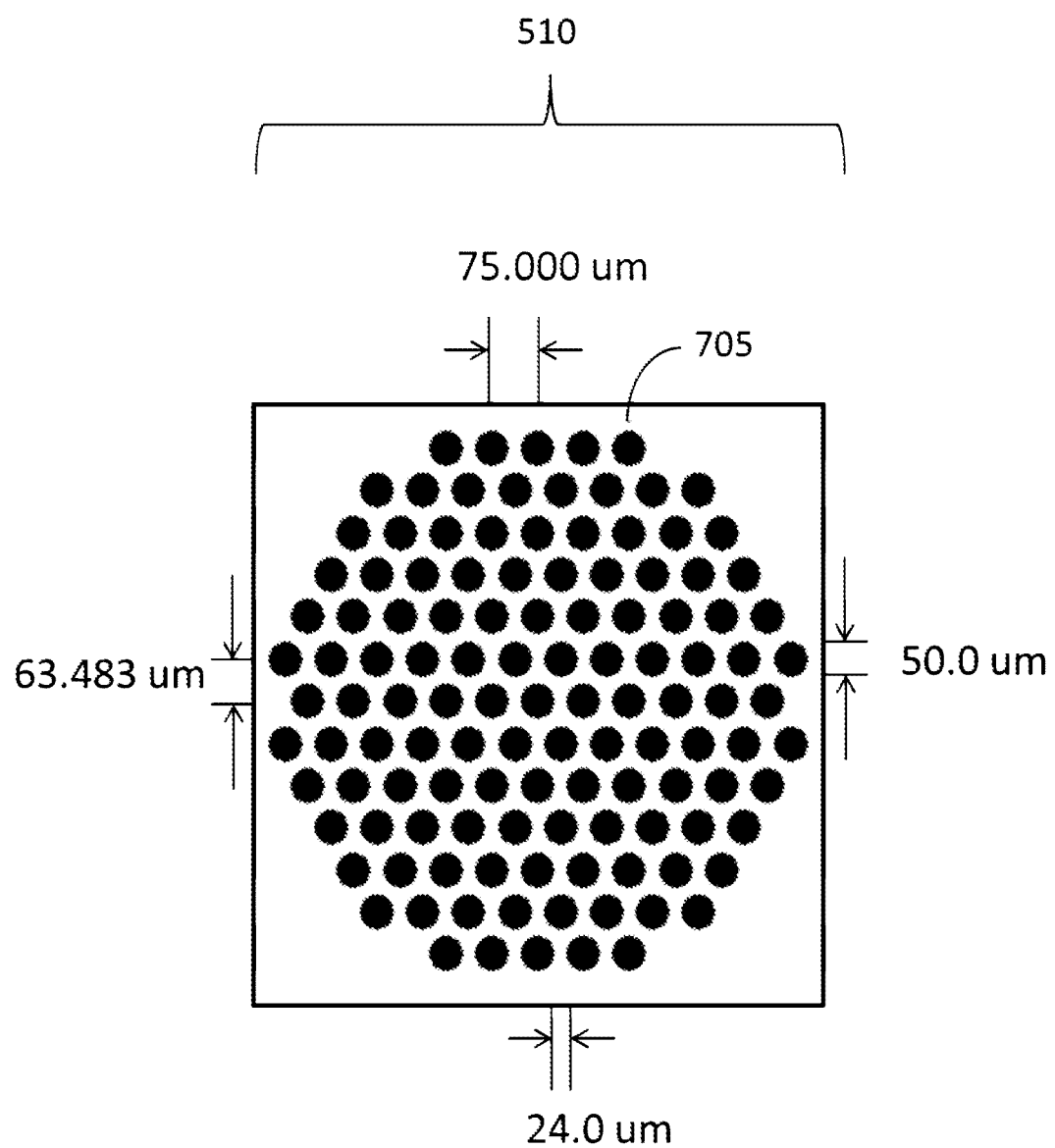
FIG. 7 illustrates a detailed view of the cluster in FIG. 5, where the cluster has 121 loci.6
Figure 8A:
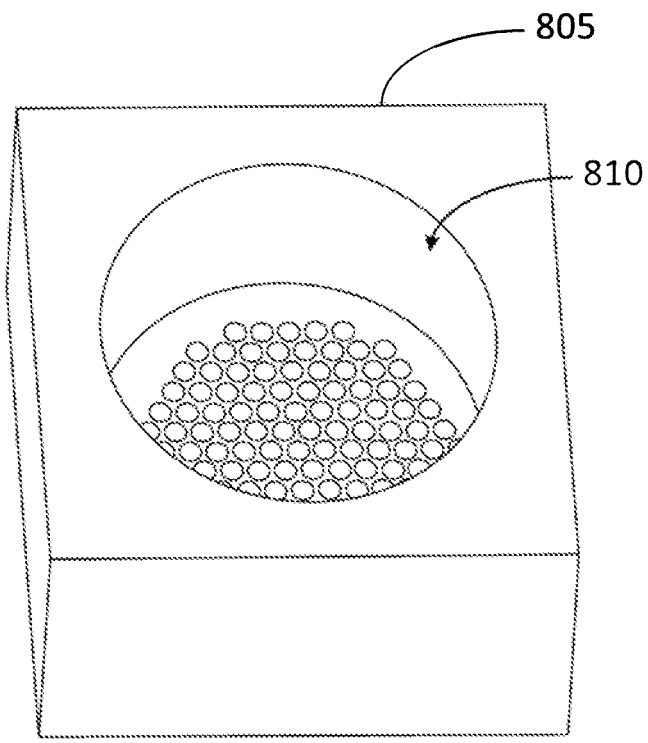
FIG. 8A illustrates a front view of a plate with a plurality of channels.
Figure 8B:
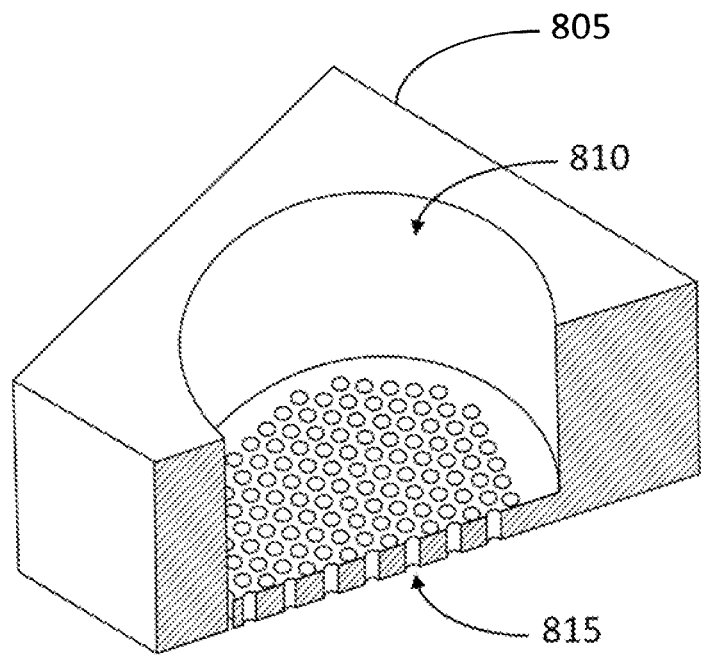
FIG. 8B illustrates a sectional view of plate with a plurality of channels.

Provided herein are rigid or flexibles structures for polynucleotide synthesis. In the case of rigid structures, provided herein are devices having a structure (e.g., a plate) for the generation of a library of polynucleotides. An exemplary structure 500 is illustrated in FIG. 5, wherein the structure 500 has about the same size dimensions as a standard 96 well plate: 140 mm by 90 mm. The structure 500 comprises clusters grouped in 24 regions or sub-fields 505, each sub-field 505 comprising an array of 256 clusters 510. An expanded view of an exemplary sub-field 505 is shown in FIG. 6. In the expanded view of four clusters (FIG. 6), a single cluster 510, has a Y axis cluster pitch (distance from center to center of adjacent clusters) of 1079.210 um or 1142.694 um, and an X axis cluster pitch of 1125 um. An illustrative cluster 510 is depicted in FIG. 7, where the Y axis loci pitch (distance from center to center of adjacent loci) is 63.483 um, and an X axis loci pitch is 75 um. The locus width at the longest part, e.g., diameter for a circular locus, is 50 um and the distance between loci is 24 um. The number of loci 705 in the exemplary cluster in FIG. 7 is 121. The loci may be flat, wells, or channels. An exemplary channel arrangement is illustrated in FIGS. 8A-8B where a plate 805 is illustrated comprising a main channel 810 and a plurality of channels 815 connected to the main channel 810. The connection between the main channel 810 and the plurality of channels 815 provides for a fluid communication for flow paths from the main channel 810 to the each of the plurality of channels 815. A plate 805 described herein can comprise multiple main channels 810. The plurality of channels 815 collectively forms a cluster within the main channel 810.

Figure 9A:
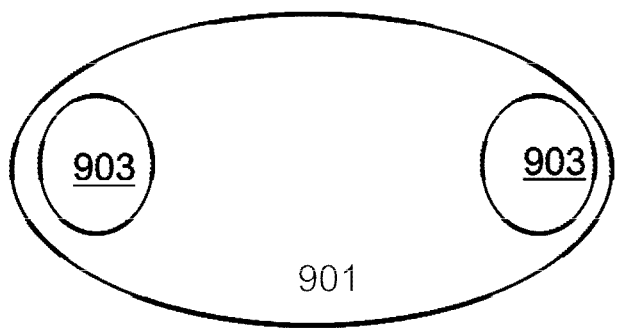
FIGS. 9A-9B depict a continuous loop and reel-to-reel arrangements for flexible structures.
Figure 9B:
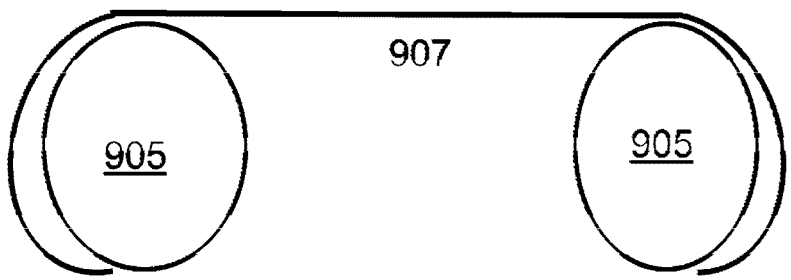
Figure 9C:
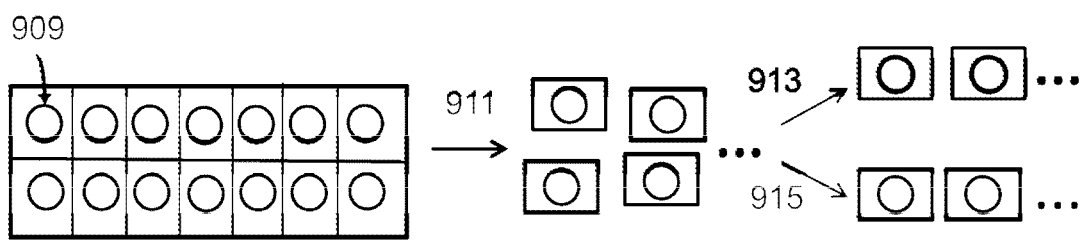
FIGS. 9C-9D depict schemas for release and extraction of synthesized polynucleotides.
Figure 9D:
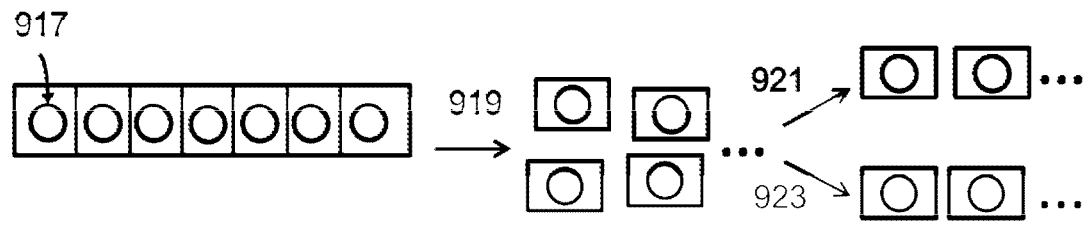
Figure 10A:
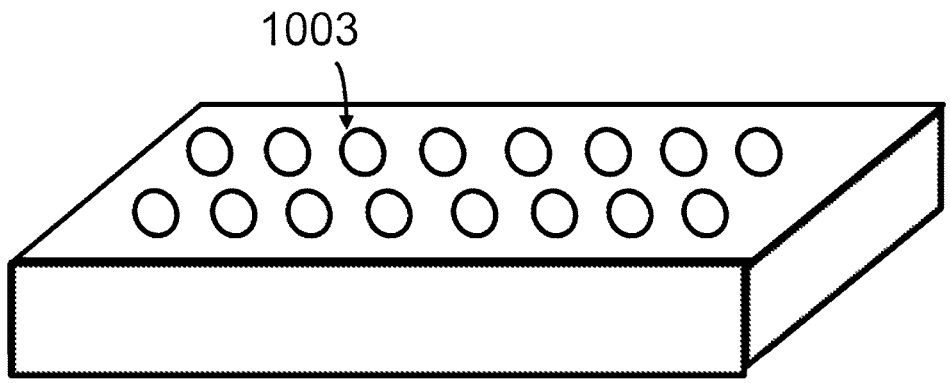
FIGS. 10A-10C depict a zoom in of a flexible structure, having spots, channels, or wells, respectively.
Figure 10B:
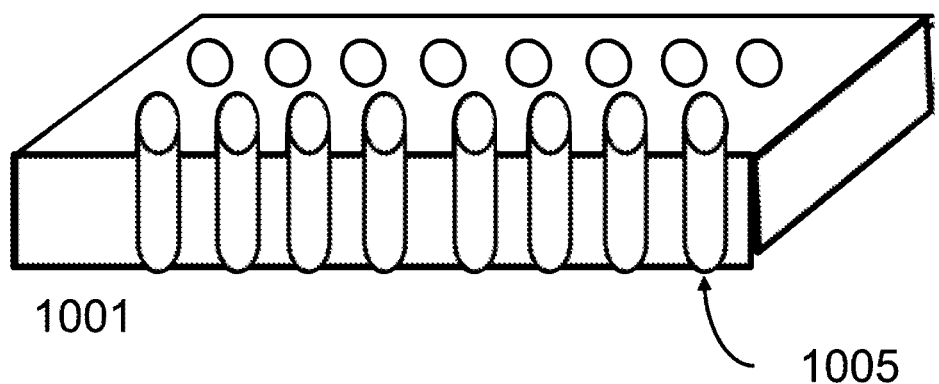
Figure 10C:
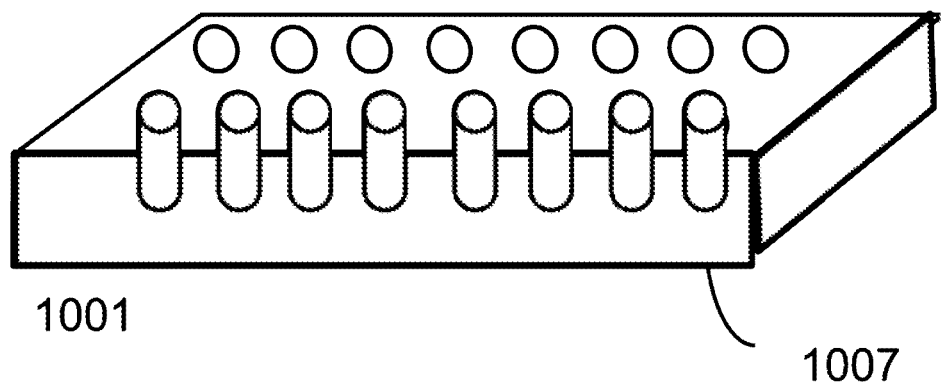

In the case of flexible structures, provided herein are devices wherein the flexible structure comprises a continuous loop 901 wrapped around one or more fixed structures, e.g., a pair of rollers 903 or a non-continuous flexible structure 907 wrapped around separate fixed structures, e.g., a pair reels 905. See FIGS. 9A-9B. In some instances, the structures comprise multiple regions for polynucleotide synthesis. An exemplary structure is illustrated in FIG. 9C where a plate comprises distinct regions 909 for polynucleotide synthesis. The distinct regions 909 may be separated 911 by breaking or cutting. Each of the distinct regions may be further released, sequenced, decrypted, and read 913 or stored 915. An alternative structure is illustrated in FIG. 9D in which a tape comprises distinct regions 917 for polynucleotide synthesis. The distinct regions 917 may be separated 919 by breaking or cutting. Each of the distinct regions may be further released, sequenced, decrypted, and read 921 or stored 923. Provided herein are flexible structures having a surface with a plurality of loci for polynucleotide extension. FIGS. 10A-10C show a zoom in of the locus in the flexible structure. Each locus in a portion of the flexible structure 1001, may be a substantially planar spot 1003 (e.g., flat), a channel 1005, or a well 1007. In one exemplary arrangement, each locus of the structure has a width of about 10 um and a distance between the center of each structure of about 21 um. See FIG. 11A. Loci may comprise, without limitation, circular, rectangular, tapered, or rounded shapes. Alternatively or in combination, the structures are rigid. In some instances, the rigid structures comprise loci, channels, or wells for polynucleotide synthesis.

In some instances, a channel described herein has a width to depth (or height) ratio of 1 to 0.01, wherein the width is a measurement of the width at the narrowest segment of the microchannel. In some instances, a channel described herein has a width to depth (or height) ratio of 0.5 to 0.01, wherein the width is a measurement of the width at the narrowest segment of the microchannel. In some instances, a channel described herein has a width to depth (or height) ratio of about 0.01, 0.05, 0.1, 0.15, 0.16, 0.2, 0.5, or 1.

Described herein are structures comprising a plurality of discrete loci, channels, or wells for polynucleotide synthesis.

In some instances, structures described herein are provided comprising a plurality of channels corresponding to a plurality of loci within a cluster, wherein the height or depth of the channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height of a channel is less than 100 um, less than 80 um, less than 60 um, less than 40 um or less than 20 um. In some cases, channel height is about 10, 20, 30, 40, 50, 60, 70, 80, 90, 100, 200, 300, 400, 500 μm or more. In some instances, the height or depth of the channel is at least 10, 25, 50, 75, 100, 200, 300, 400, 500, 600, 700, 800, 900, 1000, or more than 1000 nm. In some instances, the height or depth of the channel is in a range of about 10 nm to about 1000 nm, about 25 nm to about 900 nm, about 50 nm to about 800 nm, about 75 nm to about 700 nm, about 100 nm to about 600 nm, or about 200 nm to about 500.

In some instances, the width of a locus (e.g., substantially planar spot, well, or channel) is from about 0.1 um to about 500 um, from about 0.5 μm to about 500 um, from about 1 um to about 200 um, from about 1 um to about 100 um, from about 5 um to about 100 um, or from about 0.1 um to about 100 um, for example, about 90 um, 80 um, 70 um, 60 um, 50 um, 40 um, 30 um, 20 um, 10 um, 5 um, 1 um or 0.5 um. In some instances, the width of a locus (e.g., microchannel) is less than about 100 um, 90 um, 80 um, 70 um, 60 um, 50 um, 40 um, 30 um, 20 um or 10 um. In some instances, the width of a locus is at least 10, 25, 50, 75, 100, 200, 300, 400, 500, 600, 700, 800, 900, 1000, or more than 1000 nm. In some instances, the width of a locus is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the distance between the center of two adjacent loci is from about 0.1 um to about 500 um, 0.5 μm to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um. In some instances, the total width of a locus is about 5um, 10 um, 20 um, 30 um, 40 um, 50 um, 60 um, 70 um, 80 um, 90 um, or 100 um. In some instances, the total width of a locus is about 1 um to 100 um, 30 um to 100 um, or 50 um to 70 um.

In some instances, each locus supports the synthesis of a population of polynucleotides having a different sequence than a population of polynucleotides grown on another locus. Provided herein are surfaces which comprise at least 10, 100, 256, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In exemplary arrangements, each cluster includes 109, 121, 130 or 137 loci.

Provided herein are loci having a width at the longest segment of 5 to 100 um. In some cases, the loci have a width at the longest segment of about 30, 35, 40, 45, 50, 55 or 60 um. In some cases, the loci are channels having multiple segments, wherein each segment has a center to center distance apart of 5 to 50 um. In some cases, the center to center distance apart for each segment is about 5, 10, 15, 20 or 25 um.

In some instances, the number of distinct polynucleotides synthesized on the surface of a structure described herein is dependent on the number of distinct loci available in the substrate. In some instances, the density of loci within a cluster of a substrate is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$ or more. In some cases, a substrate comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some instances, the distance between the centers of two adjacent loci within a cluster is from about 10 um to about 500 um, from about 10 um to about 200 um, or from about 10 um to about 100 um. In some cases, the distance between two centers of adjacent loci is greater than about 10 um, 20 um, 30 um, 40 um, 50 um, 60 um, 70 um, 80 um, 90 um or 100 um. In some cases, the distance between the centers of two adjacent loci is less than about 200 um, 150 um, 100 um, 80 um, 70 um, 60 um, 50 um, 40 um, 30 um, 20 um or 10 um. In some cases, the distance between the centers of two adjacent loci is less than about 10000 nm, 8000 nm, 6000 nm, 4000 nm, 2000 nm 1000 nm, 800 nm, 600 nm, 400 nm, 200 nm, 150 nm, 100 nm, 80 um, 70 nm, 60 nm, 50 nm, 40 nm, 30 nm, 20 nm or 10 nm. In some embodiments, each square meter of a structure described herein allows for at least about $10^7$, $10^8$, $10^9$, $10^{10}$, $10^{11}$ loci, where each locus supports one polynucleotide. In some embodiments, $10^9$ polynucleotides are supported on less than about 6, 5, 4, 3, 2 or 1 $m^2$ of a structure described herein.

In some instances, a structure described herein provides support for the synthesis of more than 2,000; 5,000; 10,000; 20,000; 30,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more non-identical polynucleotides. In some cases, the structure provides support for the synthesis of more than 2,000; 5,000; 10,000; 20,000; 50,000; 100,000; 200,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; 10,000,000 or more polynucleotides encoding for distinct sequences. In some instances, at least a portion of the polynucleotides have an identical sequence or are configured to be synthesized with an identical sequence. In some instances, the structure provides a surface environment for the growth of polynucleotides having at least about 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more. In some arrangements, structures for polynucleotide synthesis described herein comprise sites for polynucleotide synthesis in a uniform arrangement.

In some instances, polynucleotides are synthesized on distinct loci of a structure, wherein each locus supports the synthesis of a population of polynucleotides. In some cases, each locus supports the synthesis of a population of polynucleotides having a different sequence than a population of polynucleotides grown on another locus. In some instances, the loci of a structure are located within a plurality of clusters. In some instances, a structure comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150 or more loci. In some instances, each cluster includes 50 to 500, 100 to 150, or 100 to 200 loci. In some instances, each cluster includes 109, 121, 130 or 137 loci. In some instances, each cluster includes 5, 6, 7, 8, 9, 10, 11 or 12 loci. In some instances, polynucleotides from distinct loci within one cluster have sequences that, when assembled, encode for a contiguous longer polynucleotide of a predetermined sequence.

Structure Size

In some instances, a structure described herein is about the size of a standard 96 well plate, for example between about 100 and 200 mm by between about 50 and 150 mm. In some instances, a structure described herein has a diameter less than or equal to about 1000 mm, 500 mm, 450 mm, 400 mm, 300 mm, 250 nm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 76 mm, 51 mm and 25 mm. In some instances, a substrate has a planar surface area of at least about 100 $mm^2$; 200 $mm^2$; 500 $mm^2$; 1,000 $mm^2$; 2,000 $mm^2$; 5,000 $mm^2$; 10,000 $mm^2$; 12,000 $mm^2$; 15,000 $mm^2$; 20,000 $mm^2$; 30,000 $mm^2$; 40,000 $mm^2$; 50,000 $mm^2$ or more. In some instances, the thickness is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples thickness include 275 mm, 375 mm, 525 mm, 625 mm, 675 mm, 725 mm, 775 mm and 925 mm. In some cases, the thickness of varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension.

Materials

Provided herein are devices comprising a surface, wherein the surface is modified to support polynucleotide synthesis at predetermined locations and with a resulting low error rate, a low dropout rate, a high yield, and a high oligo representation. In some embodiments, surfaces of devices for polynucleotide synthesis provided herein are fabricated from a variety of materials capable of modification to support a de novo polynucleotide synthesis reaction. In some cases, the devices are sufficiently conductive, e.g., are able to form uniform electric fields across all or a portion of the devices. Devices described herein may comprise a flexible material. Exemplary flexible materials include, without limitation, modified nylon, unmodified nylon, nitrocellulose, and polypropylene. Devices described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Devices disclosed herein may be fabricated from a material comprising silicon, polystyrene, agarose, dextran, cellulosic polymers, polyacrylamides, polydimethylsiloxane (PDMS), glass, or any combination thereof. In some cases, devices disclosed herein is manufactured with a combination of materials listed herein or any other suitable material known in the art.

Devices described herein may comprise material having a range of tensile strength. Exemplary materials having a range of tensile strengths include, but are not limited to, nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide synthesis that is in the form of a flexible material capable of being stored in a continuous loop or reel, such as a tape or flexible sheet.

Young's modulus measures the resistance of a material to elastic (recoverable) deformation under load. Exemplary materials having a range of Young's modulus stiffness include, but are not limited to, nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load. In some instances, a solid support described herein has a surface with a flexibility of at least nylon.

In some cases, devices disclosed herein comprises a silicon dioxide base and a surface layer of silicon oxide. Alternatively, the devices may have a base of silicon oxide. Surface of the devices provided here may be textured, resulting in an increase overall surface area for polynucleotide synthesis. Devices disclosed herein may comprise at least 5%, 10%, 25%, 50%, 80%, 90%, 95%, or 99% silicon. Devices disclosed herein may be fabricated from a silicon on insulator (SOI) wafer.

The structure may be fabricated from a variety of materials, suitable for the methods and compositions of the invention described herein. In certain embodiments, the materials from which the substrates/solid supports of the comprising the invention are fabricated exhibit a low level of oligonucleotide binding. In some situations, material that are transparent to visible and/or UV light can be employed. Materials that are sufficiently conductive, e.g. those that can form uniform electric fields across all or a portion of the substrates/solids support described herein, can be utilized. In some embodiments, such materials may be connected to an electric ground. In some cases, the substrate or solid support can be heat conductive or insulated. The materials can be chemical resistant and heat resistant to support chemical or biochemical reactions such as a series of oligonucleotide synthesis reaction. For flexible materials, materials of interest can include: nylon, both modified and unmodified, nitrocellulose, polypropylene, and the like.

For rigid materials, specific materials of interest include: glass; fuse silica; silicon, plastics (for example polytetraflouroethylene, polypropylene, polystyrene, polycarbonate, and blends thereof, and the like); metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

The term "flexible" is used herein to refer to a structure that is capable of being bent, folded or similarly manipulated without breakage. In some cases, a flexible structure is bent at least 30 degrees around a roller. In some cases, a flexible structure is bent at least 180 degrees around a roller. In some cases, a flexible structure is bent at least 270 degrees around a roller. In some instances, a flexible structure is bent about 360 degrees around a roller. In some cases, the roller is less than about 10 cm, 5 cm, 3 cm, 2 cm or 1 cm in radius. In some instances, the flexible structure is bent and straightened repeatedly in either direction at least 100 times without failure (for example, cracking) or deformation at 20° C. In some instances, a flexible structure described herein has a thickness that is amenable to rolling. In some cases, the thickness of the flexible structure described herein is less than about 50 mm, 10 mm, 1 mm, or 0.5 mm.

Exemplary flexible materials for structure described herein include, without limitation, nylon (unmodified nylon, modified nylon, clear nylon), nitrocellulose, polypropylene, polycarbonate, polyethylene, polyurethane, polystyrene, acetal, acrylic, acrylonitrile, butadiene styrene (ABS), polyester films such as polyethylene terephthalate, polymethyl methacrylate or other acrylics, polyvinyl chloride or other vinyl resin, transparent PVC foil, transparent foil for printers, Poly(methyl methacrylate) (PMMA), methacrylate copolymers, styrenic polymers, high refractive index polymers, fluorine-containing polymers, polyethersulfone, polyimides containing an alicyclic structure, rubber, fabric, metal foils, and any combination thereof. Various plasticizers and modifiers may be used with polymeric substrate materials to achieve selected flexibility characteristics.

Flexible structures described herein may comprise a plastic material. In some instances, the flexible structure comprises a thermoplastic material. Non-limiting examples of thermoplastic materials include acrylic, acrylonitrile butadiene styrene, nylon, polylactic acid, polybenzimidazole, polycarbonate, polyether sulfone, polyetherether ketone, polyetherimide, polyethylene, polyphenylene oxide, polyphenylene sulfide, polypropylene, polystyrene, polyvinyl chloride, and polytetrafluoroethylene. In some embodiments, the substrate comprises a thermoplastic material in the polyaryletherketone (PEAK) family. Non-limiting examples of PEAK thermoplastics include polyetherketone (PEK), polyetherketoneketone (PEKK), poly(ether ether ketone ketone) (PEEKK), polyether ether ketone (PEEK), and polyetherketoneetherketoneketone (PEKEKK). In some instances, the flexible structure comprises a thermoplastic material compatible with toluene. In some instances, the flexibility of the plastic material is increased by the addition of a plasticizer. An example of a plasticizer is an ester-based plasticizer, such as phthalate. Phthalate plasticizers include bis(2-ethylhexyl) phthalate (DEHP), diisononly phthalate (DINP), di-n-butyl phthalate (DnBP, DBP), butyl benzyl phthalate (BBzP), diisodecyl phthalate (DIDP), dioctyl phthalate (DOP, DnOP), diisooctyl phthalate (DIOP), diethyl phthalate (DEP), diisobutyl phthalate (DIBP), and di-n-hexyl phthalate. In some instances, modification of the thermoplastic polymer through copolymerization or through the addition of non-reactive side chains to monomers before polymerization also increases flexibility.

Provided herein are flexible structures which may further comprise a fluoroelastomer. Materials having about 80% fluoroelastomers are designated as FKMs. Fluoroelastomers include perfluoro-elastomers (FFKMs) and tetrafluoroethylene/propylene rubbers (FEPM). Fluoroelastomers have five known types. Type 1 FKMs are composed of vinylidene fluoride (VDF) and hexafluoropropylene (HFP) and their fluorine content typically is around 66% by weight. Type 2 FKMs are composed of VDF, HFP, and tetrafluoroethylene (TFE) and typically have between about 68% and 69% fluorine. Type 3 FKMs are composed of VDF, TFE, and perfluoromethylvinylether (PMVE) and typically have between about 62% and 68% fluorine. Type 4 FKMs are composed of propylene, TFE, and VDF and typically have about 67% fluorine. Type 5 FKMs are composed of VDF, HFP, TFE, PMVE, and ethylene.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some cases, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as a polynucleotide synthesis reaction. In some embodiments, the substrate is magnetic. In some instances, the structures comprise a metal or a metal alloy.

Structures for polynucleotide synthesis may be over 1, 2, 5, 10, 30, 50 or more feet long in any dimension. In the case of a flexible structure, the flexible structure is optionally stored in a wound state, e.g., in a reel. In the case of a large rigid structure, e.g., greater than 1 foot in length, the rigid structure can be stored vertically or horizontally.

Encryption Key Markings on the Structure's Surface

Provided herein are structures having markings 1101 wherein the markings provide information relating to the source item of information associated with a nearby population of polynucleotides, an encryption scheme for decrypting the sequence of the nearby population of polynucleotides, the copy number for the nearby population of polynucleotides, or any combination thereof. See, e.g., FIGS. 11B-11C. The markings may be visible to the naked eye, or visible under a magnified view using a microscope. In some instances, the markings on the surface are only visible after a treatment condition to expose the marking, such as a heat, chemical or light treatment (e.g., UV or IR light to illuminate the marking). An example ink developed by heat includes, without limitation, cobalt chloride, (which turns blue when heated). Example inks developed by chemical reaction include, without limitation, phenolphthalein, copper sulfate, lead (II) nitrate, cobalt (II) chloride, and cerium oxalate developed by manganese sulfate and hydrogen peroxide.

Surface Preparation

Provided herein are methods to support the immobilization of a biomolecule on a substrate, where a surface of a structure described herein comprises a material and/or is coated with a material that facilitates a coupling reaction with the biomolecule for attachment. To prepare a structure for biomolecule immobilization, surface modifications may be employed that chemically and/or physically alter the substrate surface by an additive or subtractive process to change one or more chemical and/or physical properties of a substrate surface or a selected site or region of the surface. For example, surface modification involves (1) changing the wetting properties of a surface, (2) functionalizing a surface, i.e. providing, modifying or substituting surface functional groups, (3) defunctionalizing a surface, i.e. removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. In some instances, the surface of a structure is selectively functionalized to produce two or more distinct areas on a structure, wherein at least one area has a different surface or chemical property that another area of the same structure. Such properties include, without limitation, surface energy, chemical termination, surface concentration of a chemical moiety, and the like.

In some instances, a surface of a structure disclosed herein is modified to comprise one or more actively functionalized surfaces configured to bind to both the surface of the substrate and a biomolecule, thereby supporting a coupling reaction to the surface. In some instances, the surface is also functionalized with a passive material that does not efficiently bind the biomolecule, thereby preventing biomolecule attachment at sites where the passive functionalization agent is bound. In some cases, the surface comprises an active layer only defining distinct loci for biomolecule support.

In some embodiments, the surface is contacted with a mixture of functionalization groups which are in any different ratio. In some embodiments, a mixture comprises at least 2, 3, 4, 5 or more different types of functionalization agents. In some cases, the ratio of the at least two types of surface functionalization agents in a mixture is about 1:1, 1:2, 1:5, 1:10, 2:10, 3:10, 4:10, 5:10, 6:10, 7:10, 8:10, 9:10, or any other ratio to achieve a desired surface representation of two groups. In some embodiments, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some embodiments, the mixture of functionalization reagents comprises one or more reagents that bind to a biomolecule and one or more reagents that do not bind to a biomolecule. Therefore, modulation of the reagents allows for the control of the amount of biomolecule binding that occurs at a distinct area of functionalization.

In some instances, a method for substrate functionalization comprises deposition of a silane molecule onto a surface of a substrate. The silane molecule may be deposited on a high energy surface of the substrate. In some instances the high surface energy region includes a passive functionalization reagent. Methods described herein provide for a silane group to bind the surface, while the rest of the molecule provides a distance from the surface and a free hydroxyl group at the end to which a biomolecule attaches. In some instances, the silane is an organofunctional alkoxysilane molecule. Non-limiting examples of organofunctional alkoxysilane molecules include dimethylchloro-octodecyl-silane, methyldichloro-octodecyl-silane, trichloro-octodecyl-silane, and trimethyl-octodecyl-silane, triethyl-octodecyl-silane. In some instances, the silane is an amino silane. Examples of amino silanes include, without limitation, 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances, the silane comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane, N-(3-triethoxysilylpropyl)-4-hydroxybutyramide, or any combination thereof. In some instances, an active functionalization agent comprises 11-acetoxyundecyltriethoxysilane. In some instances, an active functionalization agent comprises n-decyltriethoxysilane. In some cases, an active functionalization agent comprises glycidyloxypropyltriethoxysilane (GOPS). In some embodiments, the silane is a fluorosilane. In some embodiments, the silane is a hydrocarbon silane. In some cases, the silane is 3-iodo-propyltrimethoxysilane. In some cases, the silane is octylchlorosilane.

In some embodiments, silanization is performed on a surface through self-assembly with organofunctional alkoxysilane molecules. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). In some cases, the dimeric secondary aminoalkyl siloxanes is bis (3-trimethoxysilylpropyl) amine turning into bis(silyloxylpropyl)amine.

Active functionalization areas may comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane. In some instances, an active functionalization agent comprises 11-acetoxyundecyltriethoxysilane and n-decyltriethoxysilane in a ratio from about 20:80 to about 1:99, or about 10:90 to about 2:98, or about 5:95.

In some instances, functionalization comprises deposition of a functionalization agent to a structure by any deposition technique, including, but not limiting to, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD), physical vapor deposition (e.g., sputter deposition, evaporative deposition), and molecular layer deposition (MLD).

Any step or component in the following functionalization process be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a surface of a structure is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for surface functionalization optionally comprises a resist coat and a resist strip. In some instances, following active surface functionalization, the substrate is spin coated with a resist, for example, SPR™ 3612 positive photoresist. The process for surface functionalization, in various instances, comprises lithography with patterned functionalization. In some instances, photolithography is performed following resist coating. In some instances, after lithography, the surface is visually inspected for lithography defects. The process for surface functionalization, in some instances, comprises a cleaning step, whereby residues of the substrate are removed, for example, by plasma cleaning or etching. In some instances, the plasma cleaning step is performed at some step after the lithography step.

In some instances, a surface coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In some instances, the methods and compositions described herein relate to the application of photoresist for the generation of modified surface properties in selective areas, wherein the application of the photoresist relies on the fluidic properties of the surface defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Structures may be designed to control the flow of fluids by facilitating or inhibiting wicking effects into neighboring fluidic paths. For example, a structure is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

In some instances, a structure described herein has a surface that comprises a material having thickness of at least or at least about 0.1 nm, 0.5 nm, 1 nm, 2 nm, 5 nm, 10 nm or 25 nm that comprises a reactive group capable of binding nucleosides. Exemplary include, without limitation, glass and silicon, such as silicon dioxide and silicon nitride. In some cases, exemplary surfaces include nylon and PMMA.

In some instances, electromagnetic radiation in the form of UV light is used for surface patterning. In some instances, a lamp is used for surface patterning, and a mask mediates exposure locations of the UV light to the surface. In some instances, a laser is used for surface patterning, and a shutter opened/closed state controls exposure of the UV light to the surface. The laser arrangement may be used in combination with a flexible structure that is capable of moving. In such an arrangement, the coordination of laser exposure and flexible structure movement is used to create patterns of one or more agents having differing nucleoside coupling capabilities.

Material Deposition Systems

Provided herein are systems and devices for the deposition and storage of biomolecules on a structure described herein. In some embodiments, the biomolecules are polynucleotides that store encoded information in their sequences. In some embodiments, the system comprises a surface of a structure to support biomolecule attachment and/or a device for application of a biomolecule to the surface of the substrate. In an example, the device for biomolecule application is a polynucleotide synthesizer. In some embodiments, the system comprises a device for treating the substrate with a fluid, for example, a flow cell. In some embodiments, the system comprises a device for moving the substrate between the application device and the treatment device. For instances where the substrate is a reel-to-reel tape, the system may comprise two or more reels that allow for access of different portions of the substrate to the application and optional treatment device at different times.

Figure 12:
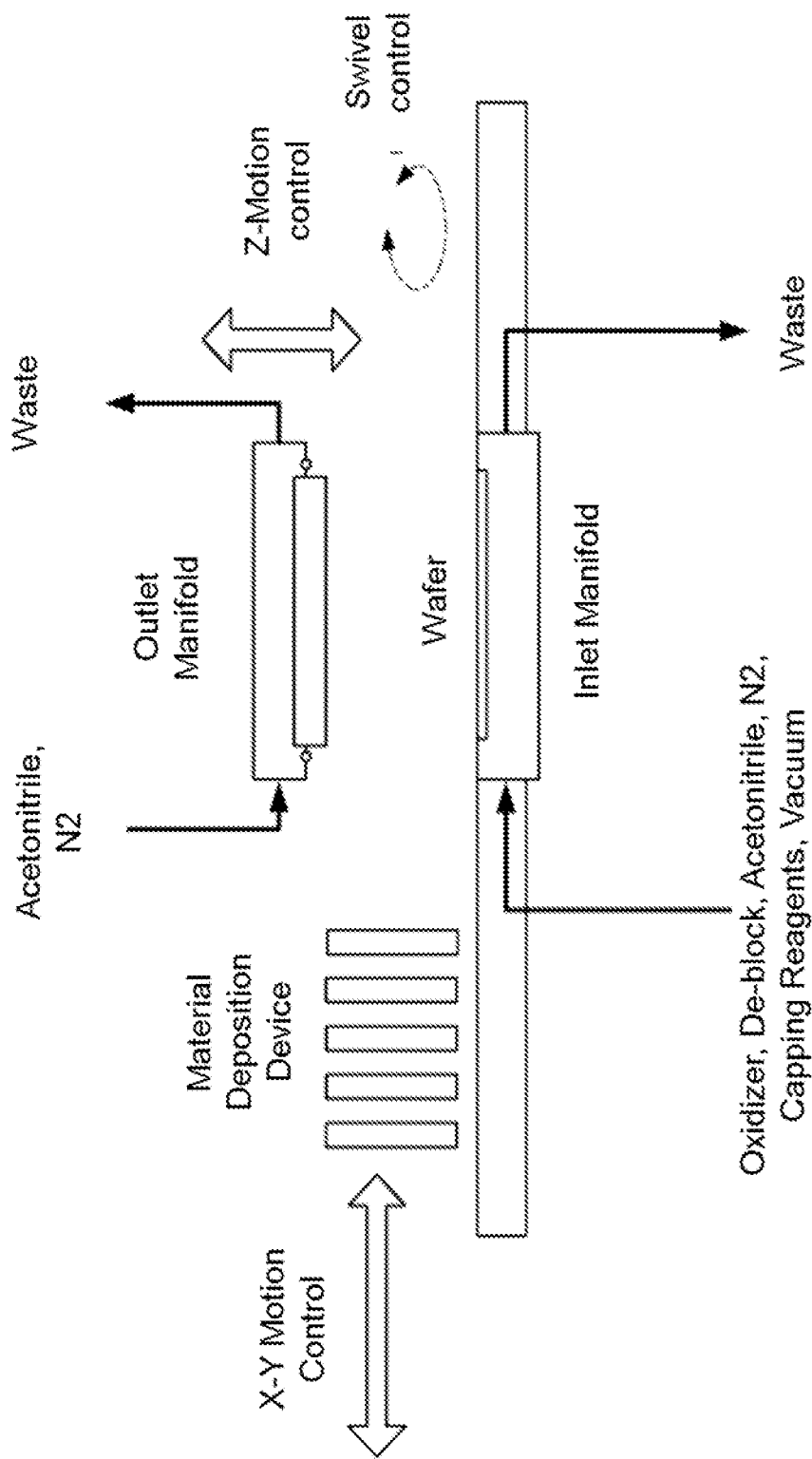
FIG. 12 illustrates a polynucleotide synthesis material deposition device.

A first example of a polynucleotide material deposition system for polynucleotide synthesis is shown in FIG. 12. The system includes a material deposition device that moves in the X-Y direction to align with the location of the substrate. The material deposition device can also move in the Z direction to seal with the substrate, forming a resolved reactor. A resolved reactor is configured to allow for the transfer of fluid, including polynucleotides and/or reagents, from the substrate to a capping element and/or vice versa. As shown in FIG. 12, fluid may pass through either or both the substrate and the capping element and includes, without limitation, coupling reagents, capping reagents, oxidizers, de-blocking agents, acetonitrile and nitrogen gas. Examples of devices that are capable of high resolution droplet deposition include the printhead of inkjet printers and laser printers. The devices useful in the systems and methods described herein achieve a resolution from about 100 dots per inch (DPI) to about 50,000 DPI; from about 100 DPI to about 20,000 DPI; from about 100 DPI to about 10,000 DPI; from about 100 DPI to about 5,000 DPI; from about 1,000 DPI to about 20,000 DPI; or from about 1,000 DPI to about 10,000 DPI. In some instances, the devices have a resolution at least about 1,000; 2,000; 3,000; 4,000; 5,000; 10,000; 12,000 DPI, or 20,000 DPI. The high resolution deposition performed by the device is related to the number and density of each nozzle that corresponds to a feature of the substrate.

Figure 13:
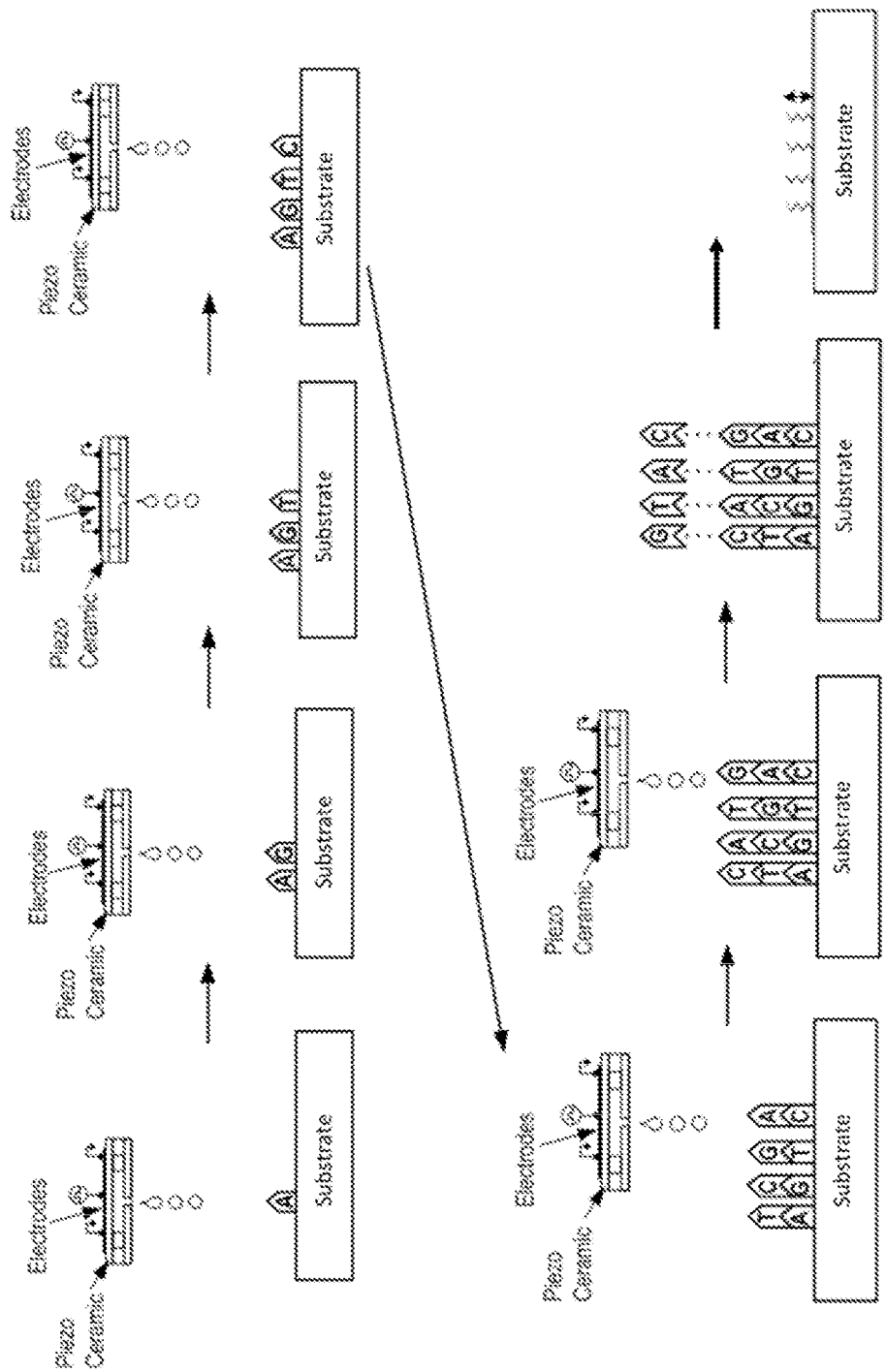
FIG. 13 illustrates a polynucleotide synthesis workflow.

An exemplary process workflow for de novo synthesis of a polynucleotide on a substrate using a polynucleotide synthesizer is shown in FIG. 13. Droplets comprising polynucleotide synthesis reagents are released from the material deposition device to the substrate in a stepwise manner, wherein the material deposition device has a piezo ceramic material and electrodes to convert electrical signals into a mechanical signal for releasing the droplets. The droplets are released to specific locations on the surface of the substrate one nucleobase at a time to generate a plurality of synthesized polynucleotides having predetermined sequences that encode data. In some cases, the synthesized polynucleotides are stored on the substrate. Nucleic acid reagents may be deposited on the substrate surface in a non-continuous, or drop-on-demand method. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some cases, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some cases, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl. The size of droplets dispensed by the device is correlated to the diameters of deposition nozzles, wherein each nozzle is capable of depositing a reagent onto a feature of the substrate. In some instances, a deposition device of a polynucleotide synthesizer comprises from about 100 to about 10,000 nozzles; from about 100 to about 5,000 nozzles; from about 100 to about 3,000 nozzles; from about 500 to about 10,000 nozzles; or from about 100 to about 5,000 nozzles. In some cases, the deposition device comprises greater than 1,000; 2,000; 3,000; 4,000; 5,000; or 10,000 nozzles. In some instances, each material deposition device comprises a plurality of nozzles, where each nozzle is optionally configured to correspond to a feature on a substrate. Each nozzle may deposit a reagent component that is different from another nozzle. In some instances, each nozzle deposits a droplet that covers one or more features of the substrate. In some embodiments, one or more nozzles are angled. In some embodiments, multiple deposition devices are stacked side by side to achieve a fold increase in throughput. In some cases, the gain is 2×, 4×, 8× or more. An example of a deposition device is Samba Printhead (Fujifilm). A Samba Printhead may be used with the Samba Web Administration Tool (SWAT).

The number of deposition sites may be increased by using and rotating the same deposition device by a certain degree or saber angle. By rotating the deposition device, each nozzle is jetted with a certain amount of delay time corresponding to the saber angle. This unsynchronized jetting creates a cross talk among the nozzles. Therefore, when the droplets are jetting at a certain saber angle different from 0 degrees, the droplet volume from the nozzle could be different.

In some arrangements, the configuration of a polynucleotide synthesis system allows for a continuous polynucleotide synthesis process that exploits the flexibility of a substrate for traveling in a reel-to-reel type process. This synthesis process operates in a continuous production line manner with the substrate travelling through various stages of polynucleotide synthesis using one or more reels to rotate the position of the substrate. In an exemplary embodiment, a polynucleotide synthesis reaction comprises rolling a substrate: through a solvent bath, beneath a deposition device for phosphoramidite deposition, through a bath of oxidizing agent, through an acetonitrile wash bath, and through a deblock bath. Optionally, the tape is also traversed through a capping bath. A reel-to-reel type process allows for the finished product of a substrate comprising synthesized polynucleotides to be easily gathered on a take-up reel, where it can be transported for further processing or storage.

In some arrangements, polynucleotide synthesis proceeds in a continuous process as a continuous flexible tape is conveyed along a conveyor belt system. Similar to the reel-to-reel type process, polynucleotide synthesis on a continuous tape operates in a production line manner, with the substrate travelling through various stages of polynucleotide synthesis during conveyance. However, in a conveyor belt process, the continuous tape revisits a polynucleotide synthesis step without rolling and unrolling of the tape, as in a reel-to-reel process. In some arrangements, polynucleotide synthesis steps are partitioned into zones and a continuous tape is conveyed through each zone one or more times in a cycle. For example, a polynucleotide synthesis reaction may comprise (1) conveying a substrate through a solvent bath, beneath a deposition device for phosphoramidite deposition, through a bath of oxidizing agent, through an acetonitrile wash bath, and through a block bath in a cycle; and then (2) repeating the cycles to achieve synthesized polynucleotides of a predetermined length. After polynucleotide synthesis, the flexible substrate is removed from the conveyor belt system and, optionally, rolled for storage. Rolling may be around a reel, for storage.

In an exemplary arrangement, a flexible substrate comprising thermoplastic material is coated with nucleoside coupling reagent. The coating is patterned into loci such that each locus has diameter of about 10 um, with a center-to-center distance between two adjacent loci of about 21 um. In this instance, the locus size is sufficient to accommodate a sessile drop volume of 0.2 pl during a polynucleotide synthesis deposition step. In some cases, the locus density is about 2.2 billion loci per m$^2$ (1 locus/441×10$^{-12}$ m$^2$). In some cases, a 4.5 m$^2$ substrate comprise about 10 billion loci, each with a 10 um diameter.

A material deposition device described herein may comprises about 2,048 nozzles that each deposit about 100,000 droplets per second at 1 nucleobase per droplet. For each deposition device, at least about 1.75×10$^{13}$ nucleobases are deposited on the substrate per day. In some instances, 100 to 500 nucleobase polynucleotides are synthesized. In some cases, 200 nucleobase polynucleotides are synthesized. Optionally, over 3 days, at a rate of about 1.75×10$^{13}$ bases per day, at least about 262.5×10$^9$ polynucleotides are synthesized.

In some arrangements, a device for application of one or more reagents to a substrate during a synthesis reaction is configured to deposit reagents and/or nucleotide monomers for nucleoside phosphoramidite based synthesis. Reagents for polynucleotide synthesis include reagents for polynucleotide extension and wash buffers. As non-limiting examples, the device deposits cleaning reagents, coupling reagents, capping reagents, oxidizers, de-blocking agents, acetonitrile, gases such as nitrogen gas, and any combination thereof. In addition, the device optionally deposits reagents for the preparation and/or maintenance of substrate integrity. In some embodiments, the polynucleotide synthesizer deposits a drop having a diameter less than about 200 um, 100 um, or 50 um in a volume less than about 1000, 500, 100, 50, or 20 pl. In some cases, the polynucleotide synthesizer deposits between about 1 and 10000, 1 and 5000, 100 and 5000, or 1000 and 5000 droplets per second.

In some arrangement, during polynucleotide synthesis, the substrate is positioned within and/or sealed within a flow cell. The flow cell may provide continuous or discontinuous flow of liquids such as those comprising reagents necessary for reactions within the substrate, for example, oxidizers and/or solvents. The flow cell may provide continuous or discontinuous flow of a gas, such as nitrogen, for drying the substrate typically through enhanced evaporation of a volatile substrate. A variety of auxiliary devices are useful to improve drying and reduce residual moisture on the surface of the substrate. Examples of such auxiliary drying devices include, without limitation, a vacuum source, depressurizing pump and a vacuum tank. In some cases, a polynucleotide synthesis system comprises one or more flow cells, such as 2, 3, 4, 5, 6, 7, 8, 9, 10, or 20 and one or more substrates, such as 2, 3, 4, 5, 6, 7, 8, 9, 10 or 20. In some cases, a flow cell is configured to hold and provide reagents to the substrate during one or more steps in a synthesis reaction. In some embodiments, a flowcell comprises a lid that slides over the top of a substrate and can be clamped into place to form a pressure tight seal around the edge of the substrate. An adequate seal includes, without limitation, a seal that allows for about 1, 2, 3, 4, 5, 6, 7, 8, 9 or 10 atmospheres of pressure. In some cases, the lid of the flow cell is opened to allow for access to an application device such as a polynucleotide synthesizer. In some cases, one or more steps of a polynucleotide synthesis method are performed on a substrate within a flow cell, without the transport of the substrate.

In some arrangements, a device for treating a substrate with a fluid comprises a spray bar. Nucleotide monomers may be applied onto a substrate surface then a spray bar sprays the substrate surface with one or more treatment reagents using spray nozzles of the spray bar. In some arrangements, the spray nozzles are sequentially ordered to correlate with different treatment steps during polynucleotide synthesis. The chemicals used in different process steps may be changed in the spray bar to readily accommodate changes in a synthesis method or between steps of a synthesis method. In some embodiments, the spray bar continuously sprays a given chemistry on a surface of a substrate as the substrate moves past the spray bar. In some cases, the spray bar deposits over a wide area of a substrate, much like the spray bars used in lawn sprinklers. In some embodiments, the spray bar nozzles are positioned to provide a uniform coat of treatment material to a given area of a substrate.

In some embodiments, a polynucleotide synthesis system comprises one or more elements useful for downstream processing of synthesized polynucleotides. As an example, the system comprises a temperature control element such as a thermal cycling device. In some embodiments, the temperature control element is used with a plurality of resolved reactors to perform nucleic acid assembly such as PCA and/or nucleic acid amplification such as PCR.

De Novo Polynucleotide Synthesis

Provided herein are systems and methods for synthesis of a high density of polynucleotides on a substrate in a short amount of time. In some instances, the substrate is a flexible substrate. In some instances, at least about 10$^{10}$, 10$^{11}$, 10$^{12}$, 10$^{13}$, 10$^{14}$, or 10$^{15}$ bases are synthesized in one day. In some instances, at least about 10×10$^8$, 10×10$^9$, 10×10$^{10}$, 10×10$^{11}$, or 10×10$^{12}$ polynucleotides are synthesized in one day. In some cases, each polynucleotide synthesized comprises at least about 20, 50, 100, 200, 300, 400 or 500 nucleobases. In some cases, these bases are synthesized with a total average error rate of less than about 1 in 100; 200; 300; 400; 500; 1000; 2000; 5000; 10000; 15000; 20000 bases. In some instances, these error rates are for at least 50%, 60%, 70%, 80%, 90%, 95%, 98%, 99%, 99.5%, or more of the polynucleotides synthesized. In some instances, these at least 90%, 95%, 98%, 99%, 99.5%, or more of the polynucleotides synthesized do not differ from a predetermined sequence for which they encode. In some instances, the error rate for synthesized polynucleotides on a substrate using the methods and systems described herein is less than about 1 in 200. In some instances, the error rate for synthesized polynucleotides on a substrate using the methods and systems described herein is less than about 1 in 1,000. In some instances, the error rate for synthesized polynucleotides on a substrate using the methods and systems described herein is less than about 1 in 2,000. In some instances, the error rate for synthesized polynucleotides on a substrate using the methods and systems described herein is less than about 1 in 3,000. In some instances, the error rate for synthesized polynucleotides on a substrate using the methods and systems described herein is less than about 1 in 5,000. Individual types of error rates include mismatches, deletions, insertions, and/or substitutions for the polynucleotides synthesized on the substrate. The term "error rate" refers to a comparison of the collective amount of synthesized polynucleotide to an aggregate of predetermined polynucleotide sequences. In some instances, synthesized polynucleotides disclosed herein comprise a tether of 12 to 25 bases. In some embodiments, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

A suitable method for polynucleotide synthesis on a substrate of this disclosure is a phosphoramidite method comprising the controlled addition of a phosphoramidite building block, i.e. nucleoside phosphoramidite, to a growing polynucleotide chain in a coupling step that forms a phosphite triester linkage between the phosphoramidite building block and a nucleoside bound to the substrate. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some embodiments, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is de-protected by removal of a protecting group, where the protecting group functions to prevent polymerization. A common protecting group is 4,4'-dimethoxytrityl (DMT).

Following coupling, phosphoramidite polynucleotide synthesis methods optionally comprise a capping step. In a capping step, the growing polynucleotide is treated with a capping agent. A capping step generally serves to block unreacted substrate-bound 5'-OH groups after coupling from further chain elongation, preventing the formation of polynucleotides with internal base deletions. Further, phosphoramidites activated with 1H-tetrazole often react, to a small extent, with the O6 position of guanosine. Without being bound by theory, upon oxidation with I$_2$/water, this side product, possibly via O6-N7 migration, undergoes depurination. The apurinic sites can end up being cleaved in the course of the final deprotection of the oligonucleotide thus reducing the yield of the full-length product. The O6 modifications may be removed by treatment with the capping reagent prior to oxidation with I$_2$/water. In some embodiments, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

Following addition of a nucleoside phosphoramidite, and optionally after capping and one or more wash steps, the substrate bound growing nucleic acid may be oxidized. The oxidation step comprises oxidizing the phosphite triester into a tetracoordinated phosphate triester, a protected precursor of the naturally occurring phosphate diester internucleoside linkage. In some instances, oxidation of the growing polynucleotide is achieved by treatment with iodine and water, optionally in the presence of a weak base such as a pyridine, lutidine, or collidine. Oxidation is sometimes carried out under anhydrous conditions using tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some embodiments, the step of oxidation is substituted with a sulfurization step to obtain oligonucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

In order for a subsequent cycle of nucleoside incorporation to occur through coupling, a protected 5' end of the substrate bound growing polynucleotide must be removed so that the primary hydroxyl group can react with a next nucleoside phosphoramidite. In some instances, the protecting group is DMT and deblocking occurs with trichloroacetic acid in dichloromethane. Conducting detritylation for an extended time or with stronger than recommended solutions of acids may lead to increased depurination of solid support-bound oligonucleotide and thus reduces the yield of the desired full-length product. Methods and compositions described herein provide for controlled deblocking conditions limiting undesired depurination reactions. In some instances, the substrate bound polynucleotide is washed after deblocking. In some cases, efficient washing after deblocking contributes to synthesized polynucleotides having a low error rate.

Methods for the synthesis of polynucleotides on the substrates described herein typically involve an iterating sequence of the following steps: application of a protected monomer to a surface of a substrate feature to link with either the surface, a linker or with a previously deprotected monomer; deprotection of the applied monomer so that it can react with a subsequently applied protected monomer; and application of another protected monomer for linking. One or more intermediate steps include oxidation and/or sulfurization. In some instances, one or more wash steps precede or follow one or all of the steps.

In some embodiments, polynucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of the substrate that provides support for polynucleotide synthesis may be chemically modified to allow for the synthesized polynucleotide chain to be cleaved from the surface. In some instances, the polynucleotide chain is cleaved at the same time as the polynucleotide is deprotected. In some cases, the polynucleotide chain is cleaved after the polynucleotide is deprotected. In an exemplary scheme, a trialkoxysilyl amine such as (CH3CH2O)3Si—(CH2)2-NH2 is reacted with surface SiOH groups of a substrate, followed by reaction with succinic anhydride with the amine to create an amide linkage and a free OH on which the nucleic acid chain growth is supported. Cleavage includes gas cleavage with ammonia or methylamine. In some instances, once released from the surface, polynucleotides are assembled into larger nucleic acids that are sequenced and decoded to extract stored information.

Assembly

Polynucleotides may be designed to collectively span a large region of a predetermined sequence that encodes for information. In some instances, larger polynucleotides are generated through ligation reactions to join the synthesized polynucleotides. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adapter sequences is amplified in a polymerase chain reaction (PCR) which includes modified primers that hybridize to the adapter sequences. In some cases, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA.

Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain embodiments, double-stranded nucleic acids with mismatches, bulges and small loops, chemically altered bases and/or other heteroduplexes are selectively removed from populations of correctly synthesized nucleic acids. In some embodiments, error correction is performed using proteins/enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Thermus aquaticus*) is used to remove failure products from a population of synthesized products. In some embodiments, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

Release, Extraction and Assembly

Provided herein are method and devices for replicable information storage. In some instances, multiple copies of the same coding region, the polynucleotide, the same cluster, the same portion of a structure comprising polynucleotides, or the entire structure comprising polynucleotides are synthesized. Where multiple copies of the same polynucleotide are synthesized, each of the polynucleotides may are attached to distinct regions of the surface. The distinct regions may be separated by breaking or cutting. Alternatively, each of the polynucleotides may be present at a locus in the form of a spot, well or channel and individually accessible. For example, contacting the locus with a cleavage reagent and then water would free one copy of the polynucleotide while leaving the other copies intact. Similarly, cleavage of polynucleotides in an entire region or over an entire plate allows for accessing a fraction of a replicate population. Replicate populations may exist in separated reels, plates, belts, and the like. In the case of a flexible material, such as a tape, a replicate region may be cut and the remaining regions of the tape may be spliced back together. Alternatively, nucleic acid information of the synthesized and stored polynucleotides may be obtained by performing amplification of polynucleotides attached to the surface of the structure using primers and a DNA polymerase.

In some instances, an aqueous or gaseous transfer media is deposited onto one or a plurality of channels in a structure to transfer the polynucleotides from the structure to a receiving unit. For example, a transfer media may pass through a channel in the structure to adhere to, collect and transfer a polynucleotide from a channel in the structure to a receiving unit. In some instance, a charge conducting feature and an applied voltage are employed to attract or repel a transfer media to or through a channel in the structure. In some instances, a slip is employed to direct a transfer media into a channel in the structure. In some cases a pressure release is employed to direct a transfer media into or through a channel in the structure. In some cases a nozzle is employed to form a localized area of high pressure which forces a transfer media into or through a channel in the structure. In some instances, a pin is employed to transfer a polynucleotide from a channel in the structure to a container to a receiving unit. In such instances, the pin may comprise agents to facilitate transfer media adhesion. In some cases a charge conducting feature is employed to attract or repel a transfer media to or through a channel in a structure, by forming a voltage potential between the conducting feature and the structure. In some cases, a pipette tip, or other capillary flow inducing structure, is used to transfer the fluid and polynucleotides via capillary flow. In some instances, a container comprises one or more compartments that each receives a portion of the transfer media, and the one or more polynucleotides therein, emitted from a single respective channel. In some instances, the container comprises a single compartment that receives one or more portions of the transfer media, each containing one or more polynucleotides therein, emitted from a one or more structure channels.

Figure 14A:
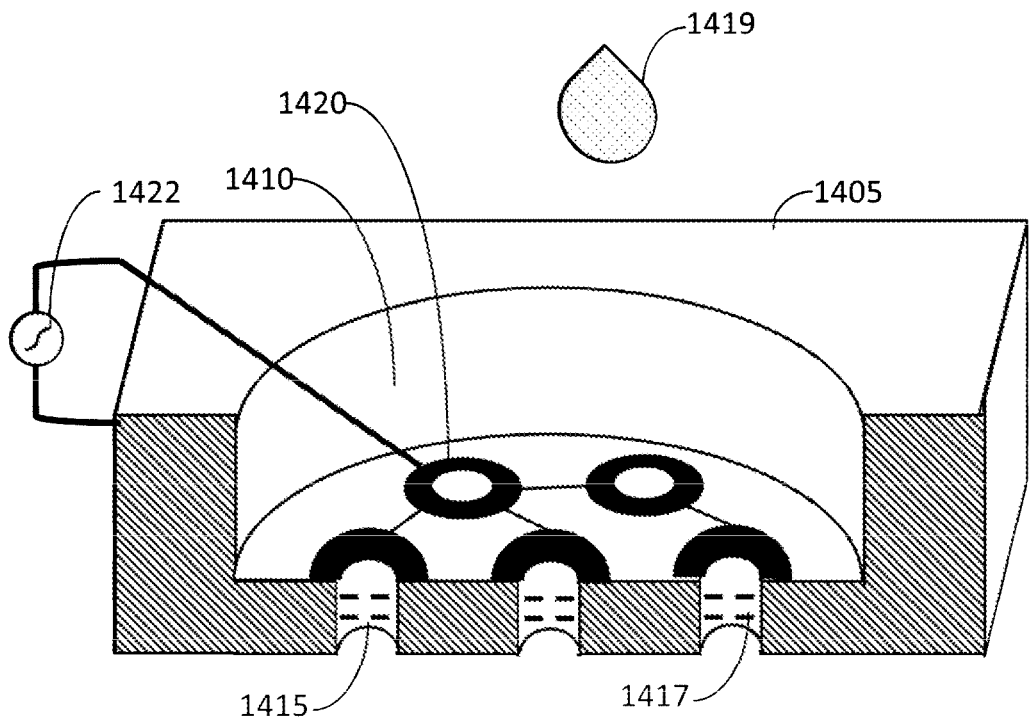
FIGS. 14A-14B illustrate a method for electrostatic deposition of a polynucleotide into a plurality of channels.
Figure 14B:
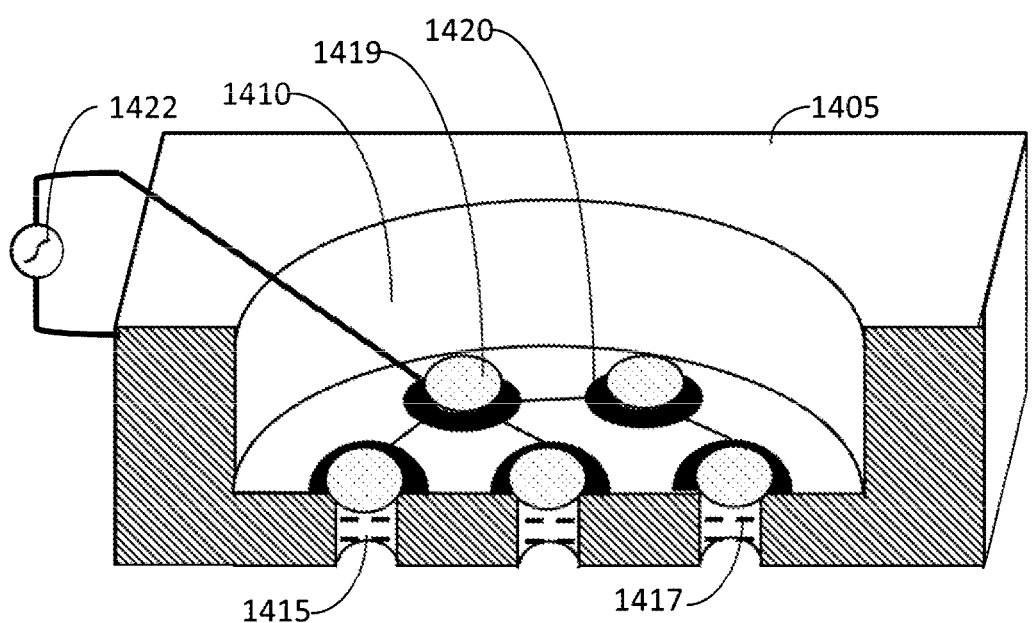

Referring to FIGS. 14A and 14B, a polynucleotide 1417 is transferred from a channel 1415 in a structure 1405 through the deposition of an aqueous or gaseous transfer media 1419, which adheres to a polynucleotide 1417, and wherein one or more interconnected conductor plates 1420 and a power unit 1422 direct the transfer media 1419 to the one or more channels respectively. In this arrangement, a series of one or more interconnected conductor plates 1420 are each located above, and surround, the proximal edge a respective channel 1415, and wherein a voltage potential imparted by a power unit 1422 between the interconnected conductor plates 1420 and the structure 1405, attracts the transfer media 1419 to the proximal opening of one or more channels 1415. As such, an exemplary method of attracting the transfer media 1419 to the proximal opening of the one or more channels 1415 in this instance comprises: depositing a transfer media 1419 into a main channel 1410 of a structure 1405, and applying a voltage potential between the interconnected conductor plates 1420 and the structure 1405, via a power unit 1422. Further, in this case, the transfer media 1419 may contain a positive or negative charge which reacts to an electrostatic or magnetic field or a potential difference created by the power unit 1422, as it passes through the structure 1405 and the channels 1415. Additionally, the electrostatic properties of the one or more conductor plates 1420 and the structure 1405 can be tuned to optimize the transfer of the polynucleotide 1417 within the transfer media 1419 through a channel 1415 in the structure. Finally, a nonconductive separator may be positioned between the structure 1405 and the one or more conductor plates 1420, to tune or optimize the electrostatic or magnetic field or the potential difference formed therein. Further, this case may additionally employ hydrophilic or hydrophobic structures on one or more faces of the main channel 1410 or on the interconnected conductor plates 1420 to more efficiently direct the transfer media 1419 into the channels 1415.

Figure 15A:
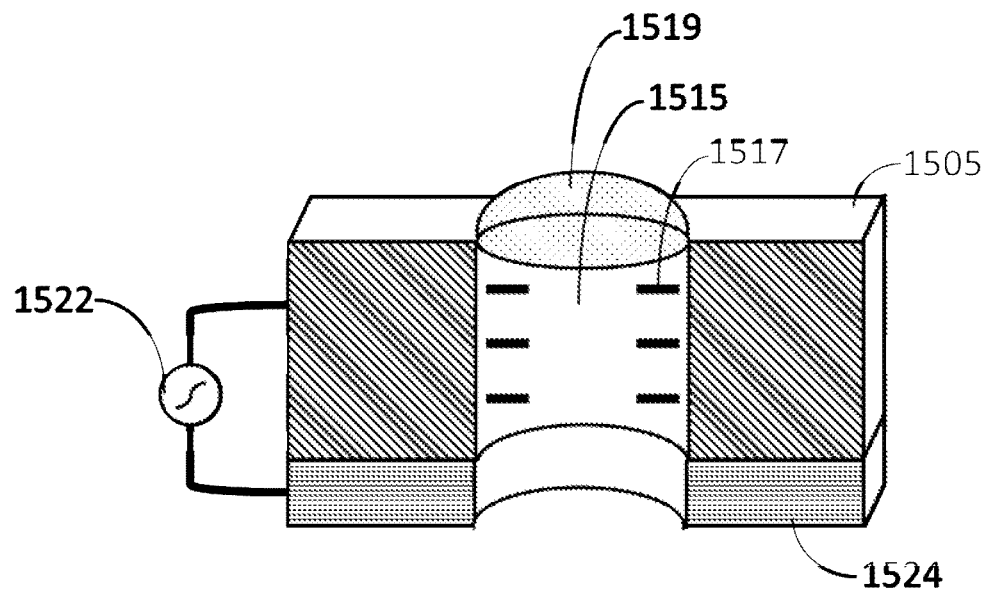
FIGS. 15A-15B illustrate an exemplary method for electrostatic transfer of a polynucleotide from a plurality of channels.
Figure 15B:
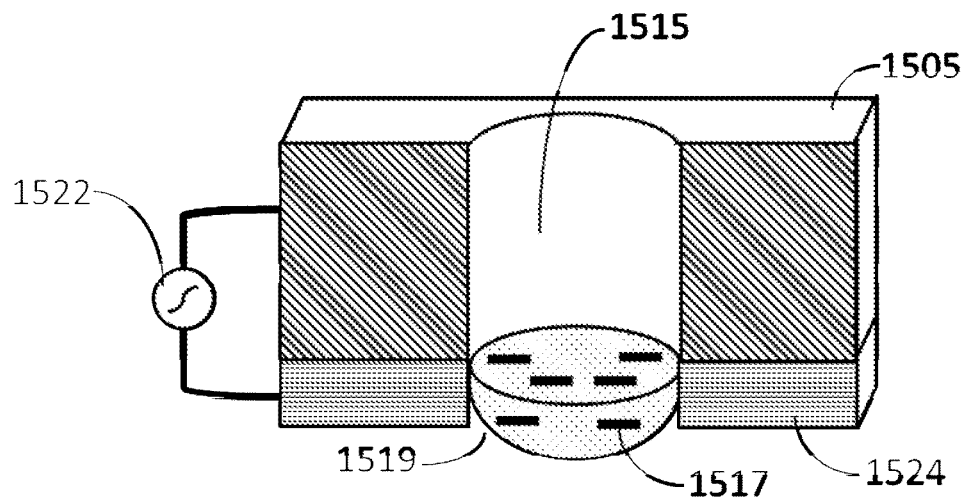

Referring to FIGS. 15A and 15B, a polynucleotide 1517 is transferred from a channel 1515 in a structure 1505, through the deposition of an aqueous or gaseous transfer media 1519 which adheres to one or more polynucleotides 1517, and wherein the transfer media 1519 is attracted through the one or more channels 1515 by one or more conducting sheets 1524 and a power unit 1522. In this arrangement, a conducting sheet 1524 below and surrounding the distal edge of a channel 1515, and a power unit 1522, are employed to attract the transfer media 1519 from the proximal opening of a channel 1515, see FIG. 15A, to the distal opening of that channel 1515, see FIG. 15B. As such, an exemplary method of attracting the transfer media 1519 to the distal opening of a channel 1515 in this instance comprises: applying a voltage potential between a conducting sheet 1524 and the structure 1505, via a power unit 1522. Further, in this case, the transfer media 1519 may contain a positive or negative charge which reacts to an electrostatic or magnetic field or a potential difference created by the power unit 1522, as it passes through the structure 1505, and the one or more conducting sheets 1524. Additionally, the electrostatic properties of the one or more conducting sheets 1524 and the structure 1505 can be tuned to optimize the transfer of the polynucleotides 1517 in the transfer media 1519 through a channel 1515 in the structure 1505. A nonconductive separator may be positioned between the structure 1505 and the one or more conducting sheets 1524, to tune or optimize the electrostatic or magnetic field or the potential difference formed therein.

Figure 16A:
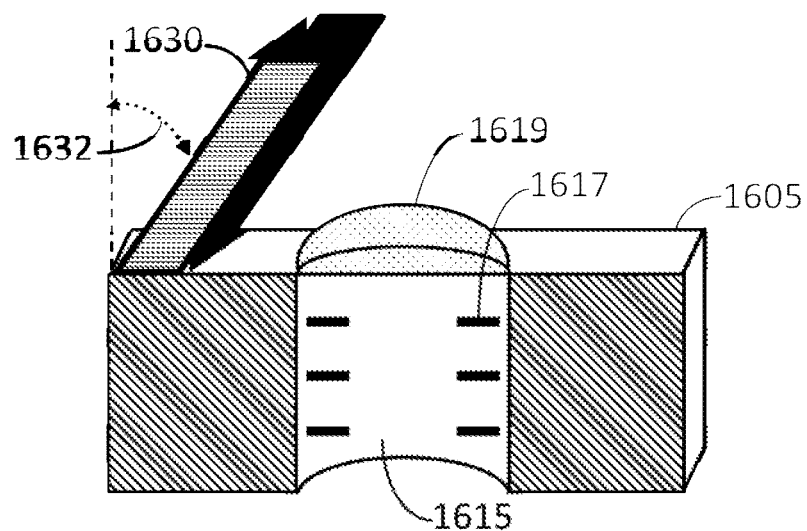
FIGS. 16A-16B illustrate a method for transfer of a polynucleotide from a plurality of channels, through a slip mechanism.
Figure 16B:
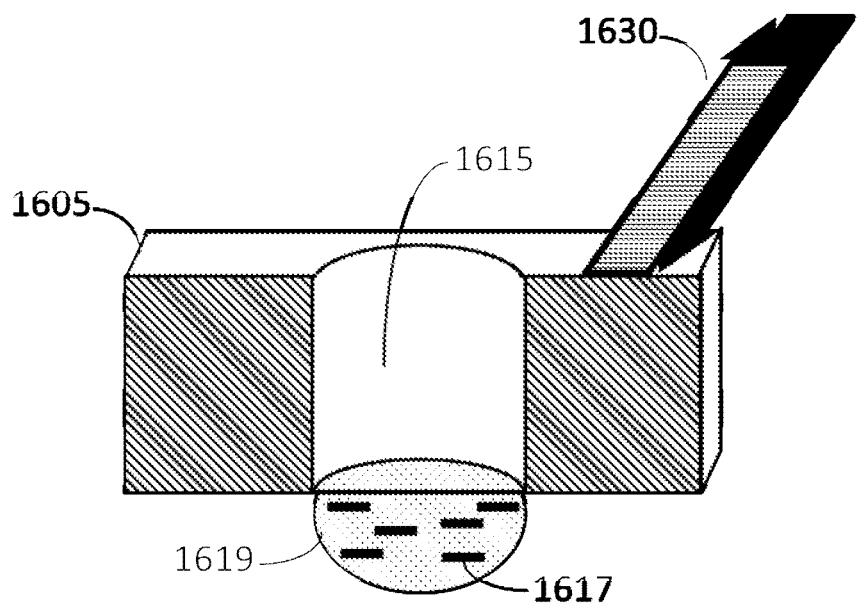

Referring to FIGS. 16A and 16B, a polynucleotide 1617 is transferred from a channel 1615 in a structure 1605, through the deposition of an aqueous or gaseous transfer media 1619 which adheres to a polynucleotide 1617, and wherein a slip 1630, in flush contact with the surface of, and positioned at an acute angle of attack 1632 relative to, a stationary plate structure 1605 or a moving non-continuous flexible structure, is employed to direct a transfer media into to the channels of the structure. In this arrangement, a slip 1630 is employed to direct the transfer media 1619 from the proximal opening of the one or more channels 1615, see FIG. 16A, to the distal opening of the respective channel 1615, see FIG. 16B. As such, an exemplary method of directing the transfer media 1619 through one or more channels 1615 in this instance comprises: translating or rotating the one or more slips 1630 relative to the structure 1605. In these instances the acute angle of attack 1632 may be equal to about 10°, 20°, 30°, 40°, 50°, 60°, 70° or about 80°. In some cases, a single slip 1630 or a rigid assembly of one or more slips 1630 is employed to direct the transfer media 1619 through the one or more channels 1615. In some cases, the relative velocity between the slip 1630 and the structure 1605 is up to about 1 centimeter/second. In some cases, the relative velocity between the slip 1630 and the structure 1605 is more than 1 centimeter/second. In some cases, the relative angular velocity between the slip 1630 relative to the structure 1605 is up to about 1 rotation/second. In some cases, the relative angular velocity between the slip 1630 and the structure 1605 is more than 1 rotation/second. In some cases, the slip 1630 can contort to partially enter the channel 1615. Finally, in this instance, the slip 1630 may be composed of any waterproof material comprising plastic, rubber, wood, metal, glass, fiberglass, carbon fiber or any combination thereof.

Figure 17A:
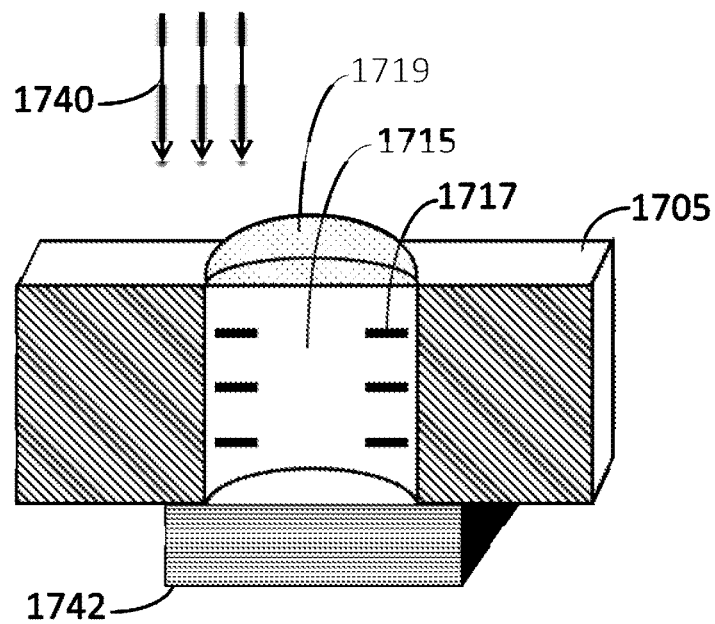
FIGS. 17A-17B illustrate a method for transfer of a polynucleotide from a plurality of channels, through a pressure release mechanism.
Figure 17B:
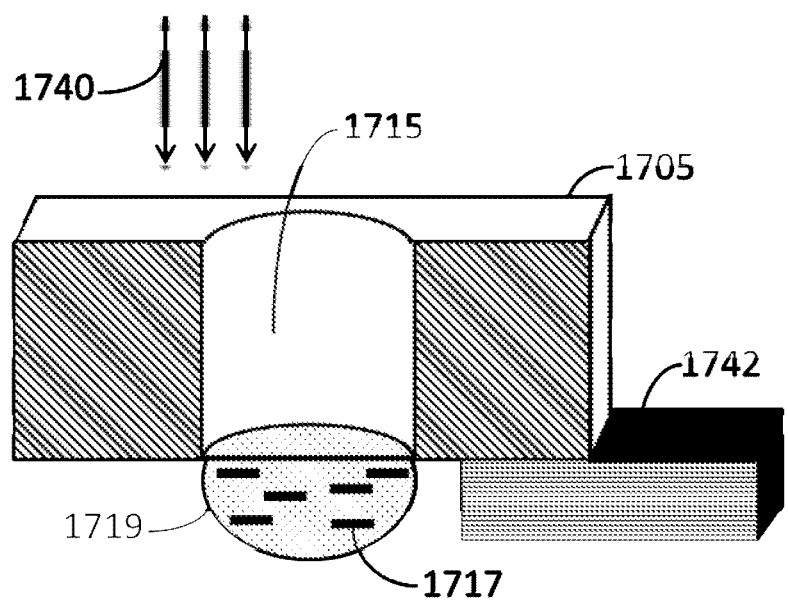

The case wherein a polynucleotide 1717 is transferred from a channel 1715 in a structure 1705, through the deposition of an aqueous or gaseous transfer media 1719 which adheres to a polynucleotide 1717, and wherein an applied pressure 1740 within a gas or fluid, and a pressure release 1742 are employed to force the transfer media 1719 through a channel 1715 in the structure 1705, is displayed in FIGS. 17A and 17B. In this instance, a pressure release 1742 block the applied pressure 1740, thus forming a pressure differential between distal edge a channel 1715, and the distal face a pressure release 1742, see FIG. 17A, which, when released by the opening of a pressure release 1742, forces the transfer media 1719 through a channel, see FIG. 17B. In some cases, a single pressure release 1742 is employed to direct the transfer media 1719 through one or more channels 1715 at once. As such, an exemplary method of directing the transfer media 1719 through a channel 1715 in this instance comprises: forming an applied pressure 1740 within the gas or fluid, and translating or rotating a pressure release 1742 relative to the structure 1705. In some cases, the relative velocity between the one or more pressure releases 1742 and the structure 705 is up to about 1 centimeter/second. In some cases, the relative velocity between the one or more pressure releases 1742 and the structure 1705 is more than 1 centimeter/second. In some arrangements, the relative rotational velocity between the one or more pressure releases 1742 and the structure 1705 is up to about 1 rotation/second. In some cases, the relative rotational velocity between the one or more pressure releases 1742 and the structure 1705 is more than 1 rotation/second. In some instances the pressure differential within the gas or fluid surrounding the structure 1705, created by the applied pressure 1740 is less than 1 atm. In some instances the pressure differential within the gas or fluid surrounding the structure 1705, created by the applied pressure 1740 is more than 1 atm.

Figure 18:
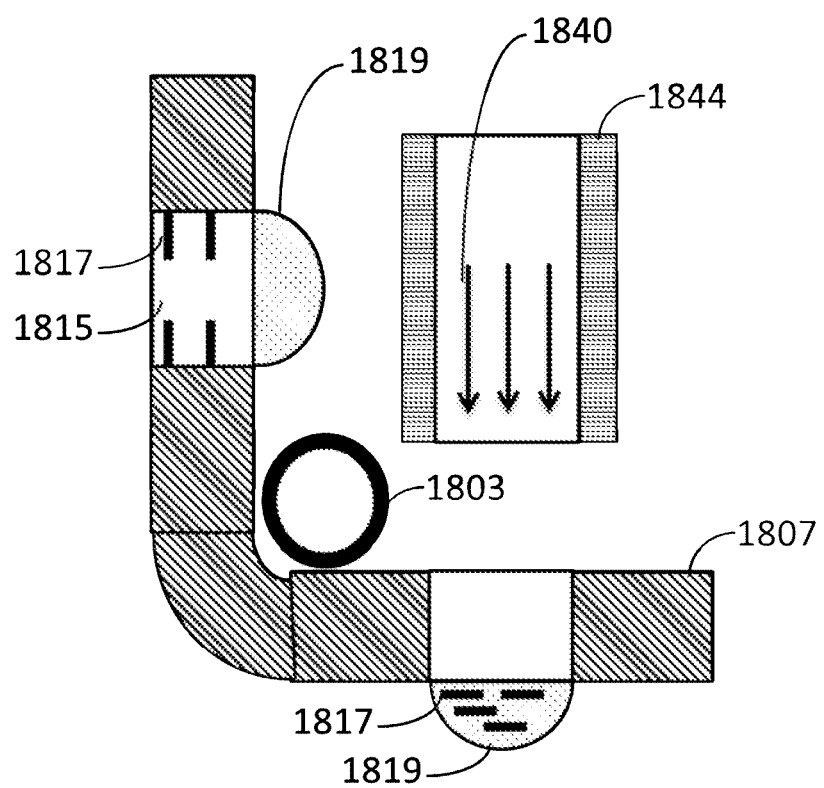
FIG. 18 illustrates a method for transfer of a polynucleotide from a plurality of channels in a flexible structure, through a nozzle mechanism.

Referring to FIG. 18, a polynucleotide 1817 is transferred from a channel 1815 in a moving non-continuous flexible structure 1807, through the deposition of an aqueous or gaseous transfer media 1819 which adheres a polynucleotide 1817, and wherein a nozzle 1844 and an applied pressure 1840, are employed to force a transfer media 1819 through a channel 1815 in the structure 1807. As such, an exemplary method of directing the transfer media 1819 through a channel 1815 in this instance comprises: translating the continuous flexible structure 1807, about a roller 1803 such that a channel 1815 is aligned below a nozzle 1844, and triggering a nozzle 1844 to direct an applied pressure 1840 towards a channel 1815. In some instances, the pressure differential within the gas or fluid surrounding the structure 1807 imparted by a nozzle 1844 is less than 1 atm. In some instances the pressure differential within the gas or fluid surrounding the structure 1807 imparted by a nozzle 1844 is more than 1 atm.

Figure 19A:
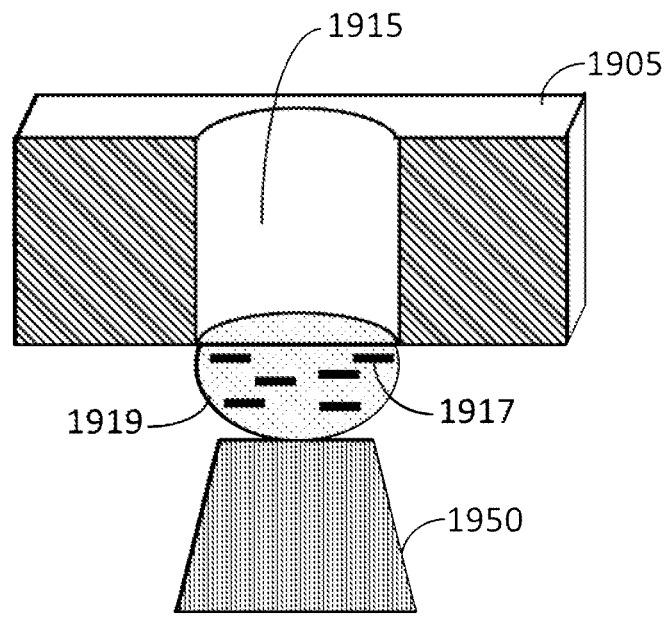
FIGS. 19A-19B illustrate a method for capture of a polynucleotide from a plurality of channels, through a pin.
Figure 19B:
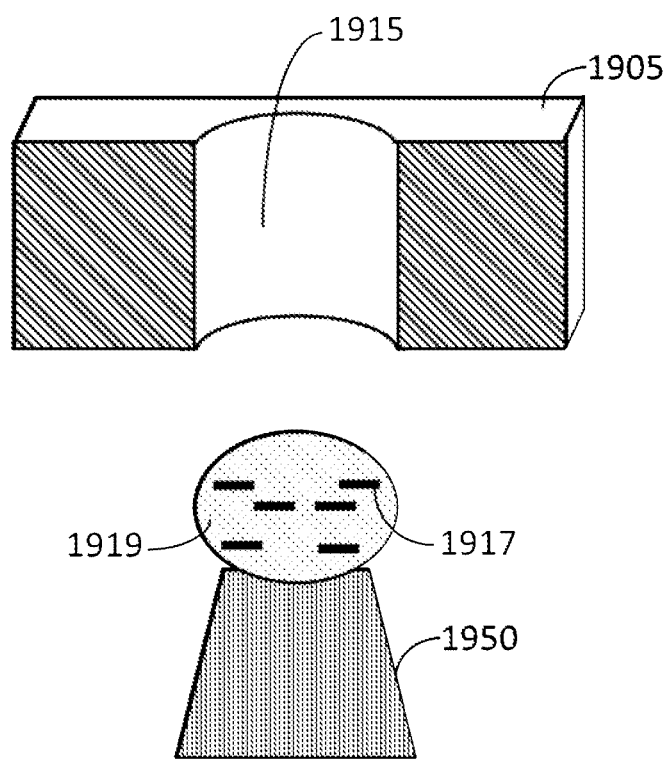

Referring to FIGS. 19A and 19B, a polynucleotide 1917 is transferred from a channel 1915 in a structure 1905, through the deposition of an aqueous or gaseous transfer media 1919, and wherein a pin 1950 adheres to the transfer media 1919, and a polynucleotide 1917 within, to remove the transfer media 1919 from a channel 1915 in the structure 1905 is shown in FIGS. 19A and 19B. In this instance, the pin 1950 contacts and attracts the transfer media 1919, see FIG. 19A, wherein the attraction of the transfer media 1919 to the pin 1950 is greater than the transfer media's 1919 attraction to the distal edge of a channel 1915, and wherein a relative vertical motion between the pin 1950 and the structure 1905 dislocates the transfer media 1919 from the structure 1905, see FIG. 19B. In such instances, the pin 1950 may comprise features to facilitate transfer media adhesion comprising hydrophilic or gas-philic structures or coatings, or a binding chemical coating. In some instances, the pin 1950 is comprised of any hard material comprising metal, plastic, rubber, carbon fiber, wood, fiberglass or any combination thereof. In other instances, the pin 1950 is comprised of a conductive material capable of conducting an electric, electrostatic or magnetic charge or field to attract the transfer media 1919. In some cases, the relative velocity between the pin 1950 and the structure 1905 is up to about 1 centimeter/second. In some cases, the relative velocity between the pin 1950 and the structure 1905 is more than 1 centimeter/second.

Figure 20A:
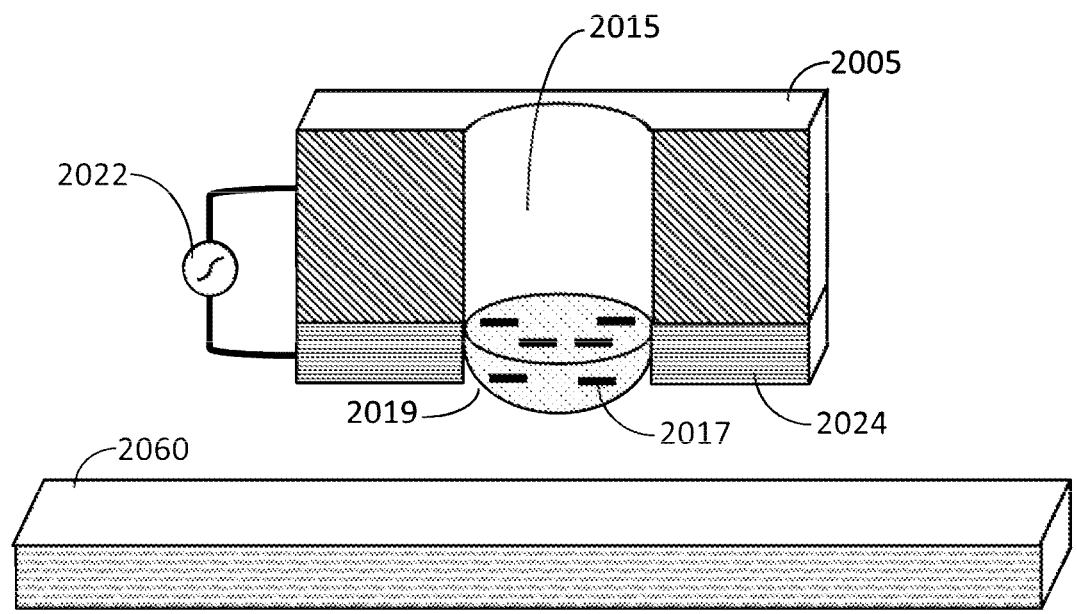
FIGS. 20A-20B illustrate a method for electrostatic capture of a polynucleotide from a plurality of channels.
Figure 20B:
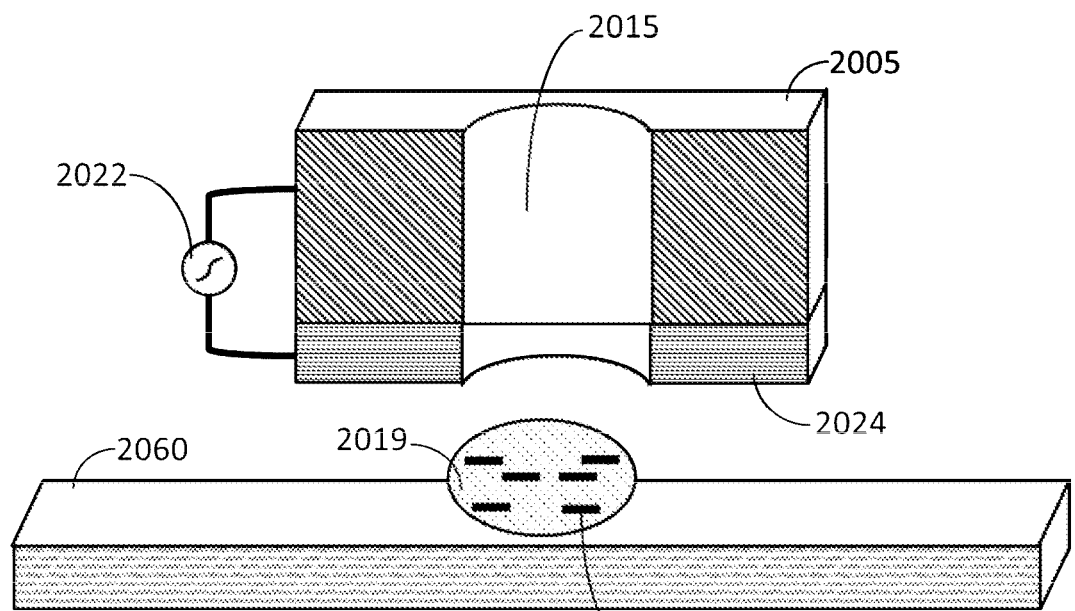

Referring to FIGS. 20A and 20B, a polynucleotide 2017 is transferred from a channel 2015 in a structure 2005 through the deposition of an aqueous or gaseous transfer media 2019, and wherein the transfer media 2019 is repelled from a channel in the structure 2005 to a receiving unit 2060, by a voltage applied from a power unit 2022 to a conducting sheet 2024. In this instance, a conducting sheet 2024 below and surrounding the distal edge of a channel 2015, and a power unit 2022 are employed to repel the transfer media 2019 from the distal opening of a channel 2015, see FIG. 20A, to a receiving unit 2060, see FIG. 20B. As such, an exemplary method of repelling the transfer media 2019 from the distal opening of one or more channels 2015 in this instance comprises: applying a voltage potential between the one or more conducting sheets 2024 and the structure 2005, via a power unit 2022. Further, in this case, the transfer media 2019 may contain a positive or negative charge which reacts to an electrostatic or magnetic field or a potential difference created by the power unit 2022, as it passes through the structure 2005, and a sheet 2024. Additionally, the electrostatic properties of the one or more conducting sheets 2024 and the structure 2005 can be tuned to optimize the transfer of the polynucleotide 2017 in the transfer media 2019 through a channel 2015 in the structure. Finally, a nonconductive separator may be positioned between the structure 2005 and a conducting sheet 2024, to tune or optimize the electrostatic or magnetic field or the potential difference formed therein.

In some arrangements, a combination of means for attracting the transfer media to or from the channels employ a fluid or gas transfer mechanisms including but not limited to: to laminar pressure, capillary pressure, slip flow pressure, magnetic force, electrostatic force, peristaltic force, sound waves, vibrational force, centripetal force, centrifugal force, or any combination thereof.

Figure 21:
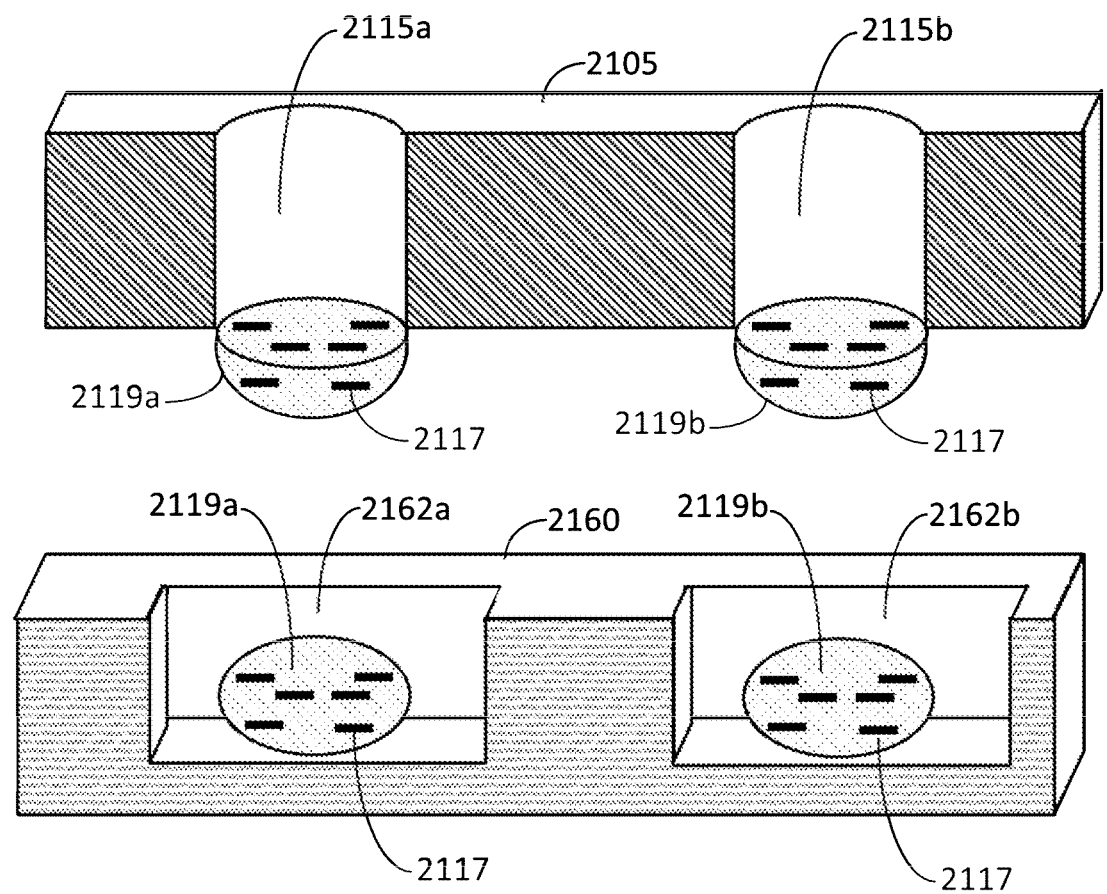
FIG. 21 illustrates a method for electrostatic containment of a polynucleotide from a plurality of channels into a receiving unit.
Figure 22:
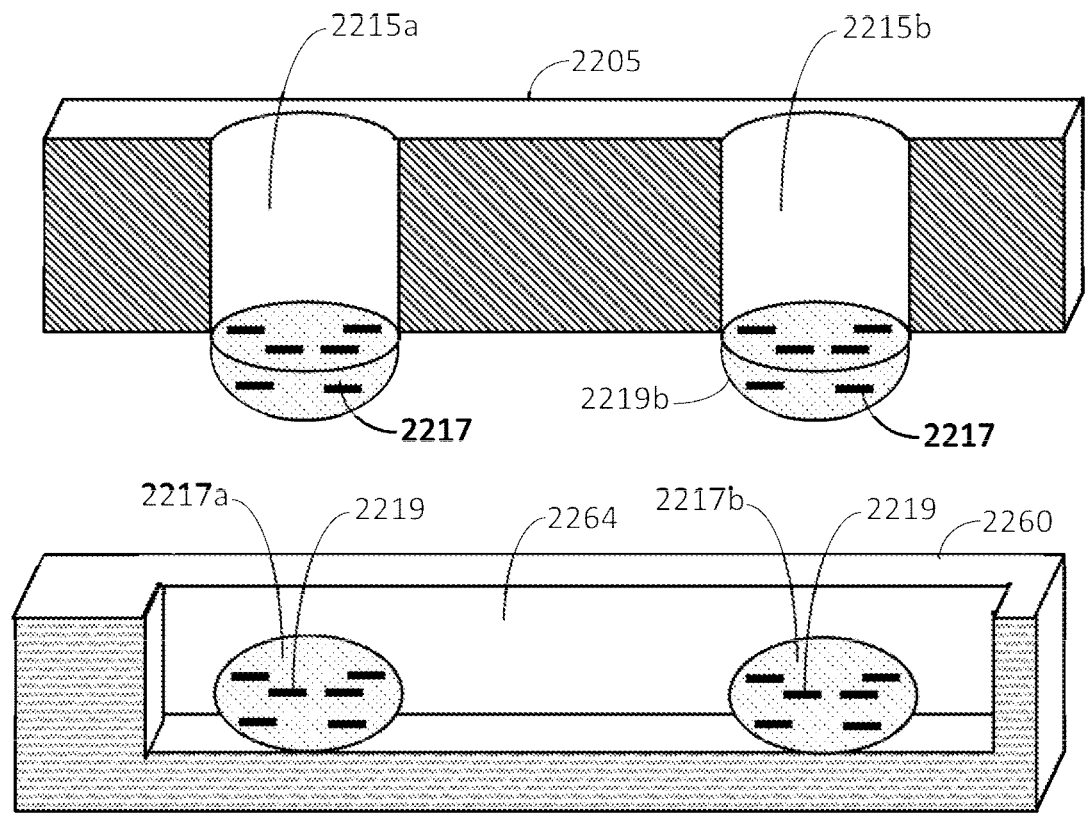
FIG. 22 illustrates a method for electrostatic containment of a polynucleotide from a plurality of channels into a receiving unit.

In some instance, see e.g., FIG. 21 the receiving unit 2160 comprises two or more compartments 2162a 2162b, wherein each compartment 2162a 2162b is capable of receiving and temporarily storing a single respective portion of a gaseous or fluidic transfer media 2119 comprising a polynucleotide 2117. In other arrangements, see e.g., FIG. 22 the receiving unit 2260 comprises a single compartment 2262, capable of receiving and temporarily storing one or more portions of a gaseous or fluidic transfer media 2219, comprising a polynucleotide 2217.

Sequencing

After extraction and/or amplification of polynucleotides from the surface of the structure, suitable sequencing technology may be employed to sequence the polynucleotides. In some cases, the DNA sequence is read on the substrate or within a feature of a structure. In some cases, the polynucleotides stored on the substrate are extracted is optionally assembled into longer nucleic acids and then sequenced.

Polynucleotides synthesized and stored on the structures described herein encode data that can be interpreted by reading the sequence of the synthesized polynucleotides and converting the sequence into binary code readable by a computer. In some cases the sequences require assembly, and the assembly step may need to be at the nucleic acid sequence stage or at the digital sequence stage.

Provided herein are detection systems comprising a device capable of sequencing stored polynucleotides, either directly on the structure and/or after removal from the main structure. In cases where the structure is a reel-to-reel tape of flexible material, the detection system comprises a device for holding and advancing the structure through a detection location and a detector disposed proximate the detection location for detecting a signal originated from a section of the tape when the section is at the detection location. In some instances, the signal is indicative of a presence of a polynucleotide. In some embodiments, the signal is indicative of a sequence of a polynucleotide (e.g., a fluorescent signal). In some instances, information encoded within polynucleotides on a continuous tape is read by a computer as the tape is conveyed continuously through a detector operably connected to the computer. In some instances, a detection system comprises a computer system comprising a polynucleotide sequencing device, a database for storage and retrieval of data relating to polynucleotide sequence, software for converting DNA code of a polynucleotide sequence to binary code, a computer for reading the binary code, or any combination thereof. Computer Systems In various aspects, any of the systems described herein are operably linked to a computer and are optionally automated through a computer either locally or remotely. In various embodiments, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. In some instances, the computer systems are programmed to interface between the user specified base sequence and the position of a material deposition device to deliver the correct reagents to specified regions of the substrate.

Figure 23:
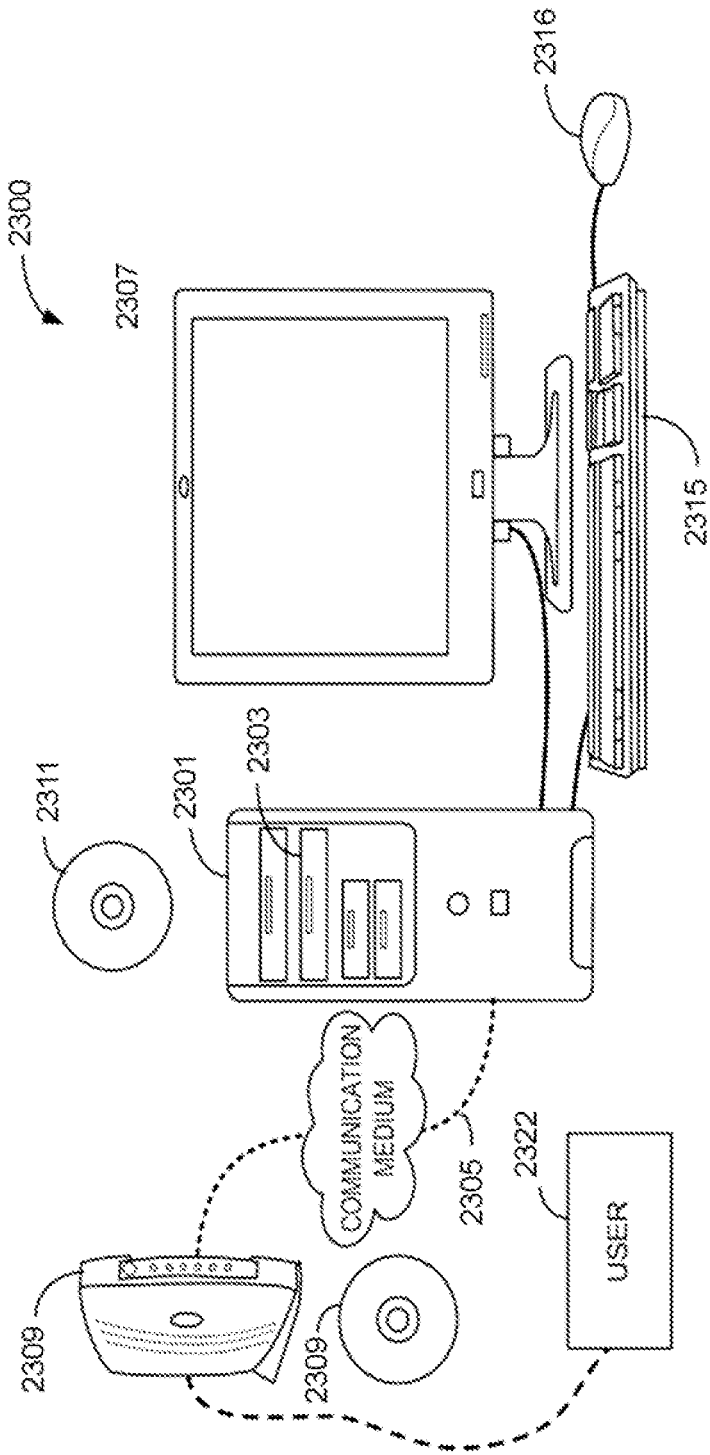
FIG. 23 illustrates an example of a computer system.

The computer system 2300 illustrated in FIG. 23 may be understood as a logical apparatus that can read instructions from media 2311 and/or a network port 2305, which can optionally be connected to server 2309 having fixed medial 412. The system, such as shown in FIG. 4 can include a CPU 2301, disk drives 2303, optional input devices such as keyboard 2315 and/or mouse 2316 and optional monitor 2307. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 2322.

Figure 24:
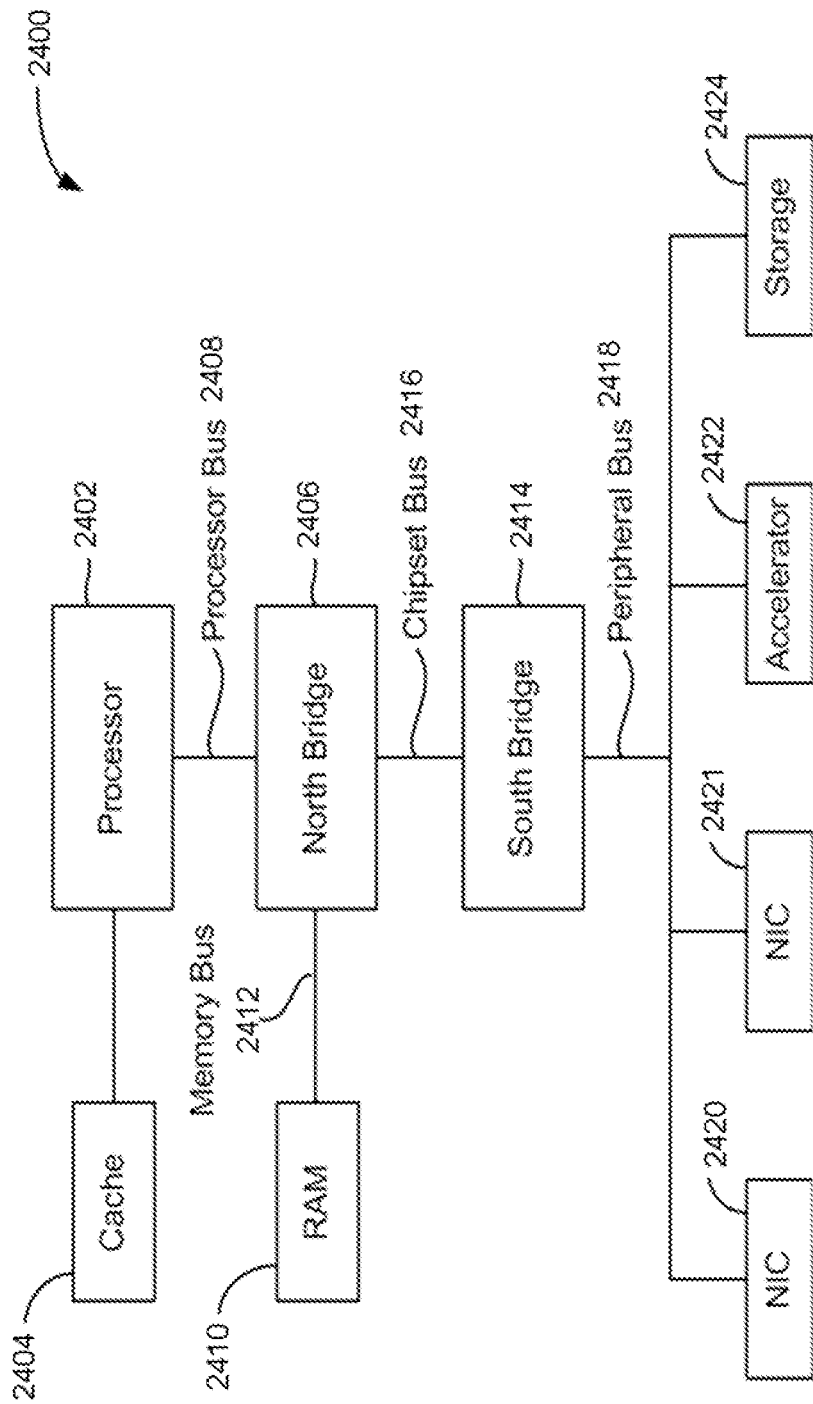
FIG. 24 is a block diagram illustrating architecture of a computer system.

FIG. 24 is a block diagram illustrating a first example architecture of a computer system 1500 that can be used in connection with example embodiments of the present invention. As depicted in FIG. 5, the example computer system can include a processor 2402 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 24, a high speed cache 2404 can be connected to, or incorporated in, the processor 2402 to provide a high speed memory for instructions or data that have been recently, or are frequently, used by processor 2402. The processor 502 is connected to a north bridge 2406 by a processor bus 2408. The north bridge 506 is connected to random access memory (RAM) 2410 by a memory bus 2412 and manages access to the RAM 2410 by the processor 2402. The north bridge 2406 is also connected to a south bridge 2414 by a chipset bus 2416. The south bridge 2414 is, in turn, connected to a peripheral bus 2418. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 2418. In some alternative architectures, the functionality of the north bridge can be incorporated into the processor instead of using a separate north bridge chip.

In some embodiments, system 2400 can include an accelerator card 2422 attached to the peripheral bus 2418. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 2424 and can be loaded into RAM 2410 and/or cache 2404 for use by the processor. The system 2400 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 2400 also includes network interface cards (NICs) 2420 and 521 connected to the peripheral bus for providing network interfaces to external storage, such as Network Attached Storage (NAS) and other computer systems that can be used for distributed parallel processing.

Figure 25:
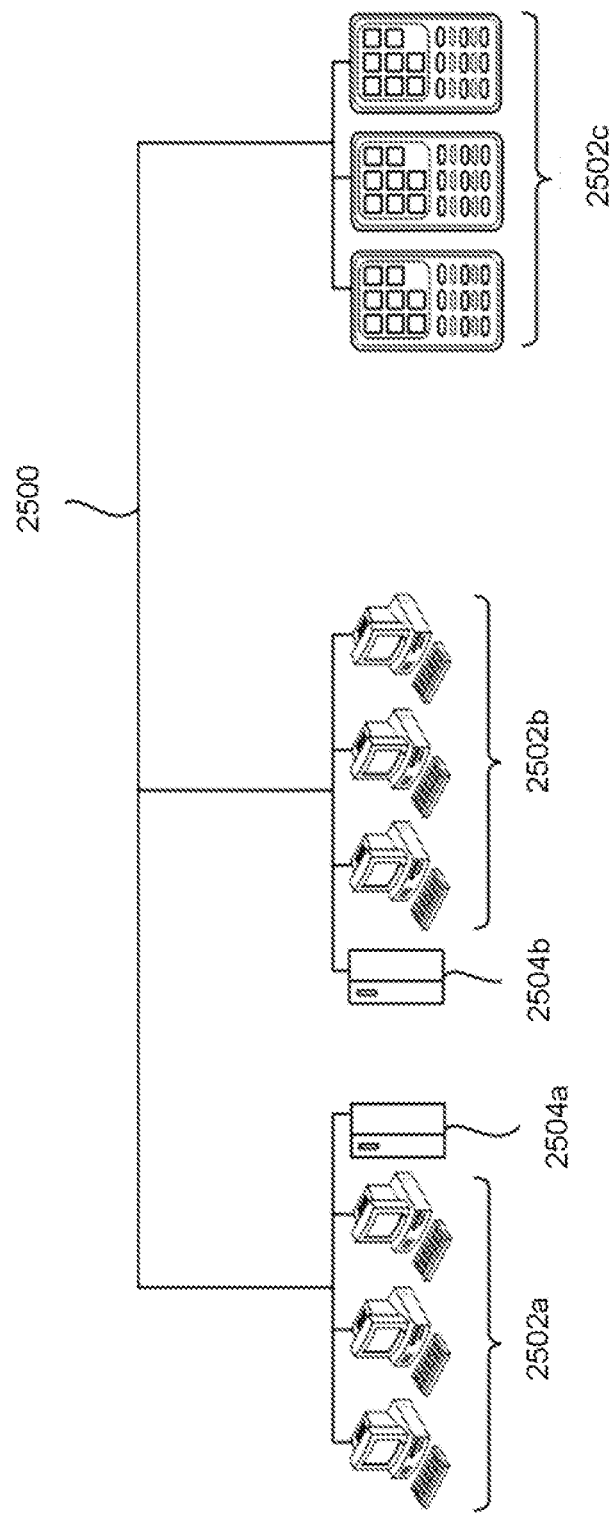
FIG. 25 is a diagram demonstrating a network configured to incorporate a plurality of computer systems, a plurality of cell phones and personal data assistants, and Network Attached Storage (NAS).

FIG. 25 is a diagram showing a network 2500 with a plurality of computer systems 602a, and 602b, a plurality of cell phones and personal data assistants 2002c, and Network Attached Storage (NAS) 2504a, and 2504b. In example embodiments, systems 2502a, 2502b, and 2502c can manage data storage and optimize data access for data stored in Network Attached Storage (NAS) 2504a and 2504b. A mathematical model can be used for the data and be evaluated using distributed parallel processing across computer systems 2502a, and 2502b, and cell phone and personal data assistant systems 2502c. Computer systems 2502a, and 2502b, and cell phone and personal data assistant systems 2502c can also provide parallel processing for adaptive data restructuring of the data stored in Network Attached Storage (NAS) 2504a and 2504b. FIG. 25 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 26:
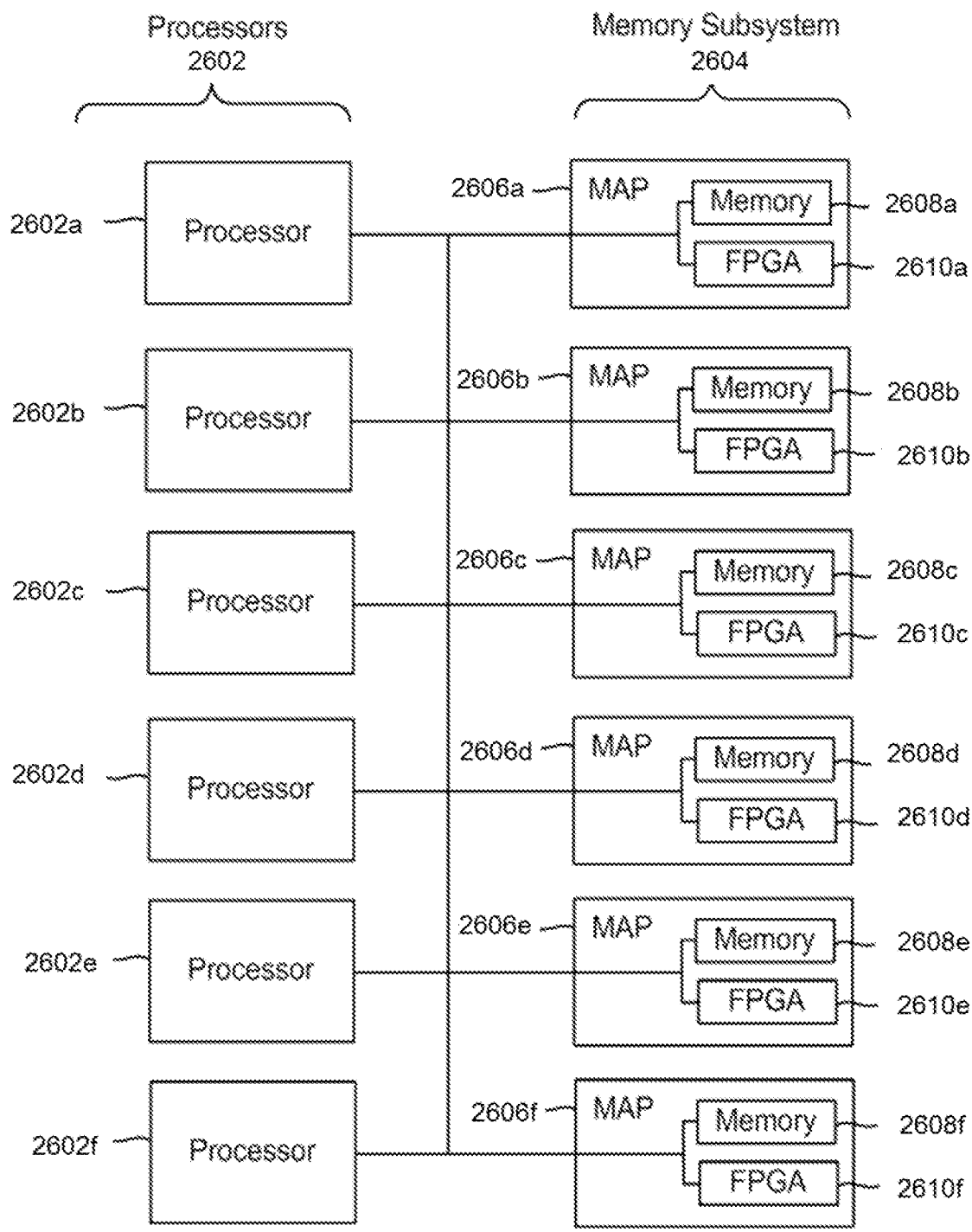
FIG. 26 is a block diagram of a multiprocessor computer system using a shared virtual address memory space.

FIG. 26 is a block diagram of a multiprocessor computer system 2600 using a shared virtual address memory space in accordance with an example embodiment. The system includes a plurality of processors 2602a-f that can access a shared memory subsystem 2604. The system incorporates a plurality of programmable hardware memory algorithm processors (MAPs) 2606*a-f* in the memory subsystem 2604. Each MAP 2606*a-f* can comprise a memory 2608*a-f* and one or more field programmable gate arrays (FPGAs) 2610*a-f*. The MAP provides a configurable functional unit and particular algorithms or portions of algorithms can be provided to the FPGAs 2610*a-f* for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 2608*a-f*, allowing it to execute tasks independently of, and asynchronously from, the respective microprocessor 2602*a-f* In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 7, system on chips (SOCs), application specific integrated circuits (ASICs), or other processing and logic elements. For example, the Set Processor and Optimizer can be implemented with hardware acceleration through the use of a hardware accelerator card, such as the accelerator card 1822 illustrated in FIG. 18.

Provided herein are methods for storing information, comprising: converting an item of information in the form of at least one digital sequence to at least one nucleic acid sequence; providing a flexible structure having a surface; synthesizing a plurality of polynucleotides having predetermined sequences collectively encoding for the at least one nucleic acid sequence, wherein the plurality of polynucleotides comprises at least about 100,000 polynucleotides, and wherein the plurality of polynucleotides extends from the surface of the flexible structure; and storing the plurality of polynucleotides. Further provided herein are methods wherein synthesizing comprises: depositing nucleosides on the surface at predetermined locations; and moving least a portion of the flexible structure through a bath or emissions from a spray bar. Further provided herein are methods wherein the bath or emissions from a spray bar expose the surface of the structure to an oxidizing reagent or a deblocking reagent. Further provided herein are methods wherein synthesizing further comprises capping the nucleosides deposited on the surface. Further provided herein are methods wherein the nucleosides comprise a nucleoside phosphoramidite. Further provided herein are methods wherein the flexible structure comprises a reel-to-reel tape or a continuous tape. Further provided herein are methods wherein the flexible structure comprises a thermoplastic material. Further provided herein are methods wherein the thermoplastic material comprises a polyaryletherketone. Further provided herein are methods wherein the polyaryletherketone is polyetherketone, polyetherketoneketone, poly(ether ether ketone ketone), polyether ether ketone or polyetherketoneetherketoneketone. Further provided herein are methods wherein the flexible structure comprises nylon, nitrocellulose, polypropylene, polycarbonate, polyethylene, polyurethane, polystyrene, acetal, acrylic, acrylonitrile, butadiene styrene, polyethylene terephthalate, polymethyl methacrylate, polyvinyl chloride, transparent PVC foil, Poly (methyl methacrylate), styrenic polymer, fluorine-containing polymers, polyethersulfone or polyimide. Further provided herein are methods wherein each polynucleotide of the plurality of polynucleotides comprises from 50 to 500 bases in length. Further provided herein are methods wherein the plurality of polynucleotides comprises at least about 10 billion polynucleotides. Further provided herein are methods wherein at least about $1.75 \times 10^{13}$ nucleobases are synthesized within 24 hours. Further provided herein are methods wherein at least about $262.5 \times 10^9$ polynucleotides are synthesized within 72 hours. Further provided herein are methods wherein the item of information is text information, audio information or visual information. Further provided herein are methods wherein the nucleosides comprise nucleoside phosphoramidite.

Provided herein are methods for storing information, comprising: converting an item of information in the form of at least one digital sequence to at least one nucleic acid sequence; providing a structure having a surface; synthesizing a plurality of polynucleotides having predetermined sequences collectively encoding for the at least one nucleic acid sequence, wherein the plurality of polynucleotides comprises at least about 100,000 polynucleotides, wherein the plurality of polynucleotides extends from the surface of the structure, and wherein synthesizing comprises: cleaning a surface of the structure; depositing nucleosides on the surface at predetermined locations; oxidizing, deblocking, and optionally capping the nucleosides deposited on the surface; wherein the cleaning, oxidizing, deblocking, and capping comprises moving at least a portion of the flexible structure through a bath or emissions from a spray bar; and storing the plurality of polynucleotides. Further provided herein are methods wherein the nucleosides comprise nucleoside phosphoramidite.

Provided herein are methods for storing information, comprising: converting an item of information in the form of at least one digital sequence to at least one nucleic acid sequence; synthesizing a plurality of polynucleotides having predetermined sequences collectively encoding for the at least one nucleic acid sequence, wherein the plurality of polynucleotides comprises at least about 10,000 polynucleotides, wherein the plurality of polynucleotides collectively encode for a sequence that differs from the predetermined sequences by no more than 1 base in 1000, and wherein each polynucleotide of the plurality of polynucleotides comprises from 50 to 500 bases in length; and storing the at least about 10,000 polynucleotides. Further provided herein are methods wherein the plurality of polynucleotides comprises at least about 100,000 polynucleotides. Further provided herein are methods wherein the plurality of polynucleotides comprises at least about 1,000,000 polynucleotides. Further provided herein are methods wherein the plurality of polynucleotides comprises at least about 10 billion polynucleotides. Further provided herein are methods wherein greater than 90% of the polynucleotides encode for a sequence that does not differ from the predetermined sequence. Further provided herein are methods wherein the item of information is text information, audio information or visual information. Further provided herein are methods wherein the structure is rigid or flexible, and wherein the structure comprises a surface, and wherein the plurality of polynucleotides extend from the surface. Further provided herein are methods wherein the nucleosides comprise nucleoside phosphoramidite.

Provided herein are methods for storing information, comprising: converting an item of information in the form of at least one digital sequence to at least one nucleic acid sequence; synthesizing a plurality of polynucleotides having predetermined sequences collectively encoding for the at least one nucleic acid sequence, wherein the plurality of polynucleotides comprises at least about 10,000 polynucleotides, wherein each polynucleotide of the plurality of polynucleotides comprises from 50 to 500 bases in length, and where the plurality of polynucleotides extends from the surface of a flexible structure; and storing the plurality of polynucleotides. Further provided herein are methods wherein the flexible structure comprises a reel-to-reel tape or a continuous tape. Further provided herein are methods wherein each polynucleotide extends from a locus on the surface of the flexible structure, wherein the locus is about 1 um to about 500 um in diameter. Further provided herein are methods wherein the locus is about 1 um to about 50 um in diameter. Further provided herein are methods wherein the locus is about 10 um in diameter. Further provided herein are methods wherein the flexible structure comprises a thermoplastic material. Further provided herein are methods wherein the thermoplastic material comprises a polyaryletherketone. Further provided herein are methods wherein the polyaryletherketone is polyetherketone, polyetherketoneketone, poly(ether ether ketone ketone), polyether ether ketone or polyetherketoneetherketoneketone. Further provided herein are methods wherein the flexible structure comprises nylon, nitrocellulose, polypropylene, polycarbonate, polyethylene, polyurethane, polystyrene, acetal, acrylic, acrylonitrile, butadiene styrene, polyethylene terephthalate, polymethyl methacrylate, polyvinyl chloride, transparent PVC foil, Poly(methyl methacrylate), styrenic polymer, fluorine-containing polymers, polyethersulfone or polyimide. Further provided herein are methods wherein the flexible structure has a thickness of less than about 10 mm. Further provided herein are methods wherein each polynucleotide is about 200 bases in length. Further provided herein are methods wherein at least about $1.75 \times 10^{13}$ nucleobases are synthesized within 24 hours. Further provided herein are methods wherein at least about $262.5 \times 10^9$ polynucleotides are synthesized within 72 hours. Further provided herein are methods wherein the nucleosides comprise nucleoside phosphoramidite.

Provided herein are methods for storing information, the method comprising: encrypting at least one item of information in the form of at least one digital sequence to at least one nucleic acid sequence; synthesizing a plurality of polynucleotides having predetermined sequences collectively encoding for the at least one nucleic acid sequence, wherein the plurality of polynucleotides comprises at least about 10,000 polynucleotides, and wherein each polynucleotide of the plurality of polynucleotides comprises from 50 to 500 bases in length; storing the plurality of polynucleotides; sequencing the plurality of polynucleotides; decrypting the plurality of polynucleotides from a nucleic acid sequence to a digital sequence; and assembling the digital sequence to form the at least one digital sequence, wherein the at least one digital sequence is assembled with 100% accuracy compared to the initial at least one digital sequence. Further provided herein are methods further comprising releasing the plurality of polynucleotides. Further provided herein are methods wherein the nucleosides comprise nucleoside phosphoramidite.

Provided herein are devices for information storage, comprising: a flexible structure having a surface; and a plurality of loci on the surface, wherein each locus has a width of from about 1 to about 500 um, and wherein each locus of the plurality of loci is coated with a moiety that binds to the surface and comprises a hydroxyl group available for nucleoside coupling. Further provided herein are devices wherein the flexible structure rests in a curved position. Further provided herein are devices wherein the curved position comprises a curve that is greater than 30 degrees. Further provided herein are devices wherein the curved position comprises a curve that is greater than 180 degrees. Further provided herein are devices wherein the flexible structure comprises at least about 1 million loci. Further provided herein are devices wherein the flexible structure has a total surface area of less than about 4.5 m². Further provided herein are devices wherein the flexible structure comprises more than 2 billion loci per m². Further provided herein are devices wherein the flexible structure comprises a thermoplastic material. Further provided herein are devices wherein the thermoplastic material comprises a polyaryletherketone. Further provided herein are devices wherein the polyaryletherketone is polyetherketone, polyetherketoneketone, poly(ether ether ketone ketone), polyether ether ketone or polyetherketoneetherketoneketone. Further provided herein are devices wherein the flexible structure comprises nylon, nitrocellulose, polypropylene, polycarbonate, polyethylene, polyurethane, polystyrene, acetal, acrylic, acrylonitrile, butadiene styrene, polyethylene terephthalate, polymethyl methacrylate, polyvinyl chloride, transparent PVC foil, Poly(methyl methacrylate), styrenic polymer, fluorine-containing polymers, polyethersulfone or polyimide. Further provided herein are devices wherein the flexible structure has a thickness of less than about 10 mm. Further provided herein are devices wherein each locus is from about 1 um to about 50 um in width. Further provided herein are devices wherein each locus has a diameter of about 10 um. Further provided herein are devices wherein the center of a first locus is about 21 um from the center of a second locus and the first locus and the second locus. Further provided herein are devices wherein the flexible structure comprises a reel-to-reel tape or a continuous tape. Further provided herein are devices wherein each locus comprises a channel.

Provided herein are polynucleotide libraries for information storage, comprising a plurality of polynucleotides, wherein the plurality of polynucleotides comprises at least about 10,000 polynucleotides, wherein the plurality of polynucleotides collectively encodes for a sequence that differs from an aggregate of predetermined sequences by no more than 1 base in 1000, and wherein each polynucleotide of the plurality of polynucleotides comprises: a predetermined sequence that, when decrypted, encodes for digital information. Further provided herein are libraries wherein the plurality of polynucleotides comprises at least about 100,000 polynucleotides. Further provided herein are libraries wherein the plurality of polynucleotides comprises at least about 10 billion polynucleotides. Further provided herein are libraries wherein each polynucleotide of the plurality of polynucleotides is attached to a surface of a structure by a tether. Further provided herein are libraries wherein the tether comprises a cleavable region having at least one nucleotide chemically modified to detach from the polynucleotide in the presence of a cleaving reagent. Further provided herein are libraries wherein the tether comprises from about 10 to about 50 bases. Further provided herein are libraries wherein greater than 90% of the polynucleotides encode for a sequence that does not differ from the predetermined sequences. Further provided herein are libraries wherein the digital information encodes for text, audio or visual information. Further provided herein are libraries wherein the library is synthesized in less than 3 days. Further provided herein are libraries wherein the library is synthesized in less than 24 hours.

Further provided herein are methods for synthesizing polynucleotides that encode a range of an amount of digital information. In some instances, an amount of digital information is at least 1 gigabyte (GB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 gigabytes. In some instances, the amount of digital information is at least 1 terabyte (TB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 terabytes. In some instances, the amount of digital information is at least 1 petabyte (PB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 petabytes.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Functionalization of a Device Surface

A device was functionalized to support the attachment and synthesis of a library of polynucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200× spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for polynucleotide synthesis.

Example 2: Synthesis of a 50-mer Sequence Oligonucleotides

A two dimensional oligonucleotide synthesis device was assembled into a flowcell, which was connected to a flowcell (Applied Biosystems (ABI394 DNA Synthesizer"). The two-dimensional oligonucleotide synthesis device was uniformly functionalized with N-(3-TRIETHOXYSILYLPROPYL)-4-HYDROXYBUTYRAMIDE (Gelest) was used to synthesize an exemplary oligonucleotide of 50 bp ("50-mer oligonucleotide") using oligonucleotide synthesis methods described herein.

The sequence of the 50-mer was as described in SEQ ID NO.: 1. 5'AGACAATCAACCAT-TTGGGGTGGACAGCCTTGACCTCTAGACTTCGG-CAT##TTTTT TTTTT3' (SEQ ID NO.: 1), where # denotes Thymidine-succinyl hexamide CED phosphoramidite (CLP-2244 from ChemGenes), which is a cleavable linker enabling the release of polynucleotides from the surface during deprotection.

The synthesis was done using standard DNA synthesis chemistry (coupling, capping, oxidation, and deblocking) according to the protocol in Table 3 and an ABI synthesizer.

TABLE 3

| General DNA Synthesis Process Name | Process Step | Time (sec) |
|---|---|---|
| WASH (Acetonitrile Wash Flow) | Acetonitrile System Flush | 4 |
| | Acetonitrile to Flowcell | 23 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 6 |
| | Activator + Phosphoramidite to Flowcell | 6 |
| | Activator to Flowcell | 0.5 |
| | Activator + Phosphoramidite to Flowcell | 5 |
| | Activator to Flowcell | 0.5 |
| | Activator + Phosphoramidite to Flowcell | 5 |

TABLE 3-continued

| General DNA Synthesis Process Name | Process Step | Time (sec) |
|---|---|---|
| | Activator to Flowcell | 0.5 |
| | Activator + Phosphoramidite to Flowcell | 5 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| DNA BASE ADDITION (Phosphoramidite + Activator Flow) | Activator Manifold Flush | 2 |
| | Activator to Flowcell | 5 |
| | Activator + Phosphoramidite to Flowcell | 18 |
| | Incubate for 25 sec | 25 |
| WASH (Acetonitrile Wash Flow) | Acetonitrile System Flush | 4 |
| | Acetonitrile to Flowcell | 15 |
| | N2 System Flush | 4 |
| | Acetonitrile System Flush | 4 |
| CAPPING (CapA + B, 1:1, Flow) | CapA + B to Flowcell | 15 |
| WASH (Acetonitrile Wash Flow) | Acetonitrile System Flush | 4 |
| | Acetonitrile to Flowcell | 15 |
| | Acetonitrile System Flush | 4 |
| OXIDATION (Oxidizer Flow) | Oxidizer to Flowcell | 18 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 15 |
| | Acetonitrile to Flowcell | 15 |
| | N2 System Flush | 4 |
| | Acetonitrile System Flush | 4 |
| | Acetonitrile to Flowcell | 23 |
| | N2 System Flush | 4 |
| | Acetonitrile System Flush | 4 |
| DEBLOCKING (Deblock Flow) | Deblock to Flowcell | 36 |
| WASH (Acetonitrile Wash Flow) | Acetonitrile System Flush | 4 |
| | N2 System Flush | 4 |
| | Acetonitrile System Flush | 4 |
| | Acetonitrile to Flowcell | 18 |
| | N2 System Flush | 4.13 |
| | Acetonitrile System Flush | 4.13 |
| | Acetonitrile to Flowcell | 15 |

The phosphoramidite/activator combination was delivered similar to the delivery of bulk reagents through the flowcell. No drying steps were performed as the environment stays "wet" with reagent the entire time.

The flow restrictor was removed from the ABI 394 synthesizer to enable faster flow. Without flow restrictor, flow rates for amidites (0.1M in ACN), Activator, (0.25M Benzoylthiotetrazole ("BTT"; 30-3070-xx from GlenResearch) in ACN, and Ox (0.02M 12 in 20% pyridine, 10% water, and 70% THF) were roughly ~100 uL/sec, for acetonitrile ("ACN") and capping reagents (1:1 mix of CapA and CapB, wherein CapA is acetic anhydride in THF/Pyridine and CapB is 16% 1-methylimidizole in THF), roughly ~200 uL/sec, and for Deblock (3% dichloroacetic acid in toluene), roughly ~300 uL/sec (compared to ~50 uL/sec for all reagents with flow restrictor). The time to completely push out Oxidizer was observed, the timing for chemical flow times was adjusted accordingly and an extra ACN wash was introduced between different chemicals. After oligonucleotide synthesis, the chip was deprotected in gaseous ammonia overnight at 75 psi. Five drops of water were applied to the surface to assemble polynucleotides. The assembled polynucleotides were then analyzed on a Bio-Analyzer small RNA chip (data not shown).

Example 3: Synthesis of a 100-mer Sequence Oligonucleotides

The same process as described in Example 2 for the synthesis of the 50-mer sequence was used for the synthesis of a 100-mer oligonucleotide ("100-mer oligonucleotide"; 5' CGGGATCCTTATCGTCATCGTCGTACA-GATCCCGACCCATTTGCTGTCCACCAGTCAT GCTAGCCATACCATGATGATGATGATGAT-GAGAACCCCGCAT ##TTTTTTTTTT3', where # denotes Thymidine-succinyl hexamide CED phosphoramidite (CLP-2244 from ChemGenes); SEQ ID NO.: 2) on two different silicon chips, the first one uniformly functionalized with N-(3-TRIETHOXYSILYLPROPYL)-4-HYDROXYBU-TYRAMIDE and the second one functionalized with 5/95 mix of 11-acetoxyundecyltriethoxysilane and n-decyltri-ethoxysilane, and the polynucleotides extracted from the surface were analyzed on a BioAnalyzer instrument (data not shown).

All ten samples from the two chips were further PCR amplified using a forward (5'ATGCGGGGTTCTCAT-CATC3; SEQ ID NO.: 3) and a reverse (5'CGGGATCCT-TATCGTCATCG3'; SEQ ID NO.: 4) primer in a 50 uL PCR mix (25 uL NEB Q5 mastermix, 2.5 uL 10 uM Forward primer, 2.5 uL 10 uM Reverse primer, 1 uL polynucleotide extracted from the surface, and water up to 50 uL) using the following thermalcycling program:

98 C, 30 sec

98 C, 10 sec; 63 C, 10 sec; 72 C, 10 sec; repeat 12 cycles

72 C, 2 min

The PCR products were also run on a BioAnalyzer (data not shown), demonstrating sharp peaks at the 100-mer position. Next, the PCR amplified samples were cloned, and Sanger sequenced. Table 4 summarizes the results from the Sanger sequencing for samples taken from spots 1-5 from chip 1 and for samples taken from spots 6-10 from chip 2.

TABLE 4

| Spot | Error rate | Cycle efficiency |
|---|---|---|
| 1 | 1/763 bp | 99.87% |
| 2 | 1/824 bp | 99.88% |
| 3 | 1/780 bp | 99.87% |
| 4 | 1/429 bp | 99.77% |
| 5 | 1/1525 bp | 99.93% |
| 6 | 1/1615 bp | 99.94% |
| 7 | 1/531 bp | 99.81% |
| 8 | 1/1769 bp | 99.94% |
| 9 | 1/854 bp | 99.88% |
| 10 | 1/1451 bp | 99.93% |

Thus, the high quality and uniformity of the synthesized oligonucleotides were repeated on two chips with different surface chemistries. Overall, 89%, corresponding to 233 out of 262 of the 100-mers that were sequenced were perfect sequences with no errors.

Table 5 summarizes error characteristics for the sequences obtained from the oligonucleotides samples from spots 1-10.

TABLE 5

| Sample | OSA_0 | OSA_0 | OSA_0 | OSA_0 | OSA_0 | OSA_0 | OSA_0 | OSA_0 | OSA_0 | OSA_00 |
|---|---|---|---|---|---|---|---|---|---|---|
| ID/Spot no. | 046/1 | 047/2 | 048/3 | 049/4 | 050/5 | 051/6 | 052/7 | 053/8 | 054/9 | 55/10 |
| Total Sequences | 32 | 32 | 32 | 32 | 32 | 32 | 32 | 32 | 32 | 32 |
| Sequencing Quality | 25 of 28 | 27 of 27 | 26 of 30 | 21 of 23 | 25 of 26 | 29 of 30 | 27 of 31 | 29 of 31 | 28 of 29 | 25 of 28 |
| Oligo Quality | 23 of 25 | 25 of 27 | 22 of 26 | 18 of 21 | 24 of 25 | 25 of 29 | 22 of 27 | 28 of 29 | 26 of 28 | 20 of 25 |
| ROI Match Count | 2500 | 2698 | 2561 | 2122 | 2499 | 2666 | 2625 | 2899 | 2798 | 2348 |
| ROI Mutation | 2 | 2 | 1 | 3 | 1 | 0 | 2 | 1 | 2 | 1 |
| ROI Multi Base Deletion | 0 | 0 | 0 | 0 | 0 | 0 | 0 | 0 | 0 | 0 |
| ROI Small Insertion | 1 | 0 | 0 | 0 | 0 | 0 | 0 | 0 | 0 | 0 |
| ROI Single Base Deletion | 0 | 0 | 0 | 0 | 0 | 0 | 0 | 0 | 0 | 0 |
| Large Deletion Count | 0 | 0 | 1 | 0 | 0 | 1 | 1 | 0 | 0 | 0 |
| Mutation: G > A | 2 | 2 | 1 | 2 | 1 | 0 | 2 | 1 | 2 | 1 |
| Mutation: T > C | 0 | 0 | 0 | 1 | 0 | 0 | 0 | 0 | 0 | 0 |
| ROI Error Count | 3 | 2 | 2 | 3 | 1 | 1 | 3 | 1 | 2 | 1 |
| ROI Error Rate | Err: ~1 in 834 MP | Err: ~1 in 1350 MP | Err: ~1 in 1282 MP | Err: ~1 in 708 MP | Err: ~1 in 2500 MP | Err: ~1 in 2667 MP | Err: ~1 in 876 MP | Err: ~1 in 2900 MP | Err: ~1 in 1400 MP | Err: ~1 in 2349 MP |
| ROI Minus Primer Error Rate | Err: ~1 in 763 | Err: ~1 in 824 | Err: ~1 in 780 | Err: ~1 in 429 | Err: ~1 in 1525 | Err: ~1 in 1615 | Err: ~1 in 531 | Err: ~1 in 1769 | Err: ~1 in 854 | Err: ~1 in 1451 |

Example 4: Highly Accurate DNA-Based Information Storage and Assembly

Digital information was selected in the form of binary data totaling about 0.2 GB included content for the Universal Declaration of Human Rights in more than 100 languages, the top 100 books of Project Guttenberg and a seed database. The digital information was encrypted into a nucleic acid-based sequence and divided into strings. Over 10 million non-identical polynucleotides, each corresponding to a string, were synthesized on a rigid silicon surface in a manner similar to that described in Example 2. Each non-identical polynucleotide was under equal or less than 200 bases in length. The synthesized polynucleotides were collected and sequenced and decoded back to digital code, with 100% accuracy for the source digital information, compared to the initial at least one digital sequence.

Example 5: Conversion of Digital Information to Nucleic Acid Sequence

A computer txt file includes text information. A general purpose computer uses a software program having machine instructions for conversion of the sequence to base 3, 4, or 5 sequence, depending on instructions received. Each number in base 3 is assigned a nucleic acid (e.g., A=0, T=1, C=2). Each number in base 4 is assigned a nucleic acid (e.g., A=0, T=1, C=2, G=3). Alternatively, a base 5 quinary sequence is used, where each number in base 5 is assigned a nucleic acid (e.g., A=0, T=1, C=2, G=3, U=4). A sequence is generated as depicted in Table 6. Machine instructions are then provided for de novo synthesis of polynucleotides encoding the nucleic acid sequence.

TABLE 6

| Text | Jack went up the hill. |
|---|---|
| Binary sequence | 0100101001100001011000110110101100100000011101110110010101101110001110100000100000011101010111000000100000011101000110100001100101010010000011010000101000100000110100100000110100001100101 |
| Ternary sequence | 10101020110002210100211020122212001011122022100021220022102000111221210201120102111212220010111000100200102200222221100222221112 |
| Quaternary sequence | 10221201120312230200131312111232131002001311130002001310122012110200122012211230123002320031002200310022 |
| Quinary sequence | 33221433013301230301312300103024443334330043122410302032021020112342341100431241100334213 |

Example 6: Flexible Surface Having a High Density of Loci

Figure 11A:
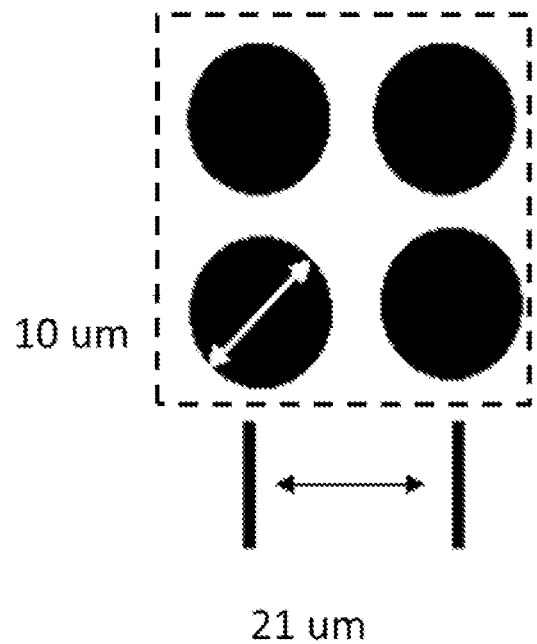
FIG. 11A illustrates a zoom in of loci on a structure described herein.
Figure 11B:
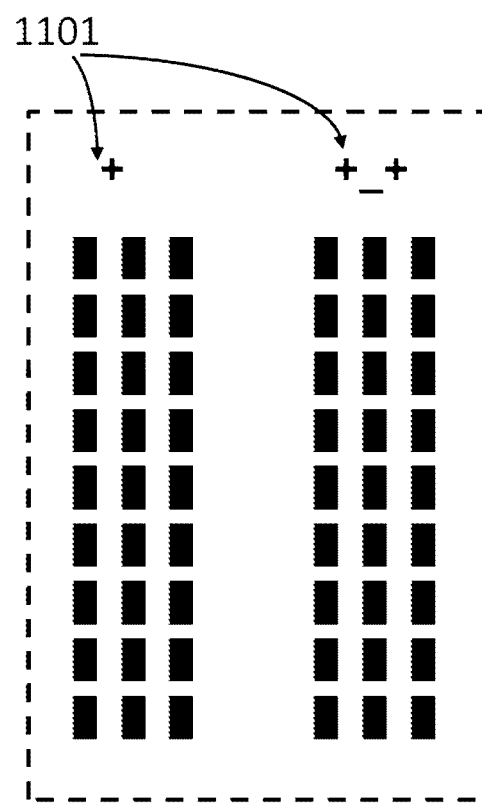
FIGS. 11B-11C illustrate markings on structures described herein.
Figure 11C:
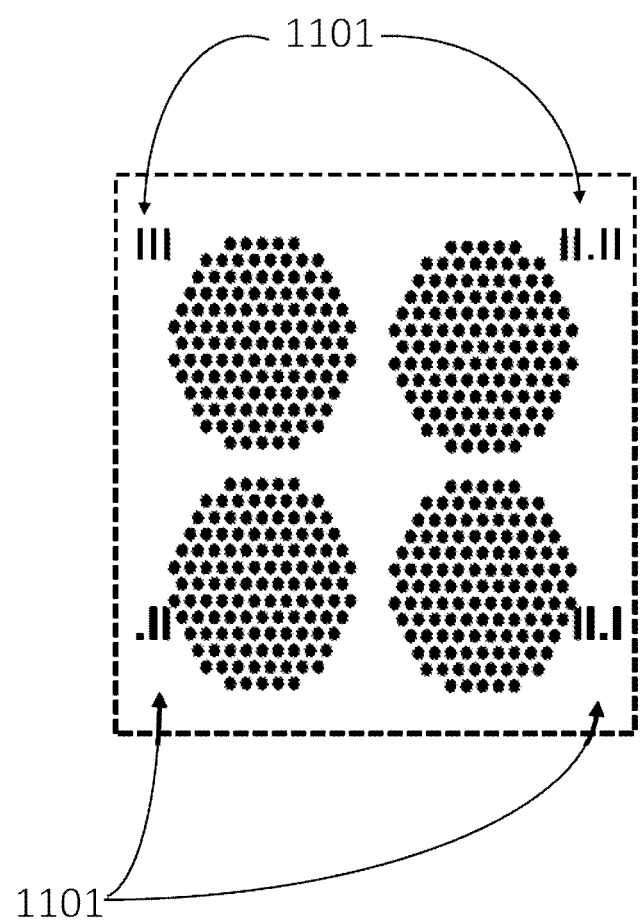

A flexible structure comprising thermoplastic material is coated with a nucleoside coupling reagent. The coating agent is patterned for a high density of loci. A portion of the flexible surface is illustrated in FIG. 11A. Each locus has a diameter of 10 um, with a center-to-center distance between two adjacent loci of 21 um. The locus size is sufficient to accommodate a sessile drop volume of 0.2 pl during a polynucleotide synthesis deposition step. The small locus dimensions allow for a high density of polynucleotides to be synthesized on the surface of the substrate. The locus density is 2.2 billion loci/m$^2$ (1 locus/441×10$^{-12}$ m$^2$). A 4.5 m$^2$ substrate is manufactured having 10 billion loci, each with a 10 um diameter. The flexible structure is optionally placed in a continuous loop system, FIG. 9A, or a reel-to-reel system, FIG. 9B, for polynucleotide synthesis.

Example 7: Polynucleotide Synthesis on a Flexible Structure

A flexible structure is prepared comprising a plurality of loci on a thermoplastic flexible material. The structure serves as a support for the synthesis of polynucleotides using a polynucleotide synthesis device comprising a deposition device. The flexible structure is in the form of a flexible media much like a magnetic reel-to-reel tape.

De novo synthesis operates in a continuous production line manner with the structure travelling through a solvent bath and then beneath a stack of printheads where the phosphoramidites are printed on to a surface of the structure. The flexible structure with the sessile drops deposited on to the surface is rolled into a bath of oxidizing agent, then the tape emerges from the oxidizing bath and is immersed in an acetonitrile wash bath then submerged in a deblock bath. Optionally, the tape is traversed through a capping bath. In an alternative workflow, the flexible structure emerges from the oxidizing bath and is sprayed with acetonitrile in a wash step.

Alternatively, a spray bar is used instead of a liquid bath. In this process, the nucleotides are still deposited on the surface with an inkjet device but the flood steps are now done in a chamber with spray nozzles. For example, the deposition device has 2,048 nozzles that each deposit 100,000 droplets per second at 1 nucleobase per droplet. There is a sequential ordering of spray nozzles to mimic the ordering of the flood steps in standard phosphoramidite chemistry. This technique provides for easily changing the chemicals loaded in the spray bar to accommodate different process steps. Polynucleotides are deprotected or cleaved in the same manner as described in Example 2.

For each deposition device, more than 1.75×10$^{13}$ nucleobases are deposited on the structure per day. A plurality of 200 nucleobase polynucleotides is synthesized. In 3 days, at a rate of 1.75×10$^{13}$ bases per day, 262.5×10$^9$ polynucleotides are synthesized. Each oligonucleotide sequence comprises a polynucleotide of at least 15 bases embedded in a longer polynucleotide. In one instance, the polynucleotide is designed to have at least, in 5' to 3' order: a linker region, cleavage region, a first primer binding region, a bar code region, target sequence regions, and a second primer region.

Example 8: Electrostatic Transfer of Polynucleotides Following De Novo Synthesis Polynucleotides are synthesized similarly to Examples 2-3. Following polynucleotide synthesis, the polynucleotides are transferred from a channel in a structure to one or more channels or a receiving unit using electrostatic force.

An aqueous or gaseous transfer media that adheres to the polynucleotides is deposited. The channel is surrounded by interconnected conductor plates located above the channel. The transfer media comprises a charge (positive or negative) that reacts with an electrostatic field created by the conductor plates. A voltage potential is applied between the interconnected conductor plates, resulting in attraction of the transfer media and transfer of the polynucleotides through an opening of the channel.

In order to repel the polynucleotides from the channel, the channel is surrounded by interconnected conductor plates located below the channel. When voltage potential is applied between the interconnected conductor plates, the transfer media is repelled from the channel to one or more channels or the receiving unit.

Example 9: Transfer of Polynucleotides Following De Novo Synthesis Using Vibrational Force Polynucleotides are synthesized similarly to Examples 2-3. Following polynucleotide synthesis, the polynucleotides are transferred from a channel in a structure to one or more channels or a receiving unit using vibrational force.

An aqueous or gaseous transfer media that adheres to the polynucleotides is deposited. The channel is surrounded by vibrational energy applicators. Vibrational energy is applied through the vibrational energy applicators, resulting in transfer of the polynucleotides through an opening of the channel to one or more channels or the receiving unit.

Example 10: Transfer of Polynucleotides Following De Novo Synthesis Using a Slip Polynucleotides are synthesized similarly to Examples 2-3. Following polynucleotide synthesis, the polynucleotides are transferred from a channel in a structure to one or more channels or a receiving unit using a slip.

An aqueous or gaseous transfer media that adheres to the polynucleotides is deposited. A slip is positioned in contact with the structure at an angle. By rotating the slip relative to the structure, for example at either 10°, 20°, 30°, 40°, 50°, 60°, 70° or 80°, the transfer media is transferred to one or more channels or the receiving unit.

Example 11: Transfer of Polynucleotides Following De Novo Synthesis Using Applied Pressure Polynucleotides are synthesized similarly to Examples 2-3. Following polynucleotide synthesis, the polynucleotides are transferred from a channel in a structure to one or more channels or a receiving unit using applied pressure.

An aqueous or gaseous transfer media that adheres to the polynucleotides is deposited. An applied pressure within a gas or fluid and a pressure release are employed to force the transfer media through a channel in the structure. By creating a pressure differential, opening of a pressure release forces the transfer media through the channel.

Example 12: Transfer of Polynucleotides Following De Novo Synthesis Using Applied Pressure and a Nozzle Polynucleotides are synthesized similarly to Examples 2-3. Following polynucleotide synthesis, the polynucleotides are transferred from a channel in a flexible structure to one or more channels or a receiving unit using applied pressure and a nozzle.

An aqueous or gaseous transfer media that adheres to the polynucleotides is deposited. The flexible structure is moved using a roller such that the channel is aligned below a nozzle.

The nozzle then applies pressure towards a channel and forces the transfer media through the channel.

Example 13: Transfer of Polynucleotides Following De Novo Synthesis Using a Pin Polynucleotides are synthesized similarly to Examples 2-3. Following polynucleotide synthesis, the polynucleotides are transferred from a channel in a structure to one or more channels or a receiving unit using a pin.

An aqueous or gaseous transfer media that adheres to the polynucleotides is deposited. The pin contacts and attracts the transfer media and a relative vertical motion between the pin and the structure dislocates the transfer media from the structure to one or more channels or the receiving unit.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system comprising:
a synthesizer comprising a wafer having a plurality of substrates for synthesizing a plurality of polynucleotides, the synthesizer having one or more fluidic openings;
a reactor, wherein the reactor amplifies the plurality of polynucleotides and transfers fluid comprising the plurality of polynucleotides;
a receiving unit, wherein the receiving unit has a compartment for holding the plurality of polynucleotides; and
a power unit, wherein the power unit directs the transfer of the plurality of polynucleotides through one or more channels of the system.

2. The system of claim 1, further comprising a sequencing device, wherein the sequencing device sequences the plurality of polynucleotides.

3. The system of claim 1, further comprising a computer system.

4. The system of claim 3, wherein the computer system comprises a database for storage and retrieval of data relating to the plurality of polynucleotides.

5. The system of claim 3, wherein the computer system comprises an encryption scheme to convert a binary code to a nucleic acid sequence, and wherein the nucleic acid sequence is adapted for synthesis as the plurality of polynucleotides.

6. The system of claim 3, wherein the computer system comprises a software program for converting sequences of the plurality of polynucleotides to binary code.

7. The system of claim 3, wherein the computer system is configured to execute instructions for automation of the system.

8. The system of claim 7, wherein automation comprises synchronization of one or more functions of the system.

9. The system of claim 8, wherein the one or more functions of the system comprises movement of a material deposition device, dispense action, vacuum actuation, or any combination thereof.

10. The system of claim 9, wherein the material deposition device is configured to release one or more reagents onto a first substrate of the plurality of substrates.

11. The system of claim 10, wherein the material deposition device comprises a plurality of nozzles, wherein a nozzle of the plurality of nozzles is configured to deposit a droplet comprising the one or more reagents onto the first substrate.

12. The system of claim 11, wherein the material deposition device receives instructions from the computer system to deposit the droplet at a specified region of the first substrate.

13. The system of claim 1, wherein the reactor comprises a temperature control element.

14. The system of claim 1, wherein the reactor is further configured to allow for transfer of fluid comprising reagents.

15. The system of claim 1, wherein the plurality of polynucleotides encode for a digital sequence.

16. The system of claim 15, wherein the plurality of polynucleotides comprise a barcode that corresponds to a particular region of the digital sequence.

17. The system of claim 1, wherein the plurality of polynucleotides comprise a sequence-specific primer region.

18. The system of claim 17, wherein the plurality of polynucleotides are retrieved in part based on the sequence-specific primer region.

19. The system of claim 1, wherein the plurality of polynucleotides are transferred in a transfer media, wherein the transfer media comprises an aqueous transfer media or a gaseous transfer media.

20. The system of claim 1, wherein the receiving unit comprises two or more compartments, wherein each of the two or more compartments holds a portion of the plurality of polynucleotides.

* * * * *

UNITED STATES PATENT AND TRADEMARK OFFICE
CERTIFICATE OF CORRECTION

PATENT NO. : 12,056,264 B2  
APPLICATION NO. : 17/938228  
DATED : August 6, 2024  
INVENTOR(S) : Bill James Peck Page 1 of 1

It is certified that error appears in the above-identified patent and that said Letters Patent is hereby corrected as shown below:

In the Claims

In Claim 1, Column 53, Line 7, delete "reactor," and insert -- reaction chamber, --.

In Claim 1, Column 53, Line 7, delete "reactor" and insert -- reaction chamber --.

In Claim 1, Column 53, Line 14, delete "unit," and insert -- distributor, --.

In Claim 1, Column 53, Line 14, delete "unit" and insert -- distributor --.

In Claim 2, Column 53, Lines 17-18, delete "sequencing device," and insert -- sequencer, --.

In Claim 2, Column 53, Line 18, delete "sequencing device" and insert -- sequencer --.

Signed and Sealed this  
First Day of July, 2025

Coke Morgan Stewart  
*Acting Director of the United States Patent and Trademark Office*

```
                          SEQUENCE LISTING

Sequence total quantity: 4
SEQ ID NO: 1             moltype = DNA  length = 62
FEATURE                  Location/Qualifiers
misc_feature             1..62
                         note = Description of Artificial Sequence:
                          Syntheticoligonucleotide
modified_base            51..52
                         mod_base = OTHER
                         note = Thymidine-succinyl hexamide CED phosphoramidite
source                   1..62
                         mol_type = other DNA
                         organism = synthetic construct
SEQUENCE: 1
agacaatcaa ccatttgggg tggacagcct tgacctctag acttcggcat tttttttttt  60
tt                                                                 62

SEQ ID NO: 2             moltype = DNA  length = 112
FEATURE                  Location/Qualifiers
misc_feature             1..112
                         note = Description of Artificial Sequence:
                          Syntheticpolynucleotide
modified_base            101..102
                         mod_base = OTHER
                         note = Thymidine-succinyl hexamide CED phosphoramidite
source                   1..112
                         mol_type = other DNA
                         organism = synthetic construct
SEQUENCE: 2
cgggatcctt atcgtcatcg tcgtacagat cccgacccat ttgctgtcca ccagtcatgc  60
tagccatacc atgatgatga tgatgatgag aaccccgcat tttttttttt tt         112

SEQ ID NO: 3             moltype = DNA  length = 19
FEATURE                  Location/Qualifiers
misc_feature             1..19
                         note = Description of Artificial Sequence: Syntheticprimer
source                   1..19
                         mol_type = other DNA
                         organism = synthetic construct
SEQUENCE: 3
atgcggggtt ctcatcatc                                               19

SEQ ID NO: 4             moltype = DNA  length = 20
FEATURE                  Location/Qualifiers
misc_feature             1..20
                         note = Description of Artificial Sequence: Syntheticprimer
source                   1..20
                         mol_type = other DNA
                         organism = synthetic construct
SEQUENCE: 4
cgggatcctt atcgtcatcg                                              20
```